(12) United States Patent
Sicotte et al.

(10) Patent No.: US 11,998,438 B2
(45) Date of Patent: Jun. 4, 2024

(54) SYSTEMS, DEVICES, AND METHODS FOR THE ACCURATE DEPLOYMENT OF AN IMPLANT IN THE PROSTATIC URETHRA

(71) Applicant: ZENFLOW, INC., San Francisco, CA (US)

(72) Inventors: Marcel Song Sicotte, San Francisco, CA (US); Austin Michael Bly, San Clemente, CA (US); Ben Collett-Nye, Kumeu (NZ); Shreya Mehta, San Francisco, CA (US)

(73) Assignee: ZENFLOW, INC., San Francisco, CA (US)

( * ) Notice: Subject to any disclaimer, the term of this patent is extended or adjusted under 35 U.S.C. 154(b) by 117 days.

(21) Appl. No.: 17/380,377

(22) Filed: Jul. 20, 2021

(65) Prior Publication Data

US 2022/0079736 A1    Mar. 17, 2022

Related U.S. Application Data

(63) Continuation of application No. 16/433,463, filed on Jun. 6, 2019, now Pat. No. 11,096,774, which is a
(Continued)

(51) Int. Cl.
| | |
|---|---|
| *A61F 2/06* | (2013.01) |
| *A61B 17/00* | (2006.01) |
| *A61B 17/34* | (2006.01) |
| *A61F 2/04* | (2013.01) |
| *A61F 2/82* | (2013.01) |
| *A61F 2/88* | (2006.01) |

(Continued)

(52) U.S. Cl.
CPC .......... *A61F 2/042* (2013.01); *A61B 17/3468* (2013.01); *A61F 2/885* (2013.01); *A61F 2/966* (2013.01); *A61B 2017/00274* (2013.01); *A61F 2002/047* (2013.01); *A61F 2250/001* (2013.01); *F16H 1/06* (2013.01); *F16H 1/28* (2013.01)

(58) Field of Classification Search
None
See application file for complete search history.

(56) References Cited

U.S. PATENT DOCUMENTS

| | | | |
|---|---|---|---|
| 3,657,744 | A | 4/1972 | Ersek |
| 5,041,126 | A | 8/1991 | Gianturco |
| | (Continued) | | |

FOREIGN PATENT DOCUMENTS

| | | |
|---|---|---|
| CN | 202891882 U | 4/2013 |
| CN | 103815859 A | 5/2014 |
| | (Continued) | |

OTHER PUBLICATIONS

JP, 2021-161089 Office Action, Mar. 16, 2023.
(Continued)

*Primary Examiner* — Ann Schillinger
(74) *Attorney, Agent, or Firm* — ONE LLP

(57) ABSTRACT

Systems, devices, and methods are provided for the delivery of an implant into the prostatic urethra. Embodiments of delivery systems can include a delivery device for insertion into the patient and a proximal control device for use in controlling release of the implant from the delivery device.

29 Claims, 23 Drawing Sheets

Related U.S. Application Data continuation of application No. PCT/US2017/065469, filed on Dec. 8, 2017.

(60) Provisional application No. 62/432,542, filed on Dec. 9, 2016.

(51) Int. Cl.

| | | |
|---|---|---|
| A61F 2/95 | (2013.01) | |
| A61F 2/966 | (2013.01) | |
| A61M 25/01 | (2006.01) | |
| F16H 1/06 | (2006.01) | |
| F16H 1/28 | (2006.01) | |

(56) References Cited

U.S. PATENT DOCUMENTS

| | | |
|---|---|---|
| 5,160,341 A | 11/1992 | Brenneman et al. |
| 5,246,445 A | 9/1993 | Yachia |
| 5,261,916 A | 11/1993 | Engelson |
| 5,269,802 A | 12/1993 | Garber |
| 5,372,600 A | 12/1994 | Beyar et al. |
| 5,413,601 A | 5/1995 | Keshelava |
| 5,433,723 A | 7/1995 | Lindenberg et al. |
| 5,466,242 A | 11/1995 | Mori |
| 5,490,860 A | 2/1996 | Middle et al. |
| 5,507,767 A | 4/1996 | Maeda et al. |
| 5,514,176 A | 5/1996 | Bosley |
| 5,514,178 A | 5/1996 | Torchio |
| 5,531,718 A | 7/1996 | Sachse |
| 5,540,701 A | 7/1996 | Sharkey et al. |
| 5,540,713 A | 7/1996 | Schnepp Pesch et al. |
| 5,545,210 A | 8/1996 | Hess et al. |
| 5,554,181 A | 9/1996 | Das |
| 5,556,413 A | 9/1996 | Lam |
| 5,556,414 A | 9/1996 | Turi |
| 5,562,641 A | 10/1996 | Flomenblit et al. |
| 5,603,722 A | 2/1997 | Phan et al. |
| 5,607,445 A | 3/1997 | Summers |
| 5,609,629 A | 3/1997 | Fearnot et al. |
| 5,634,946 A | 6/1997 | Slepian |
| 5,658,311 A | 8/1997 | Baden |
| 5,662,713 A | 9/1997 | Andersen et al. |
| 5,667,486 A | 9/1997 | Mikulich et al. |
| 5,667,522 A | 9/1997 | Flomenblit et al. |
| 5,674,241 A | 10/1997 | Bley et al. |
| 5,674,242 A | 10/1997 | Phan et al. |
| 5,681,274 A | 10/1997 | Perkins et al. |
| 5,685,824 A | 11/1997 | Takei |
| 5,725,549 A | 3/1998 | Lam |
| 5,749,915 A | 5/1998 | Slepian |
| 5,749,918 A | 5/1998 | Hogendijk et al. |
| 5,772,668 A | 6/1998 | Summers et al. |
| 5,782,838 A | 7/1998 | Beyar et al. |
| 5,792,165 A * | 8/1998 | Klieman ............ A61B 17/2909 606/174 |
| 5,797,952 A | 8/1998 | Klein |
| 5,824,040 A | 10/1998 | Cox et al. |
| 5,824,049 A | 10/1998 | Ragheb et al. |
| 5,830,179 A | 11/1998 | Mikus et al. |
| 5,830,228 A | 11/1998 | Knapp et al. |
| 5,843,168 A | 12/1998 | Dang |
| 5,861,035 A | 1/1999 | Griffith |
| 5,865,815 A | 2/1999 | Tihon |
| 5,873,904 A | 2/1999 | Ragheb et al. |
| 5,876,434 A | 3/1999 | Flomenblit et al. |
| 5,876,445 A | 3/1999 | Andersen et al. |
| 5,899,934 A | 5/1999 | Amundson et al. |
| 5,907,893 A | 6/1999 | Zadno Azizi et al. |
| 5,928,217 A | 7/1999 | Mikus et al. |
| 5,929,901 A | 7/1999 | Adair et al. |
| 5,938,585 A | 8/1999 | Donofrio |
| 5,954,766 A | 9/1999 | Zadno Azizi et al. |
| 5,964,771 A | 10/1999 | Beyar et al. |
| 5,968,070 A | 10/1999 | Bley et al. |
| 5,972,027 A | 10/1999 | Johnson |
| 5,980,554 A | 11/1999 | Lenker et al. |
| 6,013,854 A | 1/2000 | Moriuchi |
| 6,019,779 A | 2/2000 | Thorud et al. |
| 6,022,312 A | 2/2000 | Chaussy et al. |
| 6,033,413 A | 3/2000 | Mikus et al. |
| 6,036,702 A | 3/2000 | Bachinski et al. |
| 6,053,943 A | 4/2000 | Edwin et al. |
| 6,059,808 A | 5/2000 | Boussignac et al. |
| 6,086,528 A | 7/2000 | Adair |
| 6,090,115 A | 7/2000 | Beyar et al. |
| 6,090,134 A | 7/2000 | Tu et al. |
| 6,096,070 A | 8/2000 | Ragheb et al. |
| 6,136,023 A | 10/2000 | Boyle |
| 6,139,536 A | 10/2000 | Mikus et al. |
| 6,165,194 A | 12/2000 | Denardo |
| 6,174,305 B1 | 1/2001 | Mikus et al. |
| 6,190,394 B1 | 2/2001 | Lind et al. |
| 6,197,051 B1 | 3/2001 | Zhong |
| 6,203,552 B1 | 3/2001 | Bagley et al. |
| 6,211,904 B1 | 4/2001 | Adair et al. |
| 6,238,430 B1 | 5/2001 | Klumb et al. |
| 6,248,122 B1 | 6/2001 | Klumb et al. |
| 6,253,443 B1 | 7/2001 | Johnson |
| 6,258,115 B1 | 7/2001 | Dubrul |
| 6,258,118 B1 | 7/2001 | Baum et al. |
| 6,283,991 B1 | 9/2001 | Cox et al. |
| 6,305,436 B1 | 10/2001 | Andersen et al. |
| 6,306,141 B1 | 10/2001 | Jervis |
| 6,310,642 B1 | 10/2001 | Adair et al. |
| 6,315,791 B1 | 11/2001 | Gingras et al. |
| 6,327,772 B1 | 12/2001 | Zadno Azizi et al. |
| 6,332,892 B1 | 12/2001 | Desmond et al. |
| 6,371,953 B1 | 4/2002 | Beyar et al. |
| 6,375,458 B1 | 4/2002 | Moorleghem et al. |
| 6,379,379 B1 | 4/2002 | Wang |
| 6,395,021 B1 | 5/2002 | Hart et al. |
| 6,409,750 B1 * | 6/2002 | Hyodoh ................ A61F 2/856 623/1.1 |
| 6,413,269 B1 | 7/2002 | Bui et al. |
| 6,413,273 B1 | 7/2002 | Baum et al. |
| 6,416,545 B1 | 7/2002 | Mikus et al. |
| 6,488,700 B2 | 12/2002 | Klumb et al. |
| 6,497,724 B1 | 12/2002 | Stevens et al. |
| 6,506,211 B1 | 1/2003 | Skubitz et al. |
| 6,514,285 B1 | 2/2003 | Pinchasik |
| 6,530,951 B1 | 3/2003 | Bates et al. |
| 6,562,064 B1 | 5/2003 | deBeer |
| 6,572,648 B1 | 6/2003 | Klumb et al. |
| 6,585,753 B2 | 7/2003 | Eder et al. |
| 6,602,281 B1 | 8/2003 | Klein |
| 6,605,107 B1 | 8/2003 | Klein |
| 6,616,653 B2 | 9/2003 | Beyar et al. |
| 6,629,981 B2 | 10/2003 | Bui et al. |
| 6,632,243 B1 | 10/2003 | Zadno Azizi et al. |
| 6,641,605 B1 | 11/2003 | Stergiopulos |
| 6,645,237 B2 | 11/2003 | Klumb et al. |
| 6,652,575 B2 | 11/2003 | Wang |
| 6,660,032 B2 | 12/2003 | Klumb et al. |
| 6,699,279 B2 | 3/2004 | Stevens et al. |
| 6,702,829 B2 | 3/2004 | Bachinski et al. |
| 6,702,846 B2 | 3/2004 | Mikus et al. |
| 6,706,408 B2 | 3/2004 | Jelle |
| 6,733,536 B1 | 5/2004 | Gellman |
| 6,746,489 B2 | 6/2004 | Dua et al. |
| 6,755,854 B2 | 6/2004 | Gillick et al. |
| 6,764,519 B2 | 7/2004 | Whitmore |
| 6,770,101 B2 | 8/2004 | Desmond et al. |
| 6,774,278 B1 | 8/2004 | Ragheb et al. |
| 6,790,223 B2 | 9/2004 | Reever |
| 6,792,979 B2 | 9/2004 | Konya et al. |
| 6,805,704 B1 | 10/2004 | Hoyns |
| 6,830,588 B2 | 12/2004 | Furukawa et al. |
| 6,887,215 B2 | 5/2005 | McWeeney |
| 6,887,270 B2 | 5/2005 | Miller et al. |
| 6,921,414 B2 | 7/2005 | Klumb et al. |
| 6,926,734 B1 | 8/2005 | Klein |
| 6,939,372 B2 | 9/2005 | Dong |
| 6,941,950 B2 | 9/2005 | Wilson et al. |

(56) References Cited

U.S. PATENT DOCUMENTS

| | | | |
|---|---|---|---|
| 6,949,125 B2 | 9/2005 | Robertson |
| 6,974,473 B2 | 12/2005 | Barclay et al. |
| 6,982,740 B2 | 1/2006 | Adair et al. |
| 6,982,742 B2 | 1/2006 | Adair et al. |
| 6,997,952 B2 | 2/2006 | Furukawa et al. |
| 7,004,965 B2 | 2/2006 | Gross |
| 7,011,094 B2 | 3/2006 | Rapacki et al. |
| 7,018,401 B1 | 3/2006 | Hyodoh et al. |
| 7,029,495 B2 | 4/2006 | Stinson |
| 7,033,385 B2 | 4/2006 | Eder et al. |
| 7,033,387 B2 | 4/2006 | Zadno Azizi et al. |
| 7,044,981 B2 | 5/2006 | Liu et al. |
| 7,048,014 B2 | 5/2006 | Hyodoh et al. |
| 7,056,294 B2 * | 6/2006 | Khairkhahan ... A61B 17/32075 |
| | | | 606/167 |
| 7,063,720 B2 | 6/2006 | Iki et al. |
| 7,066,952 B2 | 6/2006 | Igaki |
| 7,094,248 B2 | 8/2006 | Bachinski et al. |
| 7,112,226 B2 | 9/2006 | Gellman |
| 7,118,600 B2 | 10/2006 | Dua et al. |
| 7,169,175 B2 | 1/2007 | Cottone et al. |
| 7,192,440 B2 | 3/2007 | Andreas et al. |
| 7,211,095 B2 | 5/2007 | Bachinski et al. |
| 7,214,229 B2 | 5/2007 | Mitchell et al. |
| 7,226,473 B2 | 6/2007 | Brar et al. |
| 7,276,077 B2 | 10/2007 | Zadno Azizi et al. |
| 7,294,146 B2 | 11/2007 | Chew et al. |
| 7,309,352 B2 | 12/2007 | Eder et al. |
| 7,316,663 B2 | 1/2008 | Whitmore |
| 7,326,240 B1 | 2/2008 | Caro et al. |
| 7,331,988 B2 | 2/2008 | Igaki |
| 7,331,991 B2 | 2/2008 | Kheradvar et al. |
| 7,335,226 B2 | 2/2008 | Igaki |
| 7,347,868 B2 | 3/2008 | Burnett et al. |
| 7,374,564 B2 | 5/2008 | Brown |
| 7,410,665 B2 | 8/2008 | Ragheb et al. |
| 7,468,052 B2 | 12/2008 | Brar et al. |
| 7,470,247 B2 | 12/2008 | Aliski et al. |
| 7,491,229 B2 | 2/2009 | Eder et al. |
| 7,507,218 B2 | 3/2009 | Aliski et al. |
| 7,507,247 B2 | 3/2009 | Huxel et al. |
| 7,582,108 B2 | 9/2009 | Hierlemann et al. |
| 7,611,533 B2 | 11/2009 | Bates et al. |
| 7,632,297 B2 | 12/2009 | Gross |
| 7,632,299 B2 | 12/2009 | Weber |
| 7,682,381 B2 | 3/2010 | Rakos et al. |
| 7,775,972 B2 | 8/2010 | Brock et al. |
| 7,794,494 B2 | 9/2010 | Sahatjian et al. |
| 7,799,070 B2 | 9/2010 | Bates et al. |
| 7,828,715 B2 | 11/2010 | Haverfield |
| 7,842,098 B2 | 11/2010 | Rioux et al. |
| 7,846,202 B2 | 12/2010 | Bates et al. |
| 7,850,705 B2 | 12/2010 | Bachinski et al. |
| 7,862,605 B2 | 1/2011 | Ragheb et al. |
| 7,862,607 B2 | 1/2011 | McDermott et al. |
| 7,867,275 B2 | 1/2011 | Bates et al. |
| 7,871,367 B2 | 1/2011 | Anderson et al. |
| 7,878,972 B2 | 2/2011 | D'Amelio et al. |
| 7,882,841 B2 | 2/2011 | Aljuri et al. |
| 7,896,914 B2 | 3/2011 | Bates et al. |
| 7,922,650 B2 | 4/2011 | McWeeney et al. |
| 7,942,917 B2 | 5/2011 | Nowak |
| 7,955,372 B2 | 6/2011 | Butterwick et al. |
| 7,963,990 B2 | 6/2011 | Johnson |
| 7,993,391 B2 | 8/2011 | Stinson |
| 7,998,187 B2 | 8/2011 | Hartley et al. |
| 8,007,540 B2 | 8/2011 | Robertson |
| 8,007,702 B2 | 8/2011 | Gellman |
| 8,016,742 B2 | 9/2011 | Whalen et al. |
| 8,016,880 B2 | 9/2011 | Cook et al. |
| 8,021,384 B2 | 9/2011 | Weiss et al. |
| 8,029,557 B2 | 10/2011 | Sobrino-Serrano et al. |
| 8,043,359 B2 | 10/2011 | Edin |
| 8,052,670 B2 | 11/2011 | Sachdeva et al. |
| 8,066,759 B2 | 11/2011 | Weber et al. |
| 8,070,795 B2 | 12/2011 | Hashimoto et al. |
| 8,070,824 B2 | 12/2011 | Burnett et al. |
| 8,088,170 B2 | 1/2012 | Whitmore |
| 8,092,864 B2 | 1/2012 | Isch et al. |
| 8,101,275 B2 | 1/2012 | Schüssler et al. |
| 8,105,666 B2 | 1/2012 | Finley |
| 8,109,990 B2 | 2/2012 | Paul et al. |
| 8,137,687 B2 | 3/2012 | Chen et al. |
| 8,145,321 B2 | 3/2012 | Gross |
| 8,158,187 B2 | 4/2012 | Chen et al. |
| 8,160,678 B2 | 4/2012 | Cropper et al. |
| 8,182,459 B2 | 5/2012 | Dann et al. |
| 8,197,529 B2 | 6/2012 | Cully et al. |
| 8,206,436 B2 | 6/2012 | Mangiardi et al. |
| 8,221,505 B2 | 7/2012 | Skerven |
| 8,226,704 B2 | 7/2012 | Caro et al. |
| 8,236,043 B2 | 8/2012 | Caro et al. |
| 8,241,548 B2 | 8/2012 | Gellman |
| 8,257,433 B2 | 9/2012 | Bates et al. |
| 8,282,678 B2 | 10/2012 | Yachia et al. |
| 8,287,589 B2 | 10/2012 | Otto et al. |
| 8,287,602 B2 | 10/2012 | Daignault et al. |
| 8,308,629 B2 | 11/2012 | Watschke et al. |
| 8,328,865 B2 | 12/2012 | Bales et al. |
| 8,333,799 B2 | 12/2012 | Bales et al. |
| 8,343,207 B2 | 1/2013 | Rakos et al. |
| 8,371,998 B2 | 2/2013 | Haverfield |
| 8,372,138 B2 | 2/2013 | Jordan |
| 8,388,676 B2 | 3/2013 | Stinson |
| 8,409,270 B2 | 4/2013 | Clerc et al. |
| 8,414,635 B2 | 4/2013 | Hyodoh et al. |
| 8,419,786 B2 | 4/2013 | Cottone et al. |
| 8,463,005 B2 | 6/2013 | Erbel et al. |
| 8,465,453 B2 | 6/2013 | Sandhu et al. |
| 8,465,551 B1 | 6/2013 | Wijay et al. |
| 8,475,516 B2 | 7/2013 | Paul et al. |
| 8,487,284 B2 | 7/2013 | Tateshima et al. |
| 8,500,793 B2 | 8/2013 | Zipse et al. |
| 8,500,821 B2 | 8/2013 | Sobrino-Serrano et al. |
| 8,512,219 B2 | 8/2013 | Ferren et al. |
| 8,523,936 B2 | 9/2013 | Schmid et al. |
| 8,535,366 B2 * | 9/2013 | Mangiardi ............ A61F 2/95 |
| | | | 606/198 |
| 8,556,956 B2 | 10/2013 | Cully et al. |
| 8,568,643 B2 | 10/2013 | Gellman |
| 8,579,936 B2 * | 11/2013 | Abbott ............... A61B 17/29 |
| | | | 606/213 |
| 8,579,988 B2 | 11/2013 | Burnett et al. |
| 8,585,730 B2 | 11/2013 | Eaton et al. |
| 8,585,731 B2 | 11/2013 | Abbate et al. |
| 8,591,569 B2 | 11/2013 | Shin et al. |
| 8,608,639 B2 | 12/2013 | Bartning et al. |
| 8,609,123 B2 | 12/2013 | Hossainy et al. |
| 8,647,379 B2 | 2/2014 | McDermott et al. |
| 8,652,197 B2 | 2/2014 | Paul et al. |
| 8,672,996 B2 | 3/2014 | Nelson et al. |
| 8,673,020 B2 | 3/2014 | Sobrino-Serrano et al. |
| 8,674,035 B2 | 3/2014 | Padsalgikar |
| 8,678,046 B2 | 3/2014 | Melder et al. |
| 8,690,817 B2 | 4/2014 | Assaf et al. |
| 8,691,264 B2 | 4/2014 | Li et al. |
| 8,696,735 B2 | 4/2014 | Caro et al. |
| 8,696,736 B2 | 4/2014 | Yachia et al. |
| 8,702,788 B2 | 4/2014 | Kheradvar et al. |
| 8,708,953 B2 | 4/2014 | Salahieh et al. |
| 8,715,337 B2 | 5/2014 | Chuter |
| 8,764,847 B2 | 7/2014 | Knapp |
| 8,777,979 B2 * | 7/2014 | Shrivastava ..... A61B 17/12154 |
| | | | 606/200 |
| 8,784,465 B2 | 7/2014 | Sahatjian et al. |
| 8,784,473 B2 | 7/2014 | Tupil et al. |
| 8,784,476 B2 | 7/2014 | Caro et al. |
| 8,801,593 B2 | 8/2014 | Haverfield |
| 8,801,770 B2 | 8/2014 | Takayuki et al. |
| 8,808,354 B2 | 8/2014 | Caro et al. |
| 8,834,338 B2 | 9/2014 | Srivastava et al. |
| 8,834,492 B2 | 9/2014 | McLean et al. |
| 8,845,599 B2 | 9/2014 | Teague et al. |
| 8,852,265 B2 | 10/2014 | Clerc et al. |

(56) References Cited

U.S. PATENT DOCUMENTS

| | | |
|---|---|---|
| 8,876,880 B2 | 11/2014 | Hyodoh et al. |
| 8,920,513 B2 | 12/2014 | Rickner |
| 8,928,746 B1 | 1/2015 | Stevrin et al. |
| 8,936,634 B2 | 1/2015 | Irwin et al. |
| 9,149,176 B2 | 10/2015 | Greenberg et al. |
| 9,186,052 B1 | 11/2015 | Adair et al. |
| 9,358,076 B2 | 6/2016 | Moll et al. |
| 9,872,981 B2 * | 1/2018 | Sparks ............ A61B 6/12 |
| 10,159,506 B2 * | 12/2018 | Boudreaux ......... A61B 17/295 |
| 10,653,427 B2 * | 5/2020 | Goldfarb .......... A61B 17/1285 |
| 11,096,774 B2 * | 8/2021 | Sicotte ............ A61B 17/3468 |
| 11,253,262 B2 * | 2/2022 | Miles ............. A61B 17/12177 |
| 2001/0010007 A1 | 7/2001 | Bachinski et al. |
| 2001/0010015 A1 | 7/2001 | Hijlkema |
| 2001/0018611 A1 | 8/2001 | Solem et al. |
| 2001/0029660 A1 | 10/2001 | Johnson |
| 2002/0007206 A1 * | 1/2002 | Bui ................. A61F 2/962 623/1.11 |
| 2002/0007222 A1 | 1/2002 | Desai |
| 2002/0035391 A1 | 3/2002 | Mikus et al. |
| 2002/0077693 A1 | 6/2002 | Barclay et al. |
| 2002/0077696 A1 | 6/2002 | Zadno Azizi et al. |
| 2002/0082679 A1 | 6/2002 | Sirhan et al. |
| 2002/0082682 A1 | 6/2002 | Barclay et al. |
| 2002/0095209 A1 | 7/2002 | Zadno Azizi et al. |
| 2002/0120327 A1 | 8/2002 | Cox et al. |
| 2002/0123789 A1 | 9/2002 | Francis et al. |
| 2002/0143390 A1 | 10/2002 | Ishii |
| 2002/0161114 A1 | 10/2002 | Gunatillake et al. |
| 2002/0173809 A1 | 11/2002 | Fleischman et al. |
| 2002/0173810 A1 | 11/2002 | Bachinski et al. |
| 2003/0028244 A1 | 2/2003 | Bates et al. |
| 2003/0040772 A1 | 2/2003 | Hyodoh et al. |
| 2003/0055313 A1 | 3/2003 | Anderson et al. |
| 2003/0074052 A1 | 4/2003 | Besselink |
| 2003/0105515 A1 | 6/2003 | Skubitz et al. |
| 2003/0135268 A1 | 7/2003 | Desai |
| 2003/0153971 A1 | 8/2003 | Chandrasekaran |
| 2003/0153972 A1 | 8/2003 | Helmus |
| 2003/0195609 A1 | 10/2003 | Berenstein et al. |
| 2003/0229364 A1 | 12/2003 | Seiba |
| 2004/0054377 A1 | 3/2004 | Foster et al. |
| 2004/0078088 A1 | 4/2004 | Gellman |
| 2004/0087886 A1 | 5/2004 | Gellman |
| 2004/0087997 A1 | 5/2004 | Brenneman |
| 2004/0088043 A1 | 5/2004 | Klein |
| 2004/0092892 A1 | 5/2004 | Kagan et al. |
| 2004/0098119 A1 | 5/2004 | Wang |
| 2004/0106975 A1 | 6/2004 | Solovay et al. |
| 2004/0153142 A1 | 8/2004 | Klumb et al. |
| 2004/0167635 A1 | 8/2004 | Yachia et al. |
| 2004/0171747 A1 | 9/2004 | Zhong |
| 2004/0199262 A1 | 10/2004 | Dua et al. |
| 2004/0236414 A1 | 11/2004 | Brar et al. |
| 2004/0249441 A1 | 12/2004 | Miller et al. |
| 2005/0010275 A1 | 1/2005 | Sahatjian et al. |
| 2005/0021131 A1 | 1/2005 | Venkatraman et al. |
| 2005/0025752 A1 | 2/2005 | Kutryk et al. |
| 2005/0033314 A1 | 2/2005 | Sakurai et al. |
| 2005/0033399 A1 | 2/2005 | Richter |
| 2005/0038455 A1 | 2/2005 | Bates et al. |
| 2005/0049673 A1 | 3/2005 | Andreas et al. |
| 2005/0049681 A1 | 3/2005 | Greenhalgh et al. |
| 2005/0060030 A1 * | 3/2005 | Lashinski ............ A61F 2/2466 623/2.37 |
| 2005/0075721 A1 | 4/2005 | Klein |
| 2005/0096750 A1 | 5/2005 | Kagan et al. |
| 2005/0131515 A1 | 6/2005 | Cully et al. |
| 2005/0131525 A1 | 6/2005 | Hartley |
| 2005/0145253 A1 | 7/2005 | Wilson et al. |
| 2005/0163821 A1 | 7/2005 | Sung et al. |
| 2005/0166925 A1 | 8/2005 | Wilson et al. |
| 2005/0171599 A1 | 8/2005 | White |
| 2005/0182477 A1 | 8/2005 | White |
| 2005/0187428 A1 | 8/2005 | Rinman |
| 2005/0187510 A1 | 8/2005 | McWeeney |
| 2005/0187609 A1 | 8/2005 | Brar et al. |
| 2005/0222677 A1 | 10/2005 | Bates et al. |
| 2005/0228417 A1 | 10/2005 | Teitelbaum et al. |
| 2005/0240141 A1 | 10/2005 | Aliski et al. |
| 2005/0240278 A1 | 10/2005 | Aliski et al. |
| 2006/0004436 A1 | 1/2006 | Amarant et al. |
| 2006/0030753 A1 | 2/2006 | Boutillette et al. |
| 2006/0058869 A1 | 3/2006 | Olson et al. |
| 2006/0076023 A1 | 4/2006 | Rapacki et al. |
| 2006/0095058 A1 | 5/2006 | Sivan et al. |
| 2006/0095116 A1 * | 5/2006 | Bolduc ............... A61F 2/954 623/1.16 |
| 2006/0136033 A1 | 6/2006 | Hermann et al. |
| 2006/0136034 A1 | 6/2006 | Modesitt et al. |
| 2006/0136035 A1 | 6/2006 | Hermann et al. |
| 2006/0142794 A1 | 6/2006 | Lendlein et al. |
| 2006/0167538 A1 | 7/2006 | Rucker |
| 2006/0211984 A1 | 9/2006 | Blank et al. |
| 2006/0235504 A1 | 10/2006 | Gonzales |
| 2006/0246210 A1 | 11/2006 | Iki et al. |
| 2006/0253190 A1 | 11/2006 | Kuo |
| 2007/0005125 A1 | 1/2007 | Berenstein et al. |
| 2007/0005148 A1 | 1/2007 | Barofsky et al. |
| 2007/0014773 A1 | 1/2007 | Matheny et al. |
| 2007/0014871 A1 | 1/2007 | Matheny |
| 2007/0014873 A1 | 1/2007 | Matheny |
| 2007/0027285 A1 | 2/2007 | Gunatillake et al. |
| 2007/0043338 A1 * | 2/2007 | Moll ................ A61B 34/30 606/1 |
| 2007/0043433 A1 | 2/2007 | Chandrasekaran |
| 2007/0050018 A1 | 3/2007 | Wainwright |
| 2007/0053952 A1 | 3/2007 | Chen et al. |
| 2007/0112411 A1 | 5/2007 | Obermiller et al. |
| 2007/0141100 A1 | 6/2007 | Sung et al. |
| 2007/0141107 A1 | 6/2007 | Kutryk et al. |
| 2007/0150045 A1 | 6/2007 | Ferrera |
| 2007/0173924 A1 | 7/2007 | Gelbart et al. |
| 2007/0213805 A1 | 9/2007 | Schaeffer et al. |
| 2007/0219616 A1 | 9/2007 | Modesitt et al. |
| 2007/0250148 A1 | 10/2007 | Perry et al. |
| 2007/0293932 A1 | 12/2007 | Zilla et al. |
| 2008/0009662 A1 | 1/2008 | Bartning et al. |
| 2008/0009814 A1 | 1/2008 | Bartning et al. |
| 2008/0015633 A1 | 1/2008 | Abbott et al. |
| 2008/0033230 A1 | 2/2008 | Bartning et al. |
| 2008/0039921 A1 | 2/2008 | Wallsten et al. |
| 2008/0039931 A1 | 2/2008 | Jelle et al. |
| 2008/0045881 A1 | 2/2008 | Teitelbaum et al. |
| 2008/0050418 A1 | 2/2008 | Ranade et al. |
| 2008/0077174 A1 | 3/2008 | Mische |
| 2008/0086214 A1 | 4/2008 | Hardin et al. |
| 2008/0103412 A1 | 5/2008 | Chin |
| 2008/0103440 A1 | 5/2008 | Ferren et al. |
| 2008/0109067 A1 | 5/2008 | Caro et al. |
| 2008/0132988 A1 | 6/2008 | Jordan |
| 2008/0145396 A1 | 6/2008 | Bates et al. |
| 2008/0145399 A1 | 6/2008 | Bates et al. |
| 2008/0183268 A1 | 7/2008 | Bates et al. |
| 2008/0183278 A1 | 7/2008 | Atanasoska et al. |
| 2008/0183299 A1 | 7/2008 | Monga et al. |
| 2008/0195189 A1 | 8/2008 | Asgari |
| 2008/0195196 A1 | 8/2008 | Asgari |
| 2008/0200976 A1 | 8/2008 | Asgari |
| 2008/0208083 A1 | 8/2008 | Lin et al. |
| 2008/0208321 A1 | 8/2008 | Venkatraman et al. |
| 2008/0220040 A1 | 9/2008 | Cheng et al. |
| 2008/0220048 A1 | 9/2008 | Chen et al. |
| 2008/0241899 A1 | 10/2008 | Rhee et al. |
| 2008/0249552 A1 | 10/2008 | Eliachar et al. |
| 2008/0275550 A1 | 11/2008 | Kheradvar et al. |
| 2009/0018486 A1 | 1/2009 | Goren et al. |
| 2009/0030363 A1 | 1/2009 | Gellman |
| 2009/0030370 A1 | 1/2009 | Nishtala et al. |
| 2009/0035350 A1 | 2/2009 | Stankus et al. |
| 2009/0048537 A1 | 2/2009 | Lydon et al. |
| 2009/0081271 A1 | 3/2009 | Clarke et al. |
| 2009/0118817 A1 | 5/2009 | Sandhu et al. |
| 2009/0149947 A1 | 6/2009 | Frohwitter |

(56) References Cited

U.S. PATENT DOCUMENTS

| | | |
|---|---|---|
| 2009/0163934 A1 | 6/2009 | Raschdorf et al. |
| 2009/0177288 A1 | 7/2009 | Wallsten |
| 2009/0182206 A1 | 7/2009 | Najafi et al. |
| 2009/0192588 A1 | 7/2009 | Shin et al. |
| 2009/0192592 A1 | 7/2009 | Asgari |
| 2009/0198179 A1 | 8/2009 | Abbate et al. |
| 2009/0204200 A1 | 8/2009 | Bales et al. |
| 2009/0210045 A1 | 8/2009 | Sørensen et al. |
| 2009/0248141 A1 | 10/2009 | Shandas et al. |
| 2009/0281635 A1 | 11/2009 | Li et al. |
| 2009/0287193 A1 | 11/2009 | Desai et al. |
| 2009/0326637 A1 | 12/2009 | Hashimoto et al. |
| 2010/0042203 A1 | 2/2010 | Cottone et al. |
| 2010/0076574 A1 | 3/2010 | Gellman |
| 2010/0082093 A1 | 4/2010 | Weber |
| 2010/0092535 A1 | 4/2010 | Cook et al. |
| 2010/0094327 A1 | 4/2010 | Milsom et al. |
| 2010/0094399 A1* | 4/2010 | Dorn .............. A61F 2/966 623/1.11 |
| 2010/0100170 A1 | 4/2010 | Tan et al. |
| 2010/0121461 A1 | 5/2010 | Sobrino-Serrano et al. |
| 2010/0122698 A1 | 5/2010 | Shaffer et al. |
| 2010/0145433 A1 | 6/2010 | Anukhin et al. |
| 2010/0174364 A1 | 7/2010 | Hoffman et al. |
| 2010/0204775 A1 | 8/2010 | Edwin |
| 2010/0286760 A1 | 11/2010 | Beach et al. |
| 2010/0324588 A1* | 12/2010 | Miles ............. A61B 17/12122 606/198 |
| 2010/0331954 A1 | 12/2010 | Sahatjian et al. |
| 2011/0040366 A1 | 2/2011 | Goetz et al. |
| 2011/0046723 A1 | 2/2011 | Bates et al. |
| 2011/0071613 A1 | 3/2011 | Wood et al. |
| 2011/0077676 A1 | 3/2011 | Sivan et al. |
| 2011/0093007 A1 | 4/2011 | Abbott et al. |
| 2011/0118820 A1 | 5/2011 | Sandhu et al. |
| 2011/0125251 A1 | 5/2011 | Cottone et al. |
| 2011/0130834 A1 | 6/2011 | Wilson et al. |
| 2011/0160836 A1 | 6/2011 | Behan |
| 2011/0172763 A1 | 7/2011 | Ndondo-Lay |
| 2011/0190662 A1 | 8/2011 | McWeeney |
| 2011/0218387 A1 | 9/2011 | Lamson et al. |
| 2011/0251482 A1 | 10/2011 | Kellerman et al. |
| 2011/0264116 A1 | 10/2011 | Kocur et al. |
| 2011/0295353 A1 | 12/2011 | Harris et al. |
| 2012/0010645 A1 | 1/2012 | Feld |
| 2012/0059486 A1 | 3/2012 | Sobrino-Serrano et al. |
| 2012/0083820 A1 | 4/2012 | Carman et al. |
| 2012/0143306 A1 | 6/2012 | Cully et al. |
| 2012/0150275 A1 | 6/2012 | Shaw-Klein |
| 2012/0158155 A1 | 6/2012 | Shin |
| 2012/0165928 A1 | 6/2012 | Nitzan et al. |
| 2012/0172970 A1 | 7/2012 | Cottone et al. |
| 2012/0191175 A1 | 7/2012 | Costa et al. |
| 2012/0191177 A1 | 7/2012 | Costa et al. |
| 2012/0232459 A1 | 9/2012 | Dann et al. |
| 2012/0238803 A1 | 9/2012 | Lund |
| 2012/0253451 A1 | 10/2012 | Sahatjian et al. |
| 2012/0283811 A1 | 11/2012 | Neilan |
| 2012/0316656 A1 | 12/2012 | Deal et al. |
| 2013/0030521 A1 | 1/2013 | Nitzan et al. |
| 2013/0041208 A1 | 2/2013 | Anderson et al. |
| 2013/0060238 A1 | 3/2013 | Lavelle |
| 2013/0079586 A1 | 3/2013 | Knipfer |
| 2013/0090719 A1 | 4/2013 | Bales et al. |
| 2013/0090721 A1 | 4/2013 | Bales et al. |
| 2013/0116768 A1 | 5/2013 | Rakos et al. |
| 2013/0123934 A1 | 5/2013 | Azar |
| 2013/0131778 A1 | 5/2013 | Igaki et al. |
| 2013/0131785 A1 | 5/2013 | Armstrong et al. |
| 2013/0144372 A1 | 6/2013 | Wood et al. |
| 2013/0150951 A1 | 6/2013 | Jordan |
| 2013/0158675 A1 | 6/2013 | Hutchins et al. |
| 2013/0165742 A1 | 6/2013 | Bartning et al. |
| 2013/0172673 A1 | 7/2013 | Kennedy et al. |
| 2013/0173016 A1 | 7/2013 | Devereux |
| 2013/0184809 A1 | 7/2013 | Stinson |
| 2013/0204347 A1 | 8/2013 | Armstrong et al. |
| 2013/0226282 A1 | 8/2013 | Ahn et al. |
| 2013/0253574 A1* | 9/2013 | Catanese, III .......... A61B 17/42 606/201 |
| 2013/0253662 A1 | 9/2013 | Lamson et al. |
| 2013/0267772 A1 | 10/2013 | Catanese, III et al. |
| 2013/0345786 A1 | 12/2013 | Behan |
| 2014/0004503 A1 | 1/2014 | Cima et al. |
| 2014/0010858 A1 | 1/2014 | Stankus et al. |
| 2014/0012192 A1 | 1/2014 | Bar-On et al. |
| 2014/0018732 A1* | 1/2014 | Bagaoisan ........ A61M 25/0136 604/95.04 |
| 2014/0025158 A1 | 1/2014 | Liddy et al. |
| 2014/0058496 A1 | 2/2014 | Tranquillo et al. |
| 2014/0067042 A1 | 3/2014 | Schmid et al. |
| 2014/0074238 A1 | 3/2014 | Abbate et al. |
| 2014/0079755 A1 | 3/2014 | Eaton et al. |
| 2014/0107062 A1 | 4/2014 | Shenoy |
| 2014/0107765 A1 | 4/2014 | Cottone et al. |
| 2014/0114389 A1 | 4/2014 | Hyodoh et al. |
| 2014/0114432 A1 | 4/2014 | Shalon |
| 2014/0114434 A1 | 4/2014 | Cottone et al. |
| 2014/0121585 A1 | 5/2014 | Baker et al. |
| 2014/0142721 A1 | 5/2014 | Robertson et al. |
| 2014/0148896 A1 | 5/2014 | McDermott et al. |
| 2014/0155987 A1 | 6/2014 | Paul et al. |
| 2014/0172065 A1 | 6/2014 | Lavelle et al. |
| 2014/0172118 A1 | 6/2014 | Pendleton et al. |
| 2014/0188029 A1 | 7/2014 | Assaf et al. |
| 2014/0188249 A1 | 7/2014 | Pendleton et al. |
| 2014/0200677 A1 | 7/2014 | Sobrino-Serrano et al. |
| 2014/0214175 A1 | 7/2014 | Barron et al. |
| 2014/0277564 A1 | 9/2014 | Windheuser et al. |
| 2014/0288627 A1 | 9/2014 | Ouellette et al. |
| 2014/0288630 A1 | 9/2014 | Gerdts et al. |
| 2014/0288636 A1 | 9/2014 | Headley et al. |
| 2014/0288637 A1 | 9/2014 | Clerc et al. |
| 2014/0316512 A1 | 10/2014 | Takayuki et al. |
| 2014/0324144 A1 | 10/2014 | Ye et al. |
| 2014/0330364 A1 | 11/2014 | Tupil et al. |
| 2014/0343243 A1 | 11/2014 | Padsalgikar |
| 2014/0350343 A1 | 11/2014 | Kim |
| 2015/0018602 A1 | 1/2015 | Presthus et al. |
| 2015/0025652 A1 | 1/2015 | McLean et al. |
| 2015/0039078 A1 | 2/2015 | Bales et al. |
| 2015/0245839 A1* | 9/2015 | Wirtel, III .......... A61B 17/0643 606/153 |
| 2015/0257908 A1 | 9/2015 | Chao et al. |
| 2016/0135975 A1 | 5/2016 | Shimoyama |
| 2016/0213230 A1 | 7/2016 | Adair et al. |
| 2017/0135830 A1 | 5/2017 | Harkin et al. |
| 2017/0172677 A1 | 6/2017 | Kernbaum et al. |
| 2017/0172678 A1 | 6/2017 | Dewaele et al. |
| 2018/0126156 A1* | 5/2018 | Sparks ................ A61N 1/057 |
| 2019/0038443 A1 | 2/2019 | Sicotte et al. |
| 2019/0117423 A1 | 4/2019 | Chao et al. |
| 2019/0269420 A1* | 9/2019 | Matusaitis .......... A61B 5/4504 |
| 2020/0038213 A1 | 2/2020 | Bly et al. |
| 2020/0323618 A1 | 10/2020 | Bly et al. |

FOREIGN PATENT DOCUMENTS

| | | |
|---|---|---|
| CN | 204192562 U | 3/2015 |
| CN | 104161493 B | 4/2016 |
| CN | 104545772 B | 8/2016 |
| DE | 103 57 742 A1 | 3/2005 |
| EP | 2 839 872 A1 | 2/2015 |
| WO | WO 98/22159 A2 | 5/1998 |
| WO | WO 01/78576 A2 | 10/2001 |
| WO | WO 02/032321 A1 | 4/2002 |
| WO | WO 2005/016185 A1 | 2/2005 |
| WO | WO 2011/084712 A1 | 7/2011 |

(56) References Cited

FOREIGN PATENT DOCUMENTS

WO    WO 2014/019321 A1    2/2014
WO    WO-2018107081 A1 *  6/2018  ............ A61F 2/966

OTHER PUBLICATIONS

EP, 17879206.5 Supplementary Search Report, Jun. 8, 2020.
EP, 18839359.9 Supplementary Search Report, Mar. 22, 2021.
JP, 2021-161089 Office Action, Sep. 29, 2023.

* cited by examiner

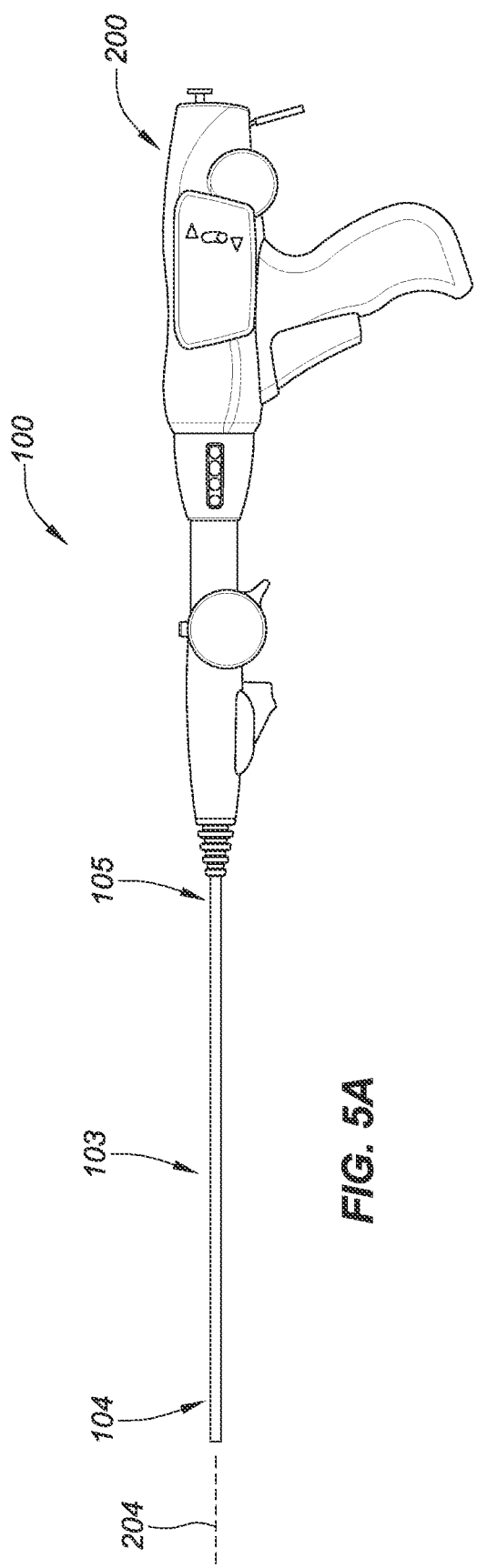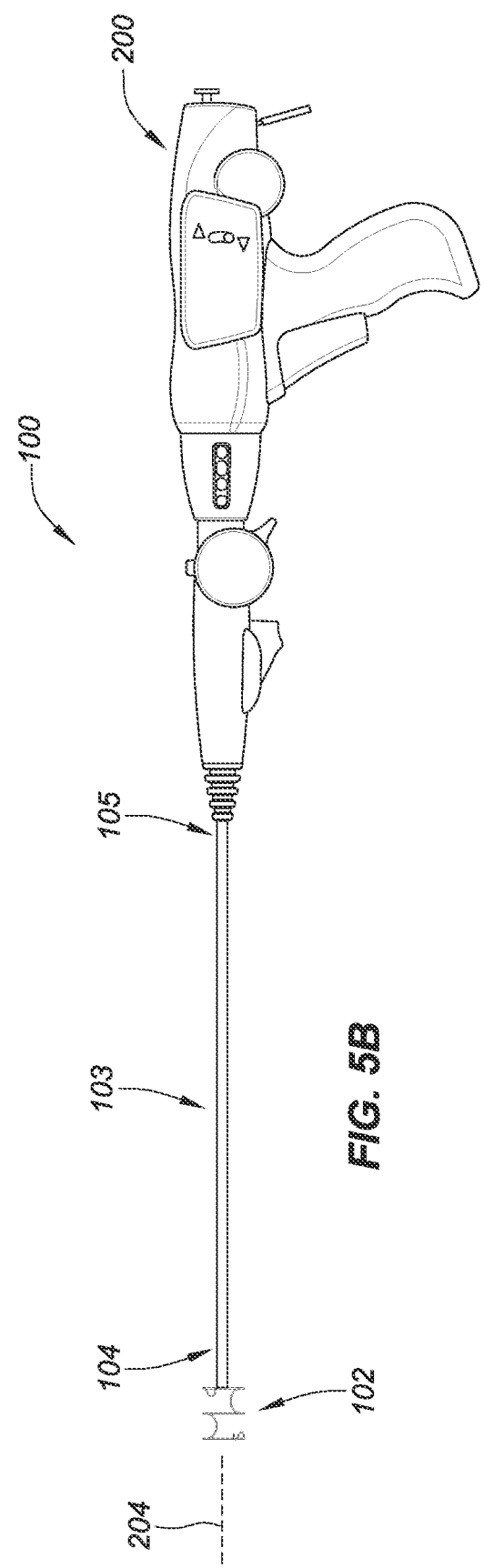

SYSTEMS, DEVICES, AND METHODS FOR THE ACCURATE DEPLOYMENT OF AN IMPLANT IN THE PROSTATIC URETHRA

CROSS-REFERENCE TO RELATED APPLICATIONS

This application is a continuation of U.S. application Ser. No. 16/433,463, filed Jun. 6, 2019, which is a continuation of International Application Serial No. PCT/US17/65469, filed Dec. 8, 2017, which claims priority to and the benefit of U.S. Provisional Application Ser. No. 62/432,542, filed Dec. 9, 2016, all of which are incorporated by reference herein in their entireties for all purposes.

STATEMENT OF GOVERNMENT SPONSOR RESEARCH

This invention was made with government support under NIH SBIR Phase II R44DK112587 awarded by the National Institutes of Health. The government has certain rights in the invention.

FIELD

The subject matter described herein relates to systems, devices, and methods for delivery or deployment of an implant into the prostatic urethra, more specifically, delivery in an atraumatic and minimally-invasive manner through the tortuous bends of the male urethra.

BACKGROUND

There are numerous clinical reasons for placement of an implant into the prostatic urethra, such as for treatment of urinary retention associated with benign prostatic hyperplasia (BPH), blockages from prostate cancer, bladder cancer, urinary tract injury, prostatitis, bladder sphincter dyssynergia, benign or malignant urethral stricture, and other conditions for which treatment is desired. Due to the naturally complex and tortuous anatomical geometry, patient-to-patient geometric and tissue variability, and anatomical restrictions associated with those conditions, accurate and consistent placement of an implant into the prostatic urethral lumen has proven challenging. Furthermore, complex challenges are presented in the design and/or fabrication of systems with sufficient flexibility to deliver such an implant in a minimally-invasive manner. For these and other reasons, needs exist for improved systems, devices, and methods of implant delivery to the prostatic urethra.

SUMMARY

Provided herein are a number of example embodiments of delivery systems for delivering or deploying implants within the prosthetic urethra or other parts of the body, and methods related thereto. Embodiments of the delivery system can include a delivery device insertable into the prosthetic urethra and a proximal control device coupled with the delivery device and configured to control deployment of one or more implants from the delivery device. In some embodiments, the delivery device can include multiple tubular components each having various functions described in more detail herein. Multiple embodiments of implants for use with the delivery systems are also described.

Other systems, devices, methods, features and advantages of the subject matter described herein will be or will become apparent to one with skill in the art upon examination of the following figures and detailed description. It is intended that all such additional systems, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIGS. 5A-5B are side views depicting an example embodiment of a delivery system in various stages of deployment of an implant.

DETAILED DESCRIPTION

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

The subject matter presented herein is described in the context of delivery or deployment of one or more implants within the prostatic urethra. The purpose for deployment of the implant(s) in the prostatic urethra can vary. The embodiments described herein are particularly suited for treatment of BPH, but they are not limited to such. Other conditions for which these embodiments can be used include, but are not limited to, treatment of blockages from prostate cancer, bladder cancer, urinary tract injury, prostatitis, bladder sphincter dyssynergia, and/or benign or malignant urethral stricture. Further, these embodiments can have applicability for deployment of one or more implants in other locations of the urinary tract or in the bladder, as well as other biological lumens, cavities, or spaces, such as the human vasculature, cardiac system, pulmonary system, or gastro-intestinal tract, including locations within the heart, stomach, intestines, liver, spleen, pancreas, and kidney.

Figure 1A:
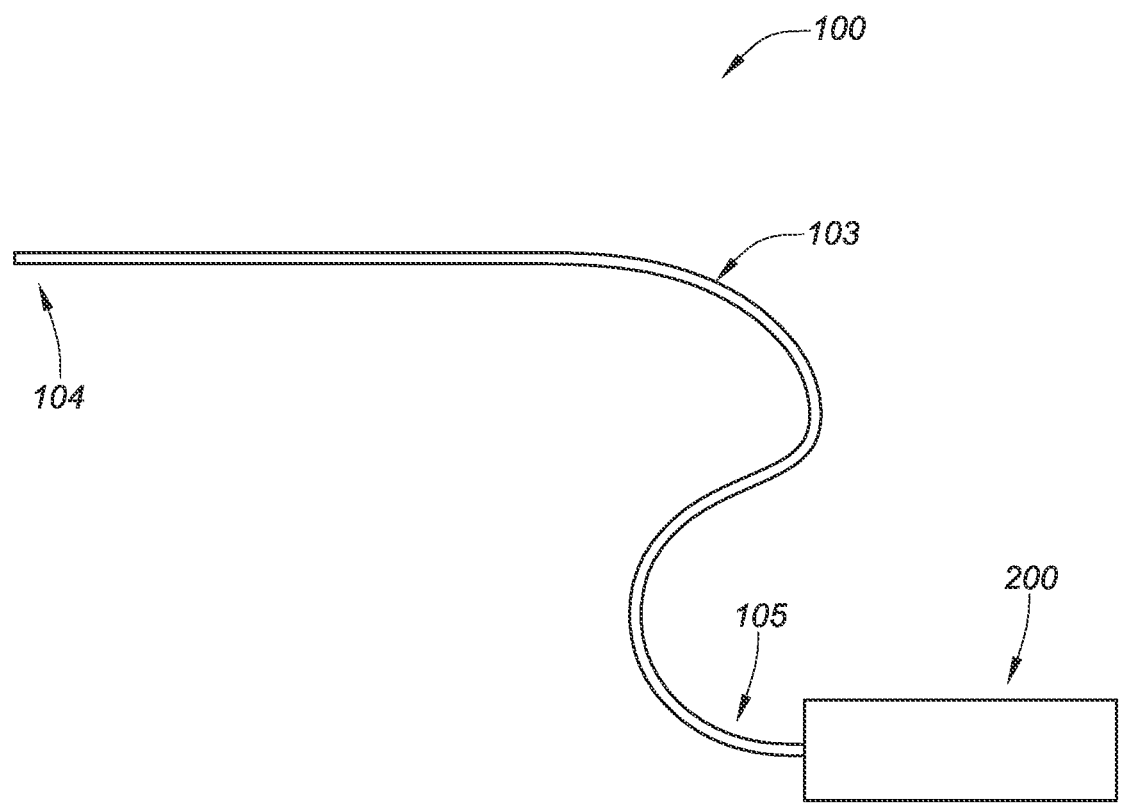
FIG. 1A is a block diagram depicting an example embodiment of a delivery system.

FIG. 1A is a block diagram depicting an example embodiment of delivery system 100 having an elongate delivery device 103 coupled with a proximal control device 200. A distal end region 104 is adapted to be inserted into the patient's urethra (or other lumen or body cavity of the patient) through the urethral orifice. Distal end region 104 preferably has an atraumatic configuration (e.g., relatively soft and rounded) to minimize irritation or trauma to the patient. Elongate delivery device 103 carries or houses one or more implants 102 (not shown) to be delivered or deployed within or adjacent to the prostatic urethra. A proximal end region 105 of delivery device 103 is coupled with proximal control device 200, which remains outside of the patient's body and is configured to be used by the physician or other healthcare professional to control the delivery of one or more implants 102.

Example Embodiments of Delivery Devices and Related Methods

Figure 1B:
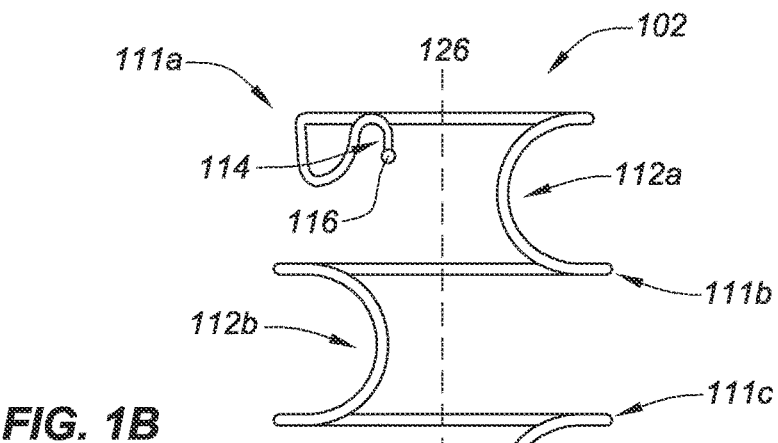
FIGS. 1B, 1C, and 1D are side, end, and perspective views, respectively, depicting an example embodiment of an implant.
Figure 1C:
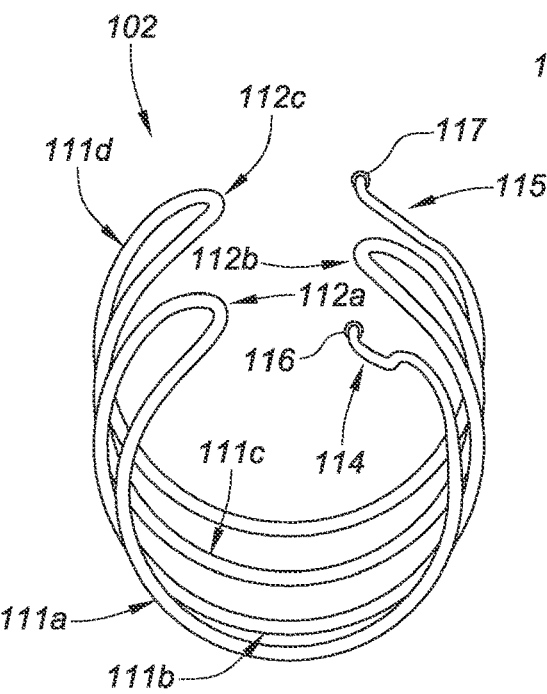
Figure 1D:
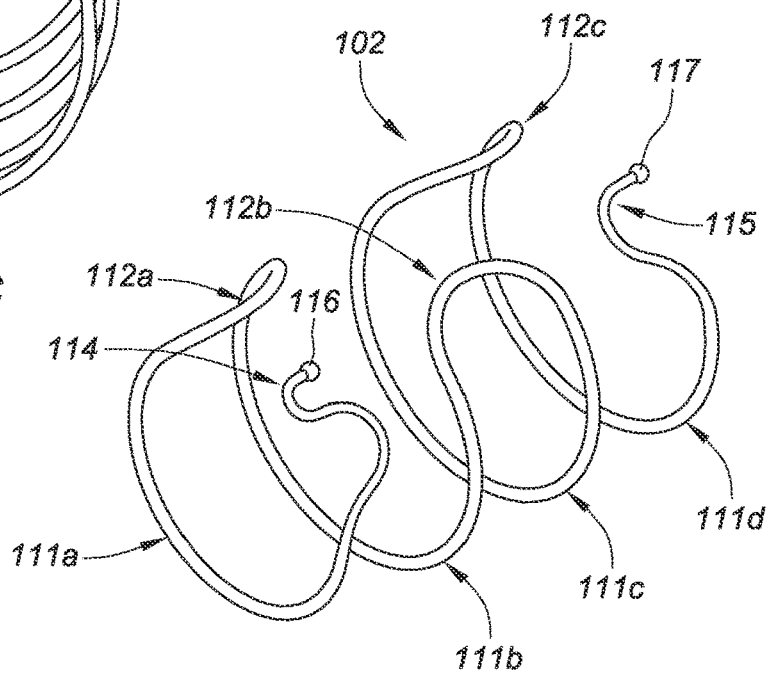

FIGS. 1B, 1C, and 1D are side, end, and perspective views, respectively, depicting an example embodiment of implant 102 in an at-rest configuration. Implantable device 102 is biased towards the at-rest configuration depicted here and is deformable between the at-rest configuration and a relatively more elongate housed (or delivery) configuration (e.g., see FIG. 3A) for housing implant 102 within delivery device 103. The housed configuration can be a straight or lineated state with minimal curvature. The at-rest configuration has a relatively greater lateral width, and a relatively shorter longitudinal length than the housed configuration. Upon exiting an open end of delivery device 103, implant 102 is free to transition its shape back towards that of the at-rest configuration although restraints imparted by the patient's urethral wall may prevent implant 102 from fully reaching the at-rest configuration. Because implant 102 is biased towards the at-rest configuration, implant 102 is configured to automatically expand when freed from the restraint of delivery device 103 and can be referred to as "self-expanding." The shape of implant 102 in its deployed state within, e.g., the patient's urethra, can be referred to as the deployed configuration, and will often be a shape that is deformed from the at-rest configuration by the surrounding tissue, although the deployed configuration can be the same as the at-rest configuration.

Implant 102 can be configured in numerous different ways, including any and all of those implant configurations described in U.S. Patent Publ. No. 2015/0257908 and/or Int'l Publ. No. WO 2017/184887, both of which are incorporated by reference herein for all purposes.

Implant 102 can be formed from one or more discrete bodies (e.g., wires, ribbons, tubular members) of varying geometries. Referring to the embodiment of FIGS. 1B-1D, implant 102 has a main body formed of only one single wire member set in a predetermined shape. Implant 102 can have two or more ring-shaped structures 111 (in this embodiment there are four: 111a, 111b, 111c, and 111d) with one or more interconnections 112 extending between each pair of adjacent ring-shaped structures 111 (in this embodiment there is one interconnection between each adjacent pair, for a total of three: 112a, 112b, and 112c). Each interconnection 112 extends from one ring-shaped structure 111 to an immediately adjacent ring-shaped structure 111. Each interconnection 112 can have a relatively straight shape (not shown) or a curved (e.g., semi-circular or semi-elliptical) shape as shown in FIGS. 1B-1D.

Ring-shaped structures 111 are configured to maintain the urethra in a fully or partially open state when expanded from the housed configuration. Device 100 can be manufactured in various sizes as desired, such that the width (e.g., diameter) of each ring-shaped structure 111 is slightly larger than the width of the urethra, and the length of each interconnection 112 determines the spacing between ring-shaped structures 111. Ring-shaped structures 111 can have the same or different widths. For example, in the embodiment depicted here, ring-shaped structure 111a has a relatively smaller width than structures 111b-111d, which have the same width. This can accommodate prostatic urethras that converge to a smaller geometry before the bladder neck.

Each ring-shaped structure 111 can be located or lie in a single plane, and in some embodiments that single plane can be oriented with a normal axis perpendicular to a central access 124 of implant 102 (as depicted in FIG. 1B). In other embodiments, ring-shaped structures 111 can be located in multiple planes. Ring-shaped structures 111 can extend around central axis 126 to form a complete circle (e.g., a 360-degree revolution) or can form less than a complete circle (e.g., less than 360 degrees) as shown here. Although not limited to such, in many embodiments ring-shaped structures 111 extend between 270 and 360 degrees.

As can be seen from FIGS. 1B-1D, the geometry of implant 102 can have a cylindrical or substantially cylindrical outline shape with a circular or elliptical cross-section. In other embodiments, implant 102 can have a prismatic or substantially prismatic shape with triangular or substantially triangular cross-section, or otherwise.

Implant 102 can also include a distal engagement member 114 and a proximal engagement member 115 that are each configured to engage with elements of delivery device 103. Engagement with delivery device 103 can serve one or more purposes such as allowing control of the release of implant 102, allowing movement of the ends of implant 102 relative to each other, and/or allowing retrieval of implant 102 after deployment, e.g., in an instance where the physician desires to recapture implant 102 and redeploy implant 102 in a different position. In this embodiment, distal engagement member 114 is a wire-like extension from ring-shaped structure 111a that has a curved (e.g., S-like) shape for positioning an atraumatic end 116 (e.g., rounded, spherical, ballized) in a location suitable for engagement with delivery device 103 and thereby allow control of the distal end region of implant 102. Likewise, proximal engagement member 115 has a curved shape for positioning another atraumatic end 117 in a location suitable for engagement with delivery device 103 and thereby allow control of the proximal end region of implant 102. In other embodiments, distal engagement member 114 and proximal engagement member 115 can be omitted, and delivery device 103 can couple with implant 102 at one or more other distal and/or proximal locations, such as on a ring-shaped structure 111 or interconnect 112.

Figure 2A:
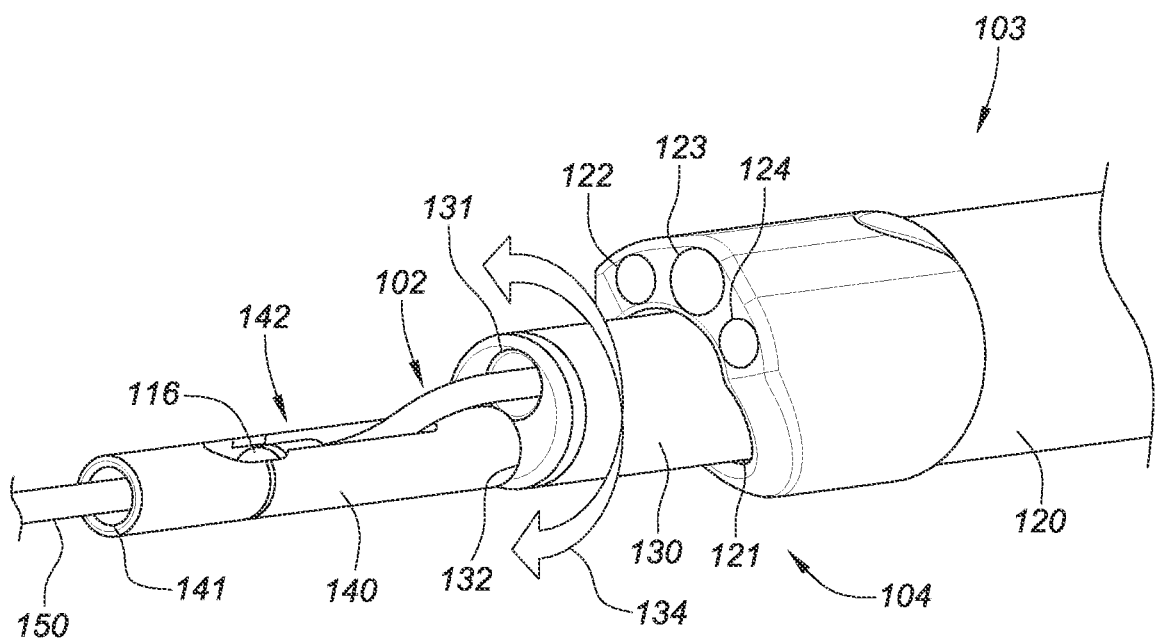
FIGS. 2A-2H are perspective views depicting example embodiments of a delivery system in different stages of deployment of an implant.

Delivery device 103 can include one or more elongate flexible members (e.g., 120, 130, 140, and 150 as described below), each having one or more inner lumens. One or more elongate flexible members of delivery device 103 can be a solid or a non-hollow member with no inner lumen. FIG. 2A is a perspective view depicting an example embodiment of distal end region 104 of a delivery device 103. In this embodiment, delivery device 103 includes a first elongate tubular member 120, a second elongate tubular member 130, a third elongate tubular member 140, and a fourth elongate tubular member 150. Delivery device 103 can vary and in other embodiments can include more or less tubular members.

In this embodiment, first elongate tubular member 120 is the outermost tubular member and is flexible yet provides support for members contained therein. First tubular member 120 is referred to herein as outer shaft 120 and can have one or more inner lumens. In this embodiment, outer shaft 120 includes a first inner lumen 121 housing second elongate tubular member 130, which is referred to herein as inner shaft 130. Outer shaft 120 and inner shaft 130 are each controllable independent of the other. Inner shaft 130 can slide distally and proximally within lumen 121 and is shown here partially extending from an open distal terminus of outer shaft 120.

In this embodiment, outer shaft 120 includes three additional lumens 122, 123, and 124. An illumination device (not shown) and an imaging device (not shown) can be housed in either of lumens 122 and 123. The imaging device can utilize any desired type of imaging modality, such as optical or ultrasound imaging. In one example embodiment the imaging device utilizes a forward (distal) looking CMOS imager. The illumination device can be configured to provide adequate illumination for optical imaging, and in one embodiment includes one or more light emitting diodes (LEDs). In embodiments where illumination is not required, such as for ultrasound imaging, the illumination device and its respective lumen 122 or 123 can be omitted. The illumination device and/or the imaging device can each be fixedly secured at the distal terminuses of lumens 122 and 123, or each can be slidable within lumens 122 and 123 to allow advancement further distally from outer shaft 120 and/or retraction into outer shaft 120. In one example embodiment, the illumination device and the imaging device are mounted together and only a single lumen 122 or 123 is present for that purpose. Lumen 124 can be configured as an irrigation or flush port from which fluid such as saline can be introduced to the urethra to flush the region and provide adequate fluid through which implant 102 and the surrounding prostatic urethra wall can be imaged.

Outer shaft 120 has a proximal end (not shown) coupled with proximal control device 200. Delivery device 103 can be configured to be steerable to navigate tortuous anatomy. Steerability can be unidirectional (e.g., using a single pull wire) or multidirectional (e.g., using two or more pull wires arranged at different radial locations about device 103) depending on the needs of the application. In some embodiments, the structures (e.g., pull wires) for steerability extend from distal end region 104 of delivery device 103 (e.g., where the distal ends of the pull wires are secured to a plate or other structure within distal end region 104) to proximal control device 200, where they can be manipulated by the user to steer delivery device 103. The steering structures can be located in one or more lumens of outer shaft 120 or can be coupled to or embedded within a sidewall of outer shaft 120. Delivery device 103 can be biased to deflect in a particular lateral direction (e.g., bend) such that device 103 automatically deflects in that manner and forces imparted to steer delivery device 103 are in opposition to this biased deflection. Other mechanisms for steering delivery device 103 can also be used. The steering mechanism may also be locked or adjusted during deployment of implant 102 to control the position of implant 102 within the anatomy (e.g., steering anteriorly during deployment may help place implant 102 in a more desirable anterior position).

Inner shaft 130 can include one or more inner lumens for housing one or more implants 102 and/or other components. In this embodiment, inner shaft 130 includes a first lumen 131 in which one or more implants 102 can be housed, and a second lumen 132 in which third elongate tubular member 140 can be housed. In this embodiment, third elongate tubular member 140 is configured to releasably couple with the distal end region of implant 102 and is referred to as a distal control member or tether 140. Distal control member 140 can be slidably advanced and/or retracted with respect to inner shaft 130. Distal control member 140 can include an inner lumen 141 that houses fourth elongate tubular member 150, which is shown here extending from an open distal terminus of distal control member 140. Fourth elongate tubular member 150 is configured to anchor delivery device 103 with respect to the patient's anatomy, e.g., to keep components of delivery device 103 stationary with respect to the anatomy during deployment of implant 102 and is referred to as anchor delivery member 150.

In the configuration depicted in FIG. 2A, anchor delivery member 150 is extended from lumen 141 of distal control member 140, and distal control member 140 along with inner shaft 130 are shown extended from lumen 121 of outer shaft 120. When delivery device 130 is advanced through the urethra, anchor delivery member 150 is preferably housed entirely within distal control member 140, and distal control member 140 along with inner shaft 130 are retracted from the positions shown in FIG. 2A such that they reside within lumen 121 of outer shaft 120 and do not extend from the open distal terminus of lumen 120. In other words, in some embodiments the open distal terminus of outer shaft 120 forms the distalmost structure of device 103 upon initial advancement through the urethra. This facilitates steering of delivery device 103 by outer shaft 120. The physician can advance distal end region 104 of delivery device 103 to be in proximity with the desired implantation site, or entirely into the patient's bladder. Anchor delivery member 150 can be exposed from the open distal terminus of distal control member 140, either by distally advancing anchor delivery member 150 further into the bladder, or if already present within the bladder, then by proximally retracting the other components of delivery device 103. At this point the anchor from anchor delivery member 150 can be deployed in the bladder.

The placement of these components within system 100 is not limited to the embodiments described with respect to FIG. 2A. In some embodiments, outer shaft 120 can be omitted altogether. In such embodiments, visualization of the deployment procedure can be accomplished with external imaging such as fluoroscopy, where implant 102 and delivery device 103 can be radiopaque or can include radiopaque markers, and where the imaging and illumination lumens 122 and 123 (and the imaging and illumination devices), as well as the irrigation lumen are omitted. In some embodiments, instead of distal control member 140 being slidably received within inner shaft 130, distal control member 140 can be slidable within a lumen of outer shaft 120 (either the same lumen receiving inner shaft 130 or a different lumen). Similarly, instead of anchor delivery member 150 being slidably received within distal control member 140, anchor delivery member 150 can be slidable within a lumen of outer shaft 120 (either the same lumen receiving inner shaft 130 and/or anchor delivery member 150 or a different lumen) or a lumen of inner shaft 130 (either the same lumen receiving distal control member 140 or a different lumen). In some embodiments, outer shaft 130 has a separate and distinct lumen for each of members 130, 140, and 150, and can be configured to deploy implant 102 around members 140 and 150.

Figure 2B:
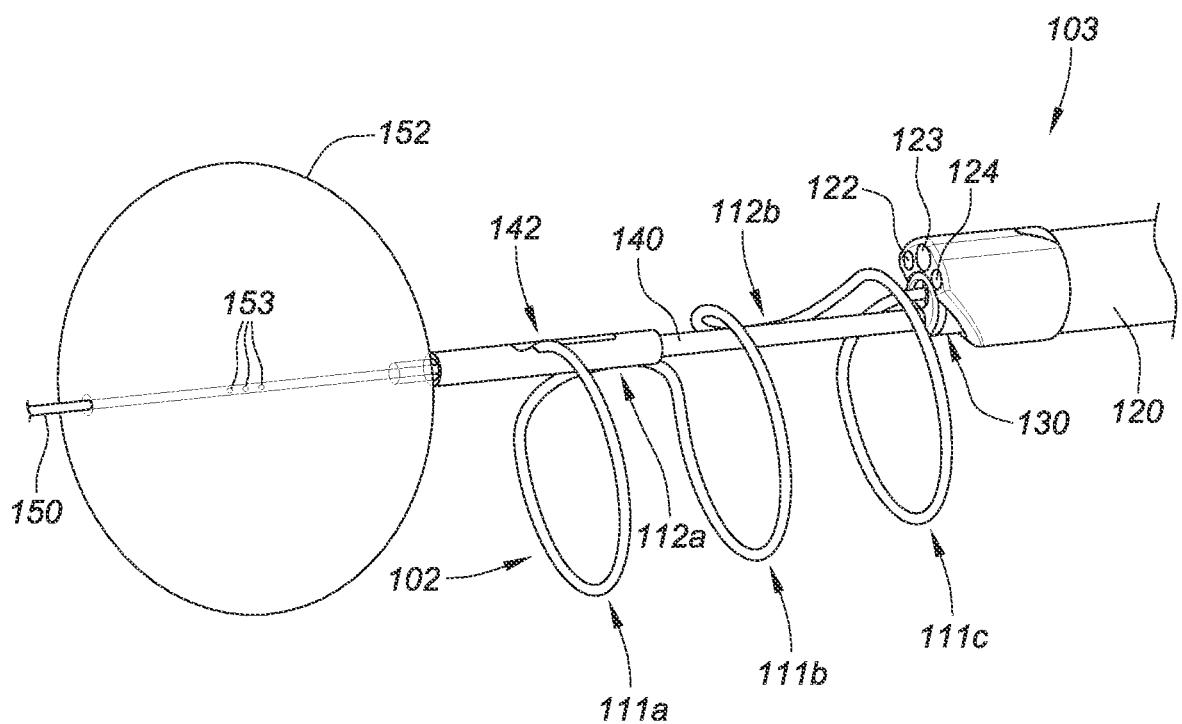

FIG. 2B is a perspective view depicting distal end region 104 of delivery device 103 with the various components deployed. In this embodiment, anchor delivery member 150 includes an anchor 152 in the form of an inflatable member or balloon. Other embodiments of anchors 152 are described with respect to FIGS. 4A-4G. Anchor 152 expands (or otherwise transitions) to a size greater than that of the bladder neck such that anchor 152 resists proximal retraction (e.g., a relatively light tension). In embodiments where anchor 152 is a balloon, that balloon can be elastic or inelastic and inflatable with an inflation medium (e.g., air or liquid such as saline) introduced into balloon 152 through one or more inflation ports 153. Here three inflation ports 153 are located on the shaft of anchor delivery member 150 and communicate with an inflation lumen that extends proximally back to proximal control device 200, which can include a port for inflation with a syringe. Upon deployment of anchor 152, the physician can proximally retract delivery system 100 until anchor 152 is in contact with the bladder neck and/or wall (if not already).

The physician can use the imaging device of outer shaft 120 to move delivery device 103 proximally away from anchor 152 until the physician is in the desired position within the urethra to begin deployment of implant 102. A retainer 142 on distal control member 140 is releasably coupled with distal engagement member 114 of implant 102. The physician can position retainer 142 in a location along the length of the urethra where the physician desires the distal end of implant 102 to deploy. This can involve moving distal control member 140 and inner shaft 130, together, proximally and/or distally with respect to anchor delivery member 150. In another embodiment, the position of retainer 142 is fixed with respect to anchor 152 such that the longitudinal position of implant 102 within the anatomy is set by the system independently of any manipulation by the physician. The coupling of distal engagement member 114 with retainer 142 also permits the physician to manipulate the radial orientation of implant 102 by rotating distal control member 140 and inner shaft 130 together. Active or passive shaping of distal control member 140 may allow for a more desirable placement of implant 102. For example, member 140 may have a curvature that places the implant in a more anterior anatomical position. This curvature may be inherently set in member 150 or actively applied by the physician though a separate entity such as a control wire. Once in the desired location and orientation, the physician can proximally retract inner shaft 130 with respect to distal control member 140 to initiate deployment of implant 102.

Distal engagement member 114 is held in place with respect to distal control member 140 by retainer 142, and proximal retraction of inner shaft 130 with respect to distal control member 140 causes ring-shaped structures 111 to begin to deploy in sequence (111a, then 111b, then 111c, then 111d (not shown)). Distal control member 140 can remain stationary or be moved longitudinally with respect to the urethra during deployment. In some embodiments, distal control member 140 is steerable to allow for angulation of implant 102 to accommodate relatively tortuous anatomy. Mechanisms for accomplishing steerability are discussed elsewhere herein and can likewise be applied to distal control member 140. In these or other embodiments, distal control member 140 can be significantly flexible to passively accommodate tortuous anatomy. In some embodiments, distal control member 140 has a predefined curve to assist in navigation.

To assist in deployment, inner shaft 130 can rotate clockwise and counterclockwise (as depicted by arrow 134) about distal control member 140. Referring back to FIGS. 1B-1C, implant 102 has a non-constant direction of winding that, when viewed as commencing at distal engagement member 114, proceeds clockwise along ring-shaped structure 111a, then reverses along interconnect 112a to a counterclockwise direction for ring-shaped structure 111b, then reverses along interconnect 112b to a clockwise direction for ring-shaped structure 111c, and then reverses along interconnect 112c to a counterclockwise direction for ring-shaped structure 111d, until ending at proximal engagement member 115. Depending on the direction of winding of the portion of implant 102 about to exit the open distal terminus of lumen 131, the transition of implant 102 towards the at-rest configuration can impart a torque on shaft 130 if shaft 130 is not actively rotated as implant 102 is deployed. That torque can cause shaft 130 to passively rotate (without user intervention) either clockwise or counterclockwise accordingly. In certain embodiments described elsewhere herein, shaft 130 is actively rotated during deployment. Rotation of inner shaft 130 with respect to distal control member 140 thus allows delivery device 103 to rotate and follow the direction of winding of implant 102. In some embodiments, all ring-shaped structures 111 are wound in the same direction, clockwise or counterclockwise (e.g., as in the case of a fully spiral or helical implant), or do not have a set direction of winding.

In this or other embodiments, the distal end region of inner shaft 130 is configured to be relatively more flexible than the more proximal portion of inner shaft 130, which can permit avoidance of excessive motion of the rest of device 103 during deployment, resulting in better visualization and less tissue contact by device 103. Such a configuration can also reduce the stress imparted on implant 102 by device 103 during delivery. For example, the portion of inner shaft 130 extending from outer shaft 120 during deployment can be relatively more flexible than the portion of inner shaft 130 that remains within outer shaft 120, thus allowing inner shaft 130 to flex more readily as implant 102 exits inner lumen 131. This in turn can stabilize delivery device 103 and allow the physician to obtain stable images of the appointment process.

FIG. 2B depicts implant 102 after three ring-shaped structures 111a, 111b, and 111c have been deployed. Proximal retraction of shaft 130 continues until the entirety of implant 102, or at least all of ring-shaped structures 111, have exited lumen 131. If the physician is satisfied with the deployed position of implant 102 and the deployed shape of implant 102, then implant 102 can be released from delivery device 103.

Release of the distal end of implant 102 can be accomplished by releasing retainer 142. Retainer 142 can be a cylindrical structure or other sleeve that linearly or rotationally actuates over a cavity or recess in which a portion of implant 102 is housed. In the embodiment of FIG. 2B, retainer 142 includes an opening or slot that allows distal engagement member 114 to pass therethrough. Retainer 142 can rotate with respect to the cavity or recess in which distal engagement member 114 (not shown) is housed until the opening or slot is positioned over member 114, at which point member 114 is free to release from distal control member 130. Rotation of retainer 142 can be accomplished by rotation of a rotatable shaft, rod or other member coupled with retainer 142 (and accessible at proximal control device 200).

Figure 2C:
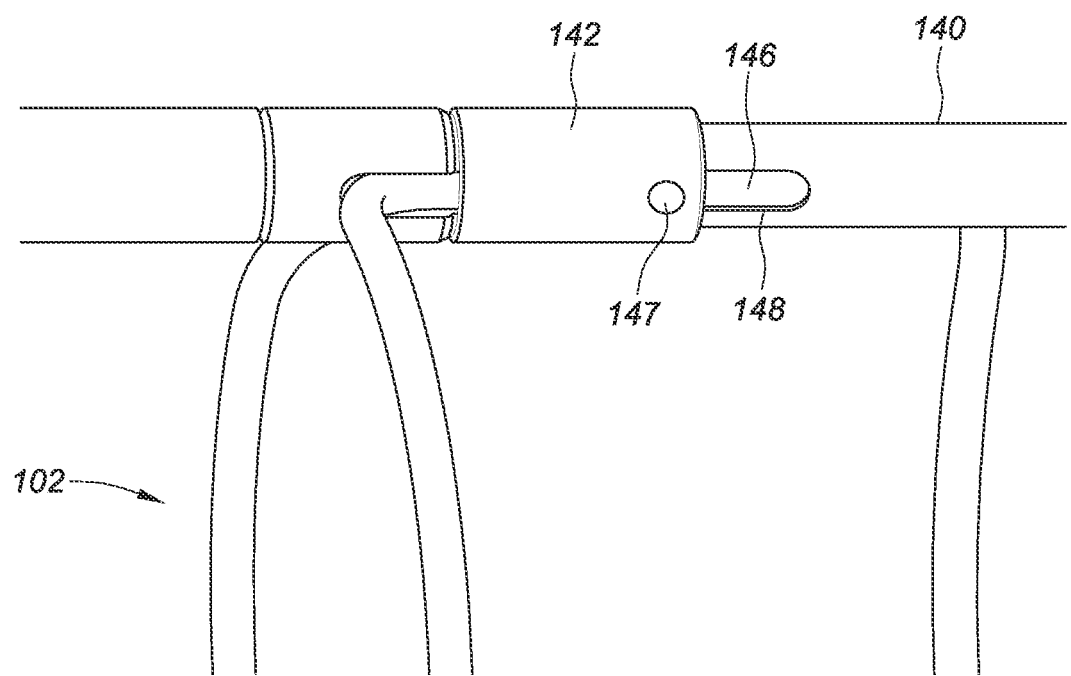
Figure 2D:
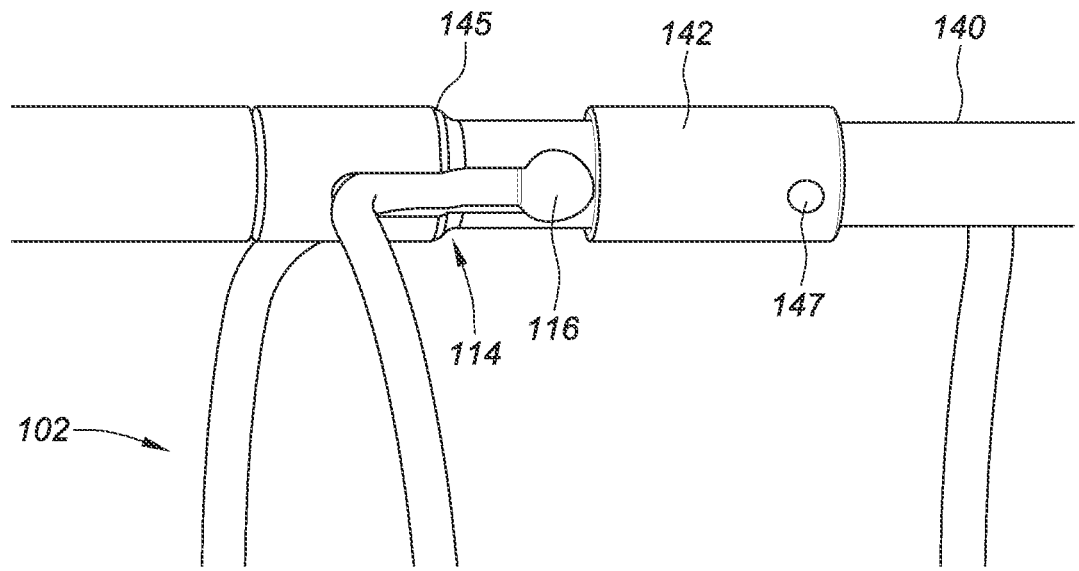

FIGS. 2C and 2D are perspective views depicting another example embodiment of system 100 with a different embodiment of retainer 142 shown in more detail. Here, retainer 142 slides distally and/or proximally with respect to distal control member 140. Distal engagement member 114 of implant 102 can be received within a corresponding recess of distal control member 140. Retainer 142 can slide over distal engagement member 114 while received within this recess until retainer 142 abuts a stepped portion of member 140. A control wire 146 extends within the length of control member 140, either in the same lumen as anchor delivery member 150 or in a different lumen. Control wire 146 couples with retainer 142 with an enlarged portion 147 from which control wire 146 can be routed into member 140 through an opening 148.

Figure 2E:
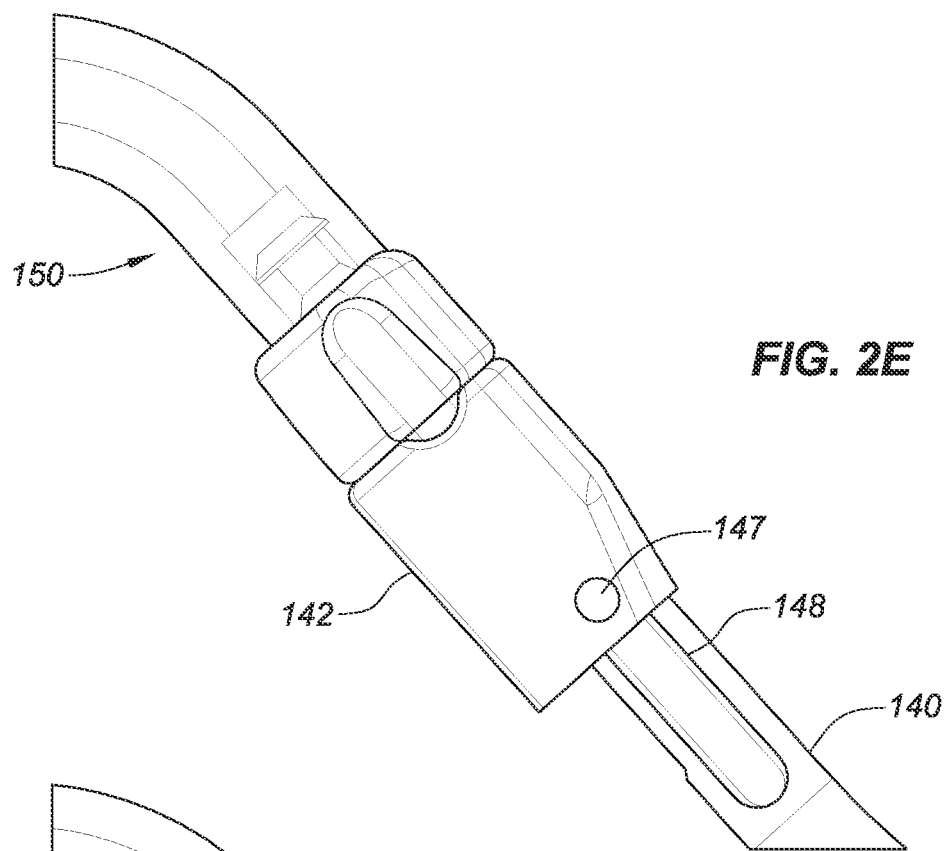
Figure 2F:
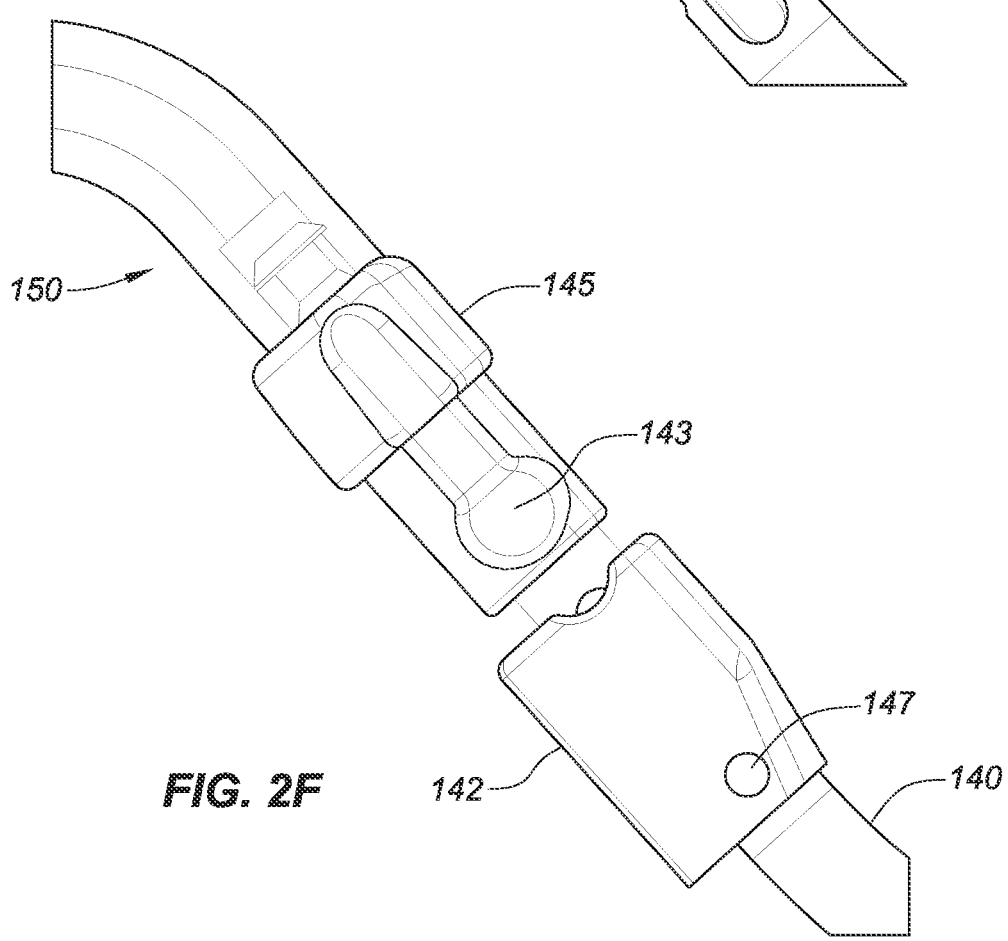

Engagement member 114 can be placed within the recess and retainer 142 can be advanced over engagement 114 to secure the distal end of implant 102 to control member 140. Upon satisfactory deployment of implant 102 within the urethra, e.g., in the state of FIG. 2C, retainer 142 can be proximally retracted with control wire 146 to expose engagement member 114 and permit its release from member 140. FIGS. 2E and 2F are perspective views depicting another embodiment of system 100 with another configuration for retainer 142 that operates in similar fashion to that described with respect to FIGS. 2C and 2D. Here, implant 102 is not shown and recess 143 in which distal engagement member 114 can be received is shown in more detail.

Figure 2G:
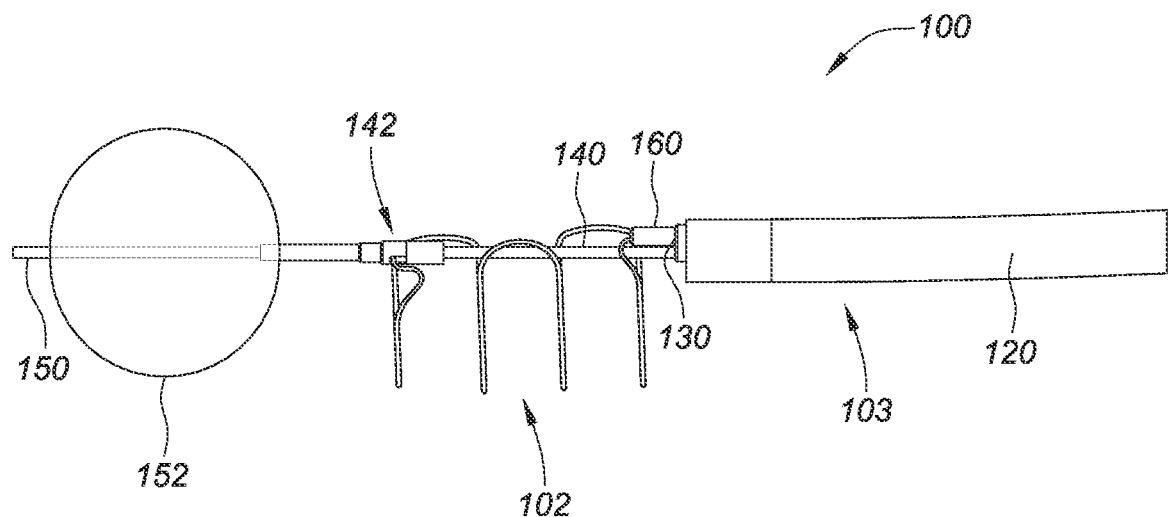
Figure 2H:
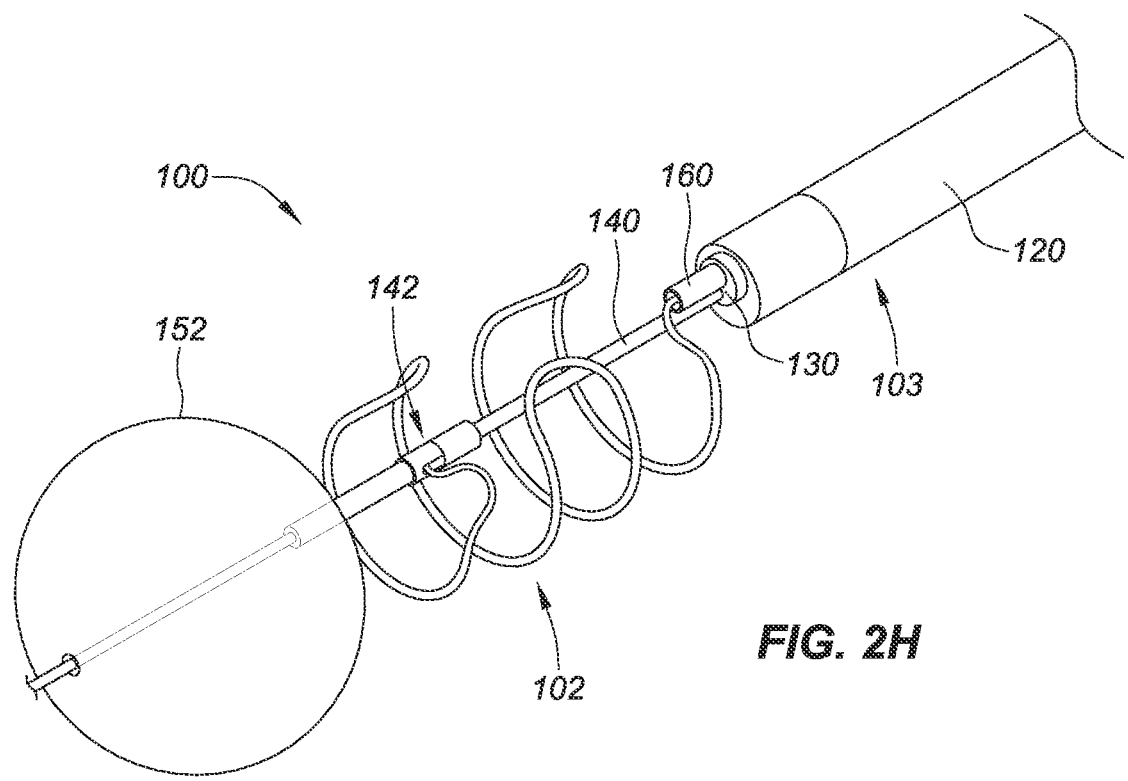

FIGS. 2G and 2H are side and perspective views, respectively, of another example embodiment of system 100. In this embodiment, inner shaft 130 includes a flexible distal extension 160 in which inner lumen 131 (not shown) is located. In this configuration, the open distal terminus of lumen 131 is located distal to the open distal terminus of lumen 132 (not shown) from which distal control member 140 extends. Lumens 122, 123, and 124 (not shown) are located on outer shaft 120 opposite to distal extension 160. Flexible distal extension 160 contributes to the flexibility to stabilize the delivery system, as well as to stabilize the image. Flexible extension 160 helps align ring-shaped structures 111 in a planar manner, and helps vector implant 102 (e.g., point radially) toward the urethral wall during deployment.

Figure 3A:
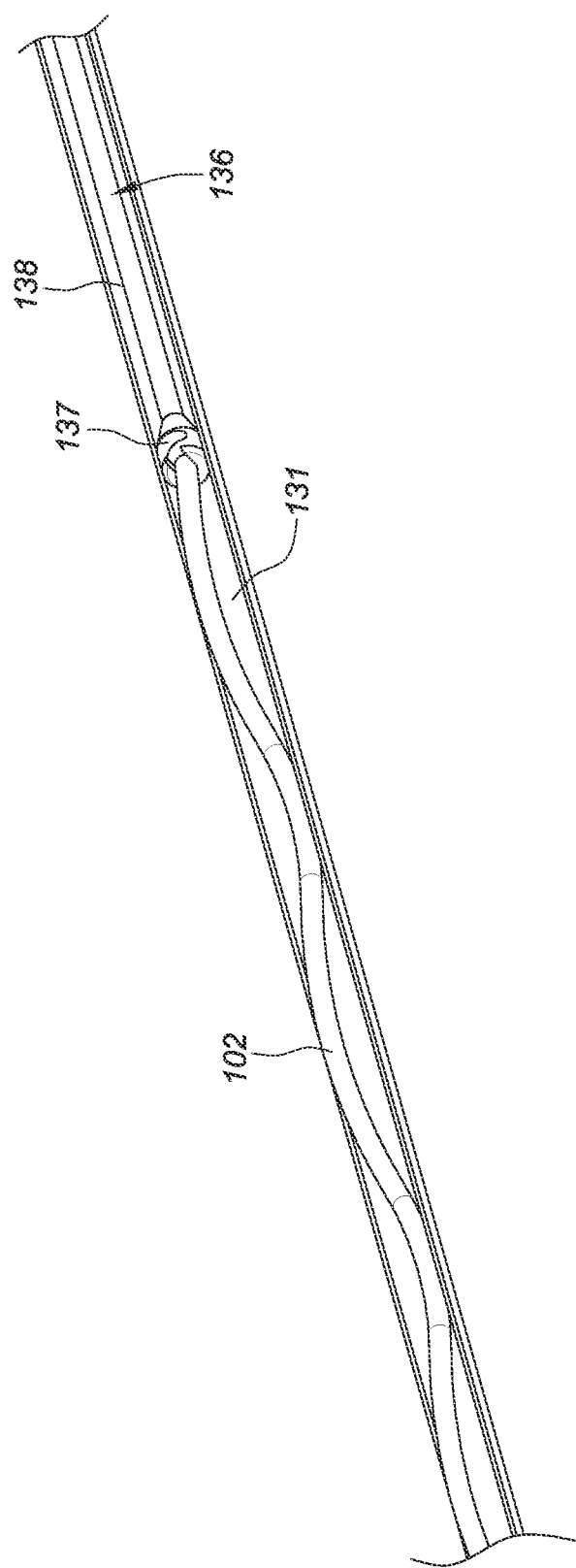
FIGS. 3A-3C are perspective views depicting example embodiments of a grasper component in use within a delivery system.

Release of the proximal end of implant 102 is also controllable. FIG. 3A is a partial cross-sectional view depicting an example embodiment of system 100 with a portion of implant 102 shown within inner lumen 131 of inner shaft 130. Here, implant 102 is in the lineated state prior to deployment with proximal engagement member 115 coupled with a grasper 136 that is slidable distally and/or proximally within lumen 131. Grasper 136 can include a distal end region 137 on or coupled with a shaft 138. Grasper 136 is preferably controllable to rotate and longitudinally translate (e.g., push and pull) implant 102 with respect to inner shaft 130.

Figure 3B:
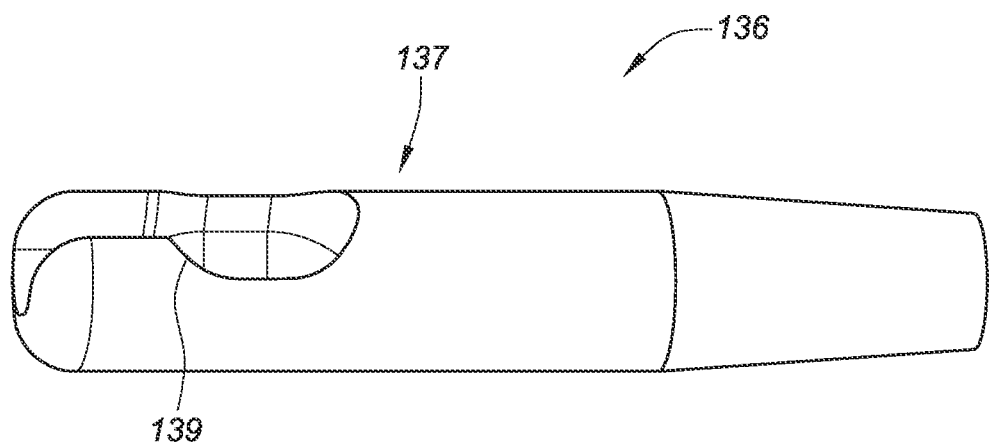
Figure 3C:
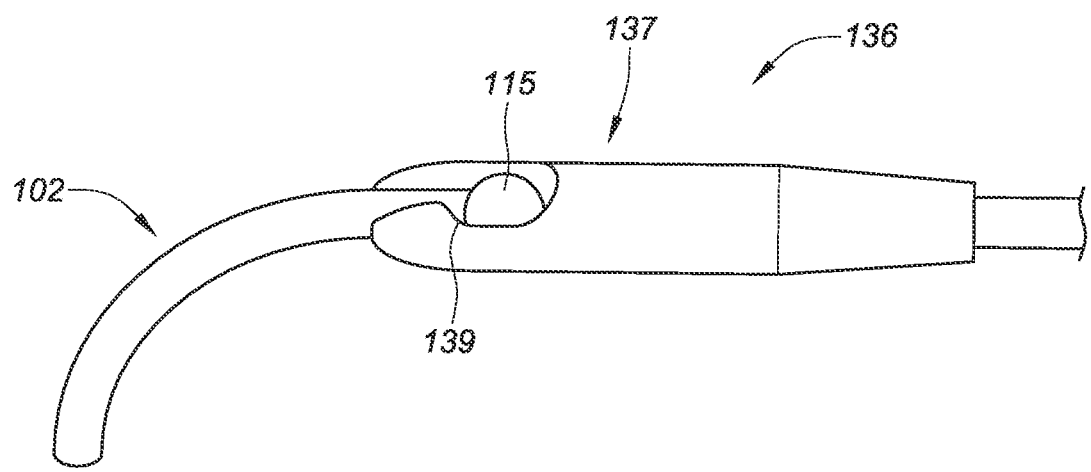

FIGS. 3B and 3C are perspective views depicting an example embodiment of distal end region 137 of grasper 136 without implant 102 and with implant 102, respectively. Grasper 136 includes a recess (also referred to as a cavity or pocket) 139 for receiving and holding proximal engagement member 115. Here, the enlarged portion 117 is retained within recess 139 by a distal necked down region having a relatively smaller width. While within inner lumen 131, the sidewalls of inner shaft 130 maintain proximal engagement member 115 within recess 139. When distal end region 137 exits inner lumen 131 (either by retracting inner shaft 130 with respect to grasper 136 or by advancing grasper 136 with respect to inner shaft 130), the restraint imparted by the inner shaft sidewalls is no longer present and engagement member 115 is free to release from grasper 136. Thus, when the physician is satisfied with placement of the deployed implant 102, distal engagement member 114 can be released by moving retainer 142 and permitting distal engagement member 114 to decouple from control member 140, and proximal engagement member 115 can be released by exposing grasper 136 from within inner shaft 130 and permitting proximal engagement member 115 to decouple from grasper 136.

Grasper 136 can also assist in loading implant 102. In some embodiments, application of a tensile force on implant 102 with grasper 136 (while the opposite end of implant 102 is secured, for example, by retainer 142) facilitates the transition of implant 102 from the at-rest configuration to a lineated configuration suitable for insertion of implant 102 into inner shaft 130.

Figure 4A:
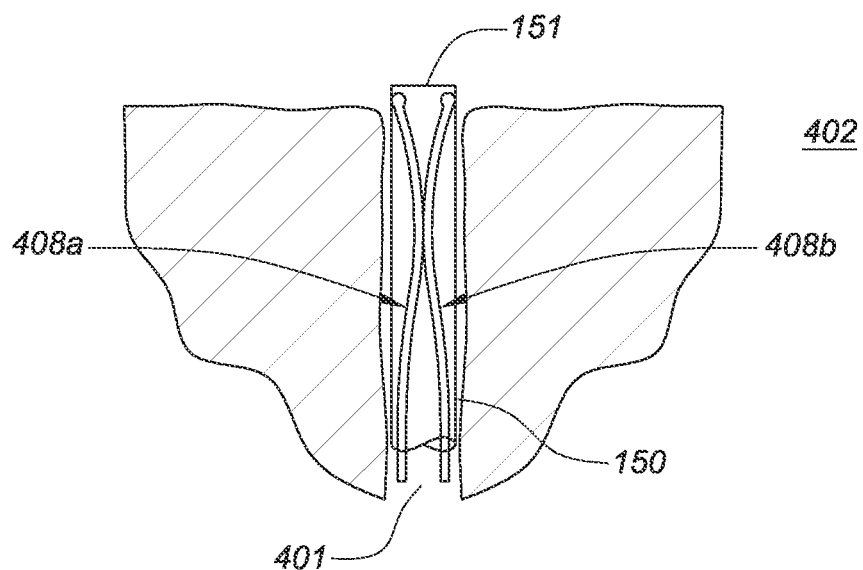
FIGS. 4A-4J are partial cross-sectional views depicting example embodiments of anchor delivery members of a delivery system.
Figure 4B:
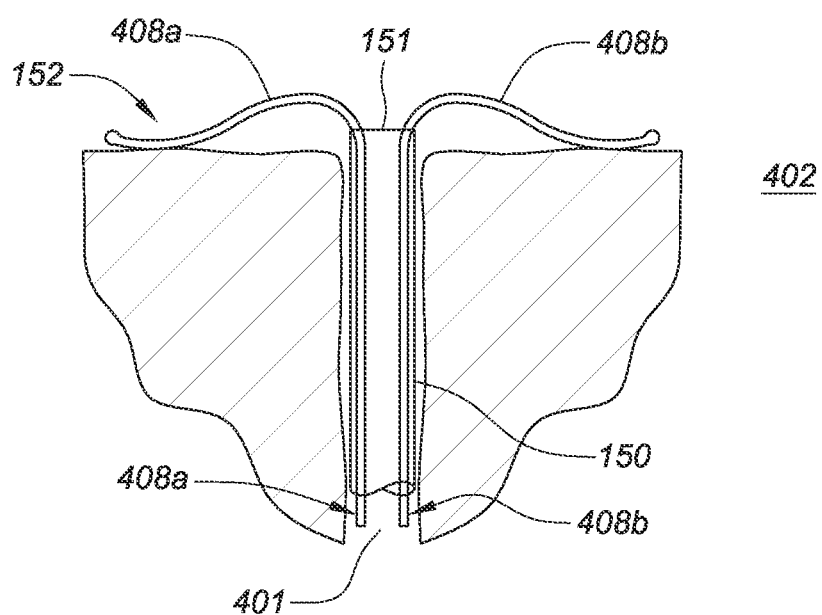

Anchor delivery member 150 can have multiple different configurations and geometries (e.g., including those that extend in one direction across the bladder wall, two directions across the bladder wall (e.g., left and right), or three or more directions across the bladder wall). FIGS. 4A-4B are cross-sectional views depicting an example embodiment of anchor delivery member 150 in various stages of deployment within a patient's body. In FIG. 4A, anchor delivery member 150 has been advanced through urethra 401 until open distal end 151 is past the bladder neck and within bladder 402, although in this and other embodiments end 401 can be stopped prior to entering bladder 402. Here, two anchoring arms 408a and 408b are housed within an inner lumen of anchor delivery member 150. In other embodiments, anchoring arms 408 can each be housed in a separate lumen within member 150. Anchoring arms 408 can be distally advanced with respect to anchor delivery member 150 (or anchor delivery member 150 can be advanced into bladder 402 and proximally retracted with respect to anchoring arms 408) such that upon exiting open distal end 151, deflectable portions 410a and 410b transition laterally into contact with the bladder wall forming anchor 152 as depicted in FIG. 4B.

Figure 4C:
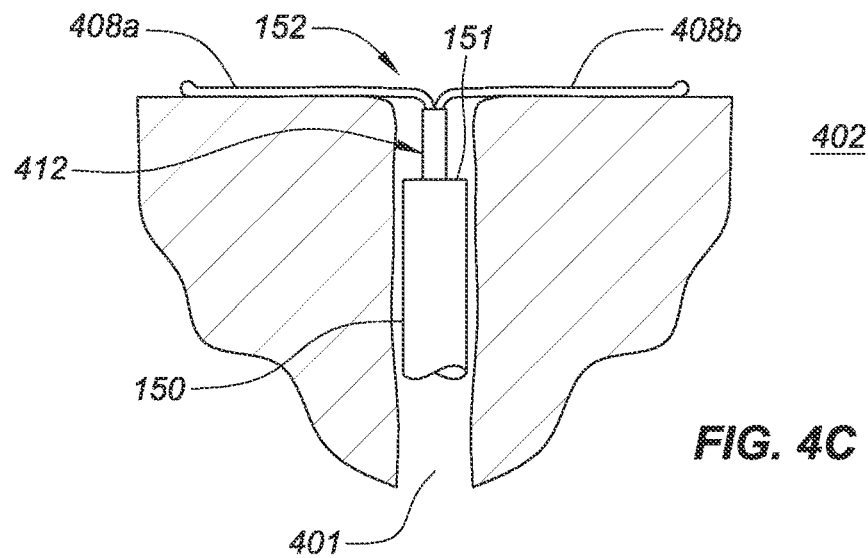

Anchoring arms 408 can be formed of a shape retentive material that is biased towards the at-rest configuration of FIG. 4B. The distal ends of anchoring arms 408 can each have an atraumatic terminus as depicted here (e.g., rounded, spherical, ballized) and, or alternatively, the distal ends of arms 408 can curve away from the bladder wall for added atraumatic effect. In other embodiments, only one anchoring arm 408 is used. FIG. 4C is a cross-sectional view depicting another example embodiment of anchor delivery member 150. Here, deflectable portions 410a and 410b have a generally straight or lineated shape and deflect from a shared shaft 412 that is slidable distally and/or proximally with respect to anchor delivery member 150. In all of the anchoring embodiments described herein, the one or more deflectable portions can deflect from a shared shaft (such as depicted here) or from separate shafts (such as depicted in FIGS. 4A-4B).

Figure 4D:
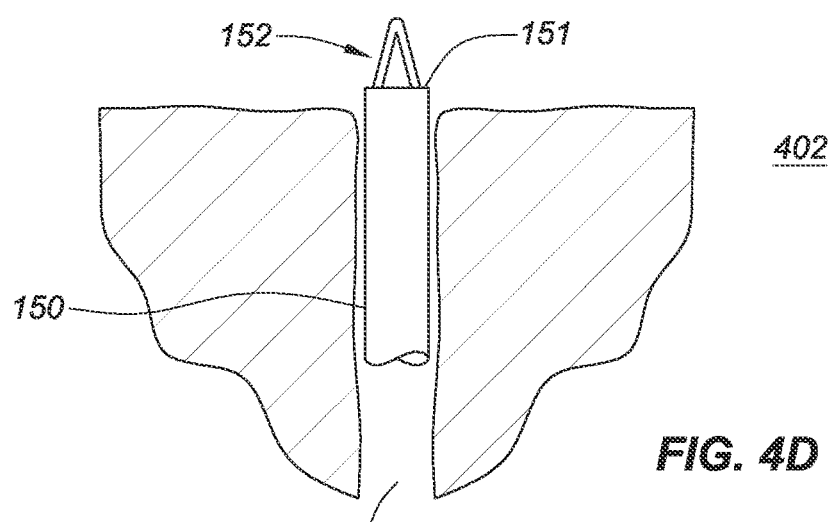
Figure 4E:
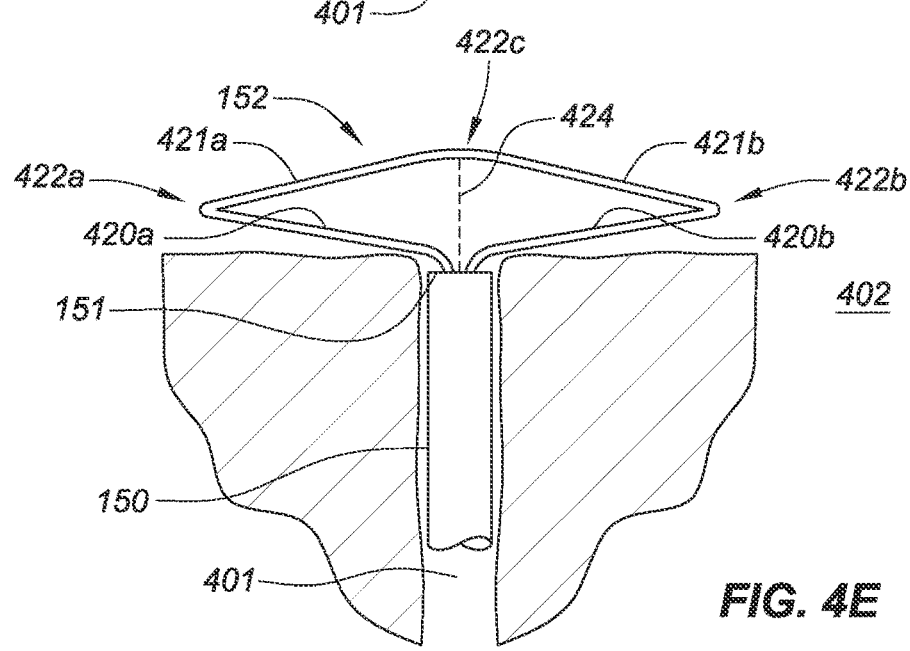

FIGS. 4D-4E are partial cross-sectional views depicting another example embodiment of anchor delivery member 150. FIG. 4D depicts this embodiment with anchor 152 in a state of partial deployment from open distal end 151 of anchor delivery member 150. FIG. 4E depicts anchor 152 after full deployment within bladder 402. Here, anchor 152 includes laterally deflectable struts 420a, 420b, 421a, and 421b connected by hinges 422a, 422b, and 422c. Specifically, laterally deflectable struts 420a and 421a are connected by hinge 422a, laterally deflectable struts 420b and 421b are connected by hinge 422b, and struts 421a and 421b are connected by hinge 422c. Again, anchor 152 is biased towards the at-rest configuration depicted in FIG. 4E and automatically transitions towards this configuration once exposed from within the inner lumen of anchor delivery member 150. Hinges 422 can each be implemented as a living hinge such as depicted in FIG. 4E, e.g., defined by a reduced with or relatively more flexible section of the device. Other hinge configurations can also be utilized.

In another embodiment, a pull wire or other member 424 is attached to one or more of struts 421 and/or hinge 422c and extends proximally to proximal control device 200. In FIG. 4E, pull member 424 is shown with a dashed line to indicate that it is optional. Proximal retraction of pull member 424 at proximal control device 200 causes the structural arrangement to laterally deflect into the configuration depicted in FIG. 4E. This arrangement provides a significant locking force while tension is maintained on pull member 424.

Figure 4F:
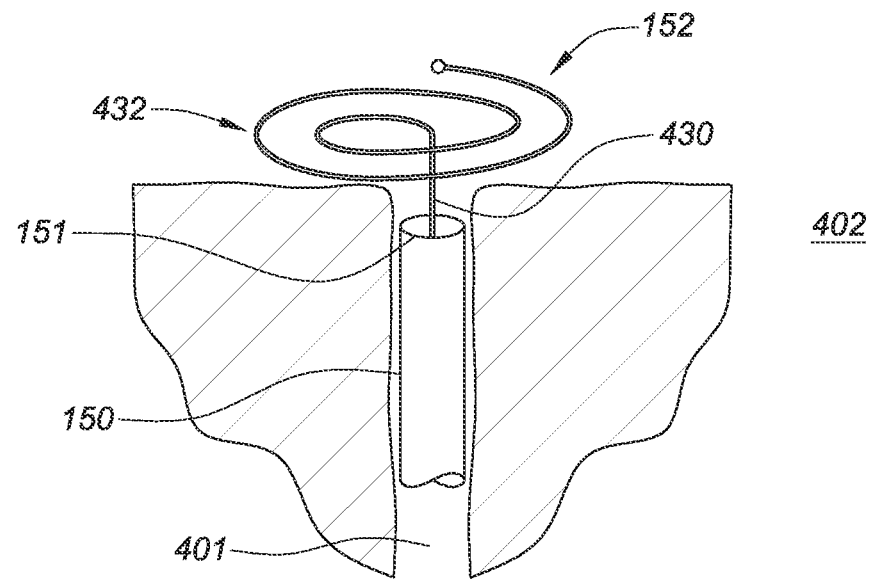
Figure 4G:
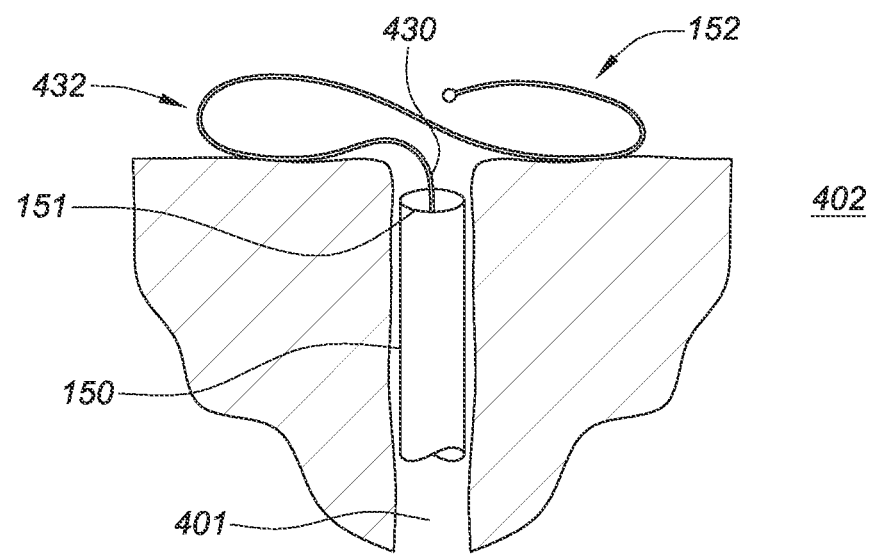

FIG. 4F is a partial cross-sectional view depicting another example embodiment of anchor delivery member 150. Here, a shape retentive element 430 has been advanced from within the inner lumen of anchor delivery member 150 where it was in a relatively straight or lineated shape. Upon exiting open distal end 151, the distal portion of element 430 automatically transitions towards a laterally expanded shape 432, which in this embodiment is in the shape of a coil or spiral. FIG. 4G depicts another example embodiment where the laterally expanded shape 432 has multiple loops and resembles a numeral "8" or a bowtie. Many different shapes can be utilized for laterally expanded shape 432 in addition to those depicted here. In all of the anchoring embodiments, the distal termini of the wires or elements exposed to the body tissue can have a rounded or enlarged atraumatic end (as depicted in FIGS. 4F and 4G).

Upon completion of the implant deployment procedure, anchor 152 can be collapsed or retracted to permit removal of delivery device 103. For instance, in embodiments where anchor 152 is a balloon, that balloon is deflated and optionally retracted back into a lumen of device 103, and subsequently withdrawn from the bladder and urethra. In embodiments where anchor 152 is a wire form or other expandable member (such as those described with respect to FIGS. 4A-4G), anchor 152 is retracted back into the lumen of device 103 from which it was deployed, and device 103 can subsequently be withdrawn from the bladder and urethra. Retraction can be accomplished using fluid or pneumatic actuation, a screw type mechanism, or others.

Figure 4H:
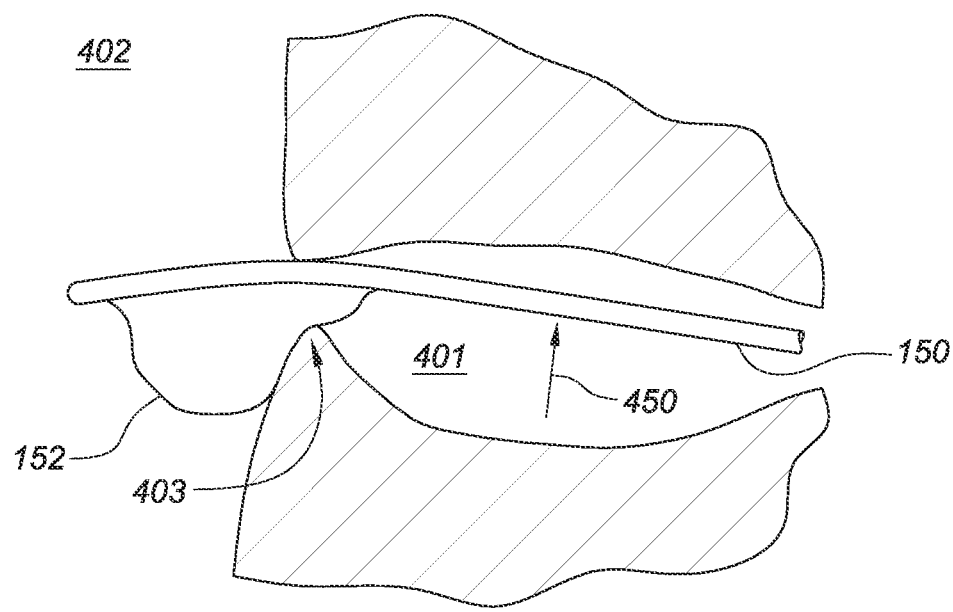

In FIG. 2B, anchor 152 is a generally spherical balloon with anchor delivery member 150 extending through the center. In other embodiments, balloon anchor 152 can be laterally offset, or positioned on only one side of anchor delivery member 150. FIG. 4H is a partial cross-sectional view depicting an example embodiment having a laterally offset balloon 152. Here the laterally offset balloon 152 exerts force on the side of bladder neck 403, and forces anchor delivery member 150 (and delivery device 103) in direction 450.

Figure 4I:
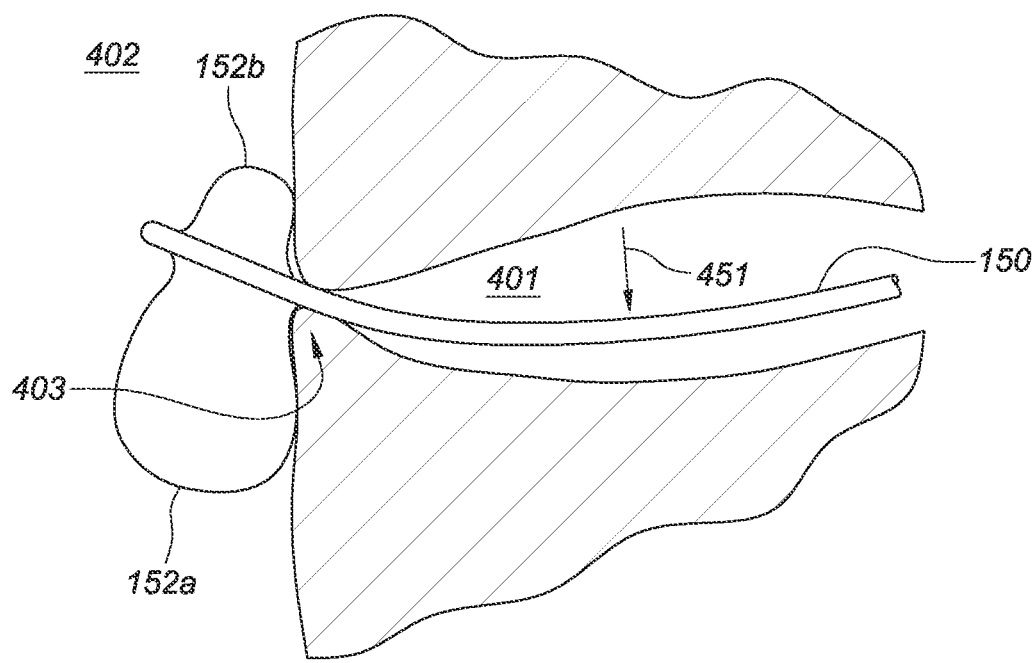

In other embodiments device 103 can include two or more balloons that can independently inflate in different lateral directions. Independent inflation of one or more balloons while maintaining the one or more remaining balloons in a deflated state can allow the user to change the angle of the delivery catheter relative to the anatomy, and thus allow for deployment of the implant in anatomy with significant curvatures. FIG. 4I depicts another example embodiment where a first anchor balloon 152a is inflated to a larger size than a second anchor balloon 152b located on the opposite side of member 150. As a result of the forces exerted on the bladder wall, member 150 is tilted away from the smaller balloon 152b in direction 451. Selection of the appropriate balloon or balloons for inflation can be performed by the physician and the process of inflation and deflation can be repeated until the physician achieves a desirable angular orientation of device 103 within the anatomy, at which point the rest of the delivery procedure can be performed. Delivery member 150 can be a flexible or rigid shaft pre-shaped in a manner which will not impede the ability of implant 102 to be placed in a desirable anatomical position. For example, curvature in member 150 just proximal to the balloon mount location may allow implant 102 to be placed more anteriorly without constraint from the bladder neck.

Figure 4J:
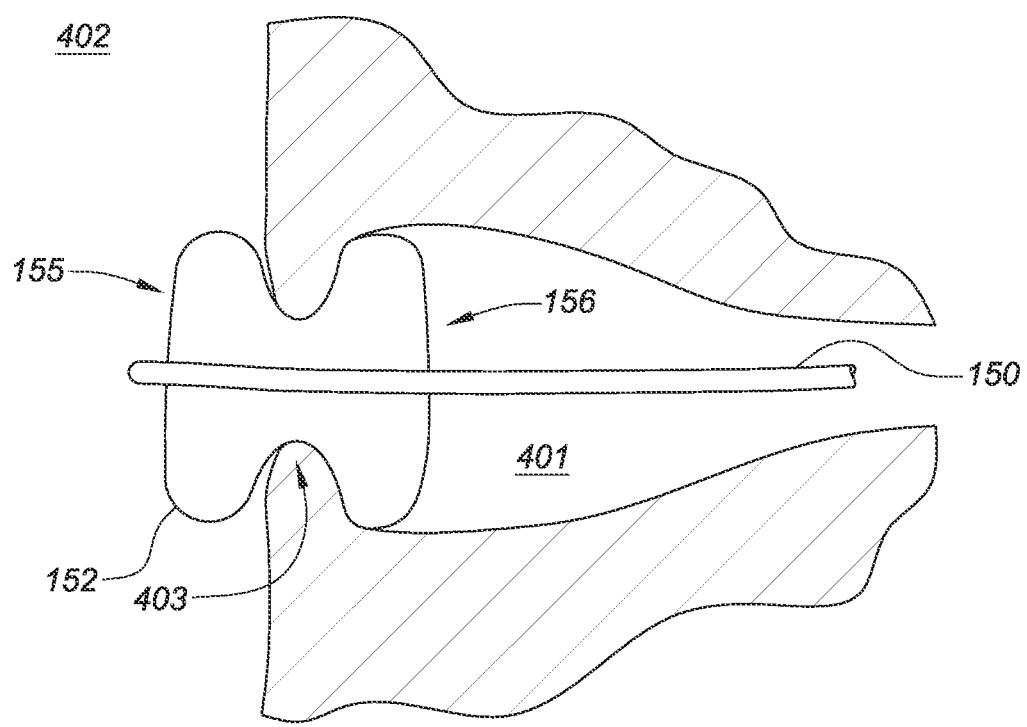

In some embodiments, a shaped balloon or substantially elastic balloon can be inflated at the same location as the bladder neck. FIG. 4J depicts an example embodiment where balloon 152 is inflated at bladder neck 403. Here, balloon 152 includes a first lobe 155 formed in bladder 402 and a second lobe 156 formed in urethra 401. This configuration can be used to anchor member 150 directly over bladder neck 403.

Example Embodiments of Proximal Control Devices and Related Methods

FIG. 5A is a side view depicting an example embodiment of delivery system 100 prior to deployment of implant 102, and FIG. 5B is a side view depicting this embodiment with implant 102 in a deployed configuration (anchor delivery member 150 and distal control member 140 are not shown). In this embodiment proximal control device 200 is a handheld device having a handle 201, a user actuator 202 (configured in this example as a trigger), and a main body 203. A longitudinal axis of delivery device 103 is indicated by dashed line 204. Proximal control device 200 can include mechanisms that are manually powered by actuation of actuator 202 to cause relative motions of the components of device 103. In other embodiments, proximal control device 200 can utilize electrically powered mechanisms instead.

Figure 6A:
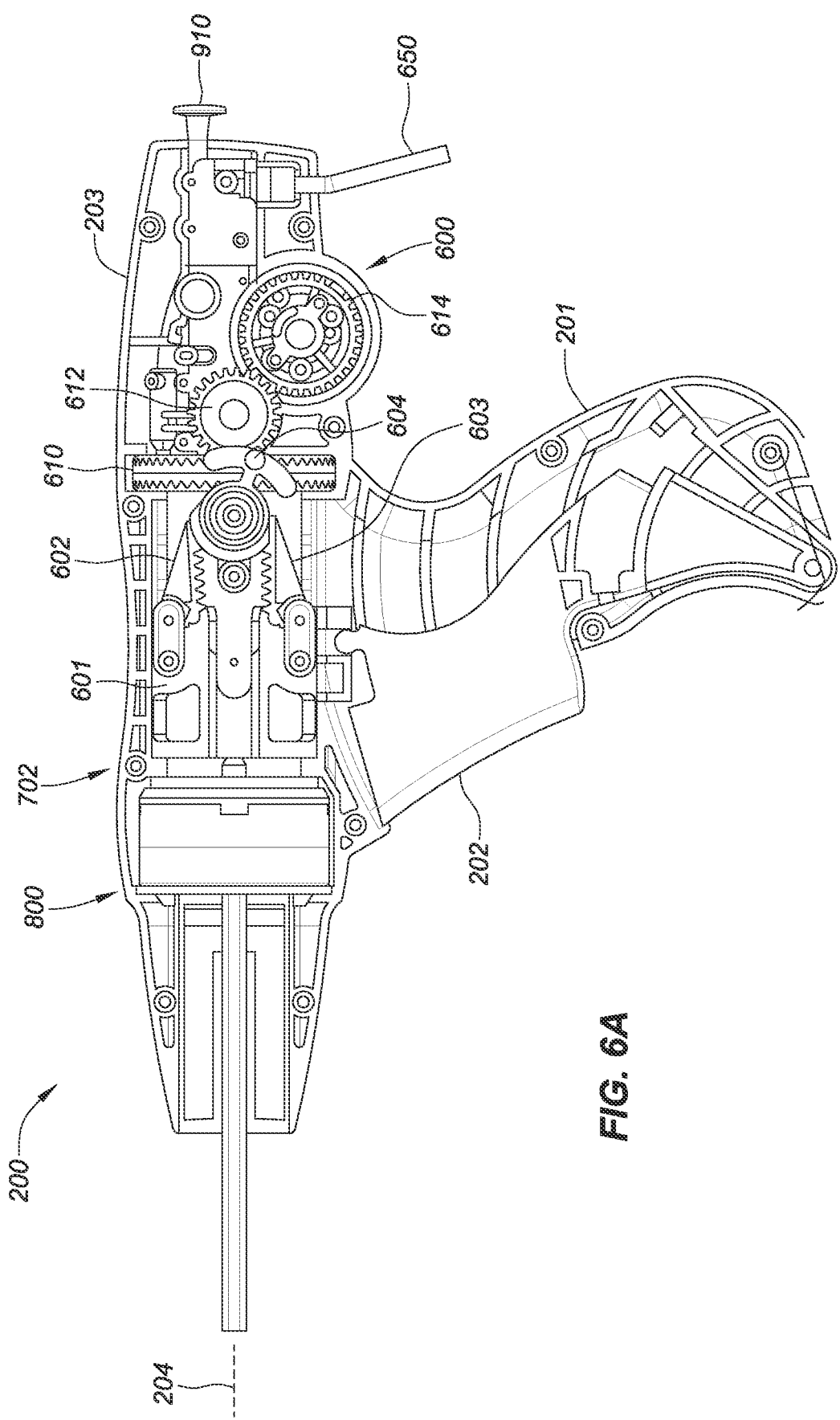
FIGS. 6A and 6B are interior side and interior perspective views, respectively, depicting an example embodiment of a proximal control device.

FIG. 6A is an interior view of proximal control device 200 that depicts various mechanical assemblies or subassemblies within a main housing 203 of control device 200. In this embodiment, proximal control device 200 is configured to perform three types of motion on implant 102, namely, distal advancement of implant 102 along axis 204 (e.g., pushing), proximal retraction of implant 102 and/or inner shaft 130 along axis 204 (e.g., pulling), and rotation of inner shaft 130 about axis 204 (e.g., rotation). In other embodiments, depending on the delivery functions desired, proximal control device 200 can be configured to perform any subset of one or two of the aforementioned types of motion, to perform these types of motion but imparted on different components, or to perform other types of motion not mentioned here.

In this embodiment, proximal control device 200 includes a longitudinally translatable member 601 that, in this embodiment, is configured as a yoke. Yoke 601 is coupled with trigger 202 such that depression of trigger 202 causes proximal longitudinal translation of yoke 601. Yoke 601 is coupled with two proximally-located ratchet members 602 and 603 that, in this embodiment, are configured as pawls. Pawl 602 has a set of teeth that oppose corresponding teeth on pawl 603, and the teeth of each pawl 602 and 603 can interface or engage with complementary teeth on a gear 605 (see FIG. 6B), referred to herein as a pinion gear, that is part of a first gear assembly 600.

A switch 604 is accessible to the user and can be shifted between two positions, where each position is responsible for bringing only one of pawls 602 and 603 into engagement with pinion gear 605. Each of pawls 602 and 603 are deflectable and biased (e.g., with the spring) towards engagement with pinion gear 605. In this embodiment, placement of switch 604 in a downward position moves pawl 602 out of engagement with pinion gear 605 and moves pawl 603 into engagement with pinion gear 605. The proximal movement of yoke 601 and pawl 603 causes pinion gear 605 to rotate counterclockwise. Placement of switch 604 in an upward position reverses the engagement and places pawl 602 into engagement with pinion gear 605 and the proximal movement of yoke 601 and pawl 602 causes pinion gear 605 to rotate clockwise.

In this embodiment, first gear assembly 600 includes pinion gear 605, a second gear 610, a third gear 612, and a fourth gear 614. In other embodiments, first gear assembly 600 can be implemented to achieve the same or similar functionality with more or less gears than those described here.

Pinion gear 605 is engaged with second gear 610, which is oriented perpendicular to pinion gear 605. Pinion gear 605 has teeth that project from the radial edge of gear 605 while the second gear 610 has teeth that project from both distal face and a proximal face of the gear 610, which is referred to herein as face gear 610. Counterclockwise rotation of pinion gear 605 will cause rotation of face gear 610 in a first direction and clockwise rotation of pinion gear 605 will cause rotation of face gear 610 in a second, opposite direction. The direction of rotation of face gear 610 in turn determines whether implant 102 is proximally retracted or distally advanced with respect to housing 203.

Figure 6B:
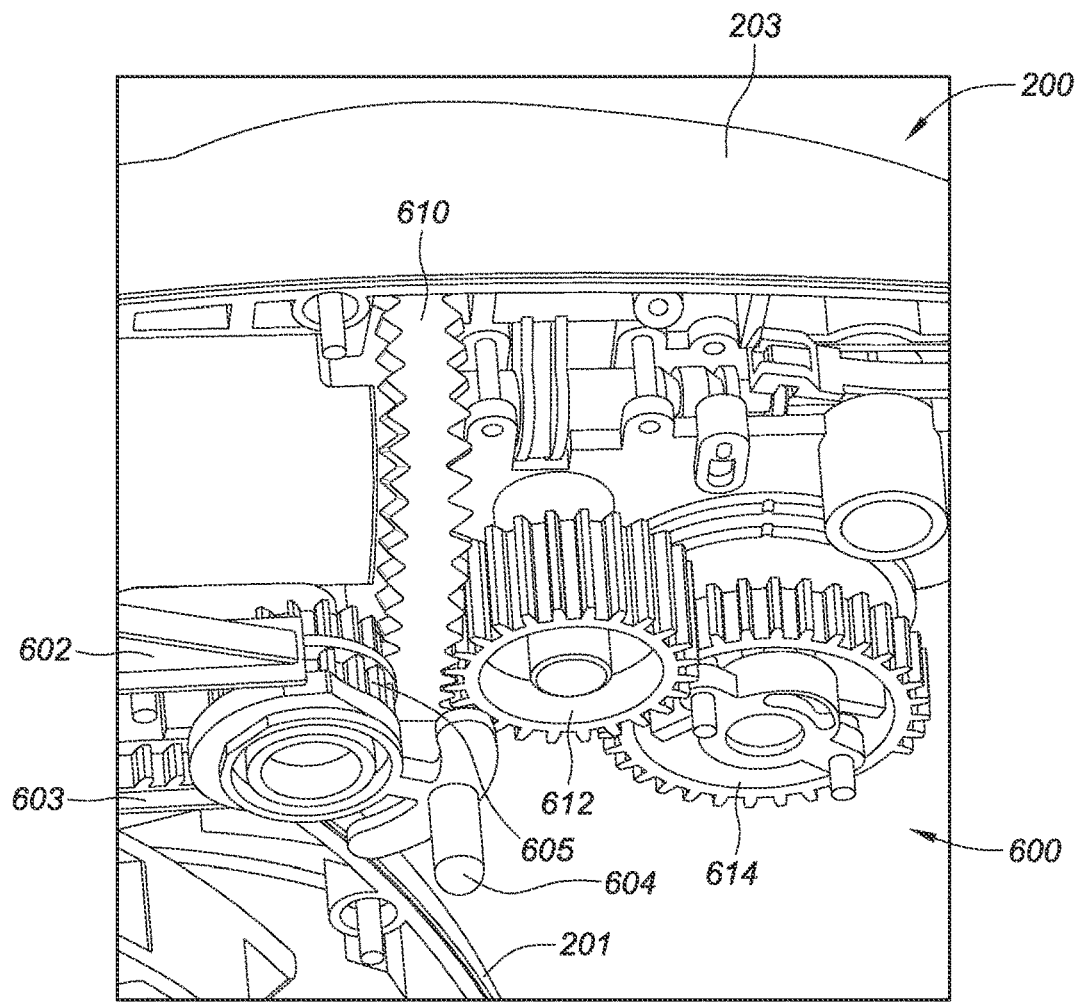
Figure 9A:
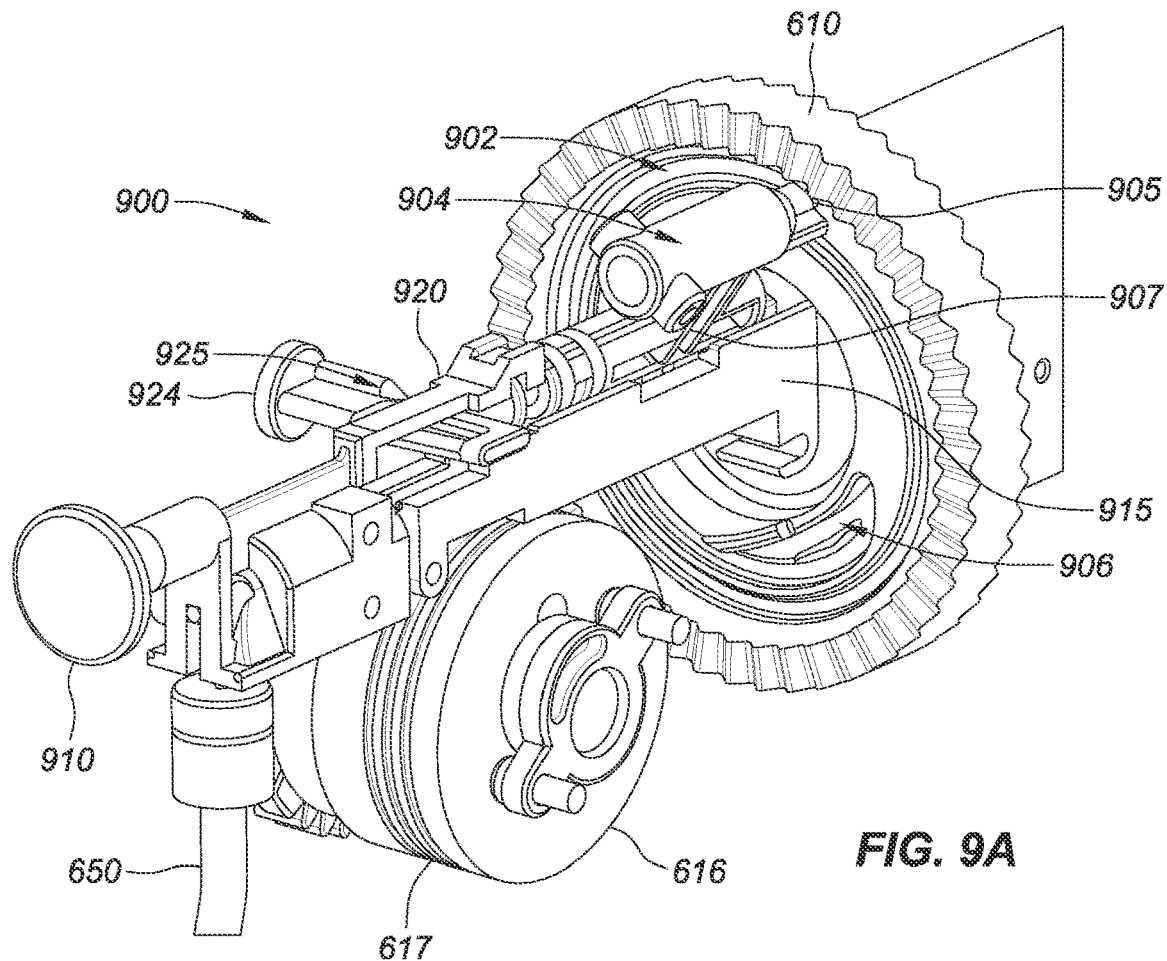
FIGS. 9A-9F are interior perspective views depicting an example embodiment of components of a proximal control device.
Figure 9B:
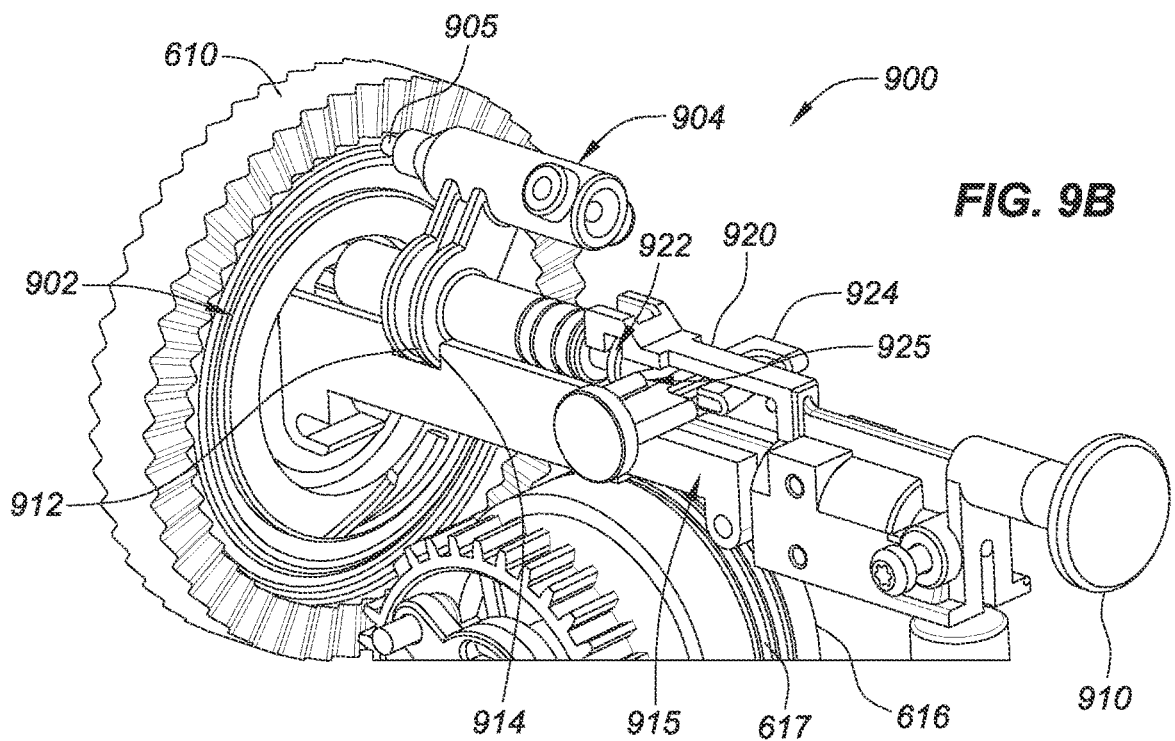
Figure 9C:
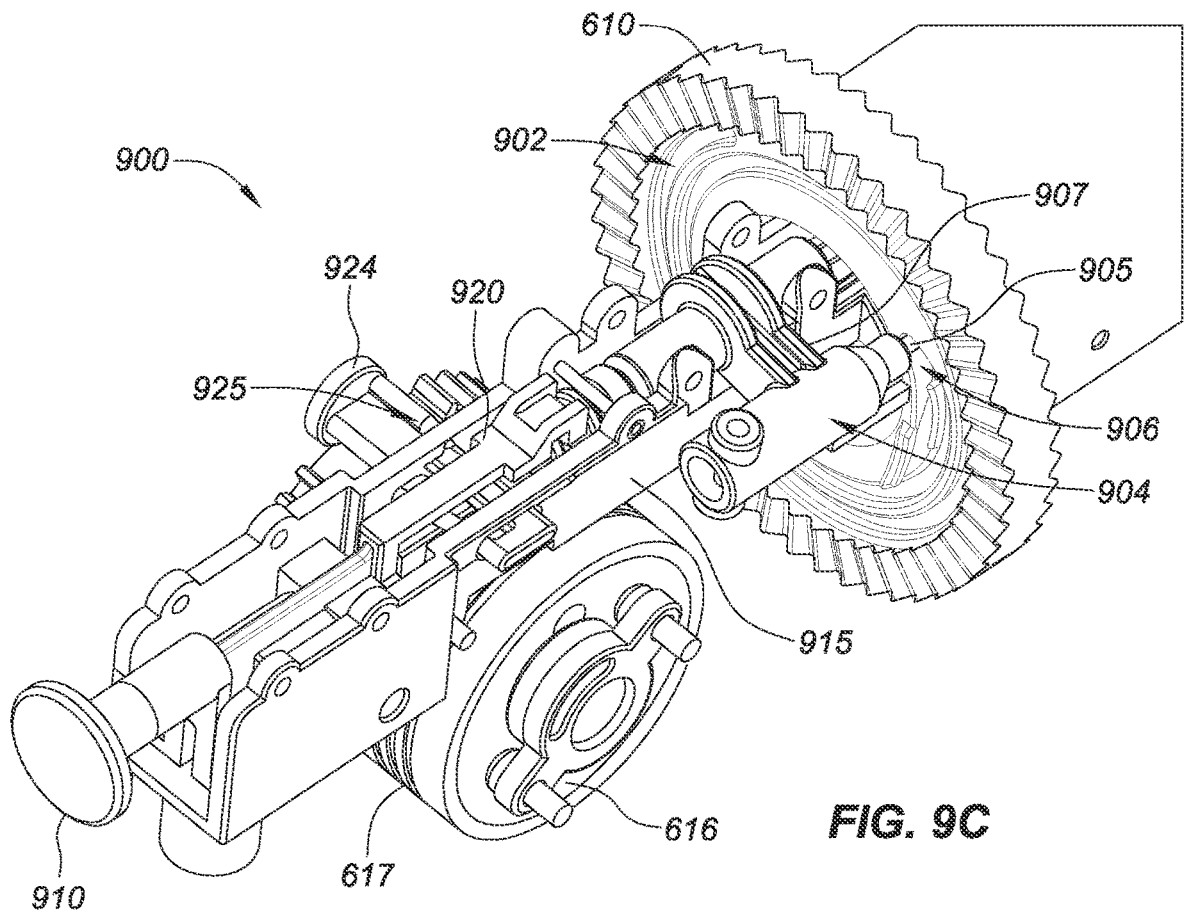

FIG. 6B is a perspective view depicting the interior of this embodiment of proximal control device 200 in more detail. The proximally facing teeth on face gear 610 engage with teeth on gear 612, referred to as an input gear. The teeth of input gear 612 are engaged with teeth of gear 614. Gear 614 is coupled with, or integrated with, a reel 616 that is configured to house or hold grasper shaft 138. As can be seen in the embodiment of FIGS. 9A-9B, reel 616 can include an optional groove or channel 617 in which grasper shaft 138 can be received. Rotation of reel 616 causes grasper shaft 138 to be wound onto reel 616 or unwound from reel 616 depending on the direction of rotation. Winding of grasper shaft 138 onto reel 616 corresponds to proximal retraction of implant 102 (e.g., into inner shaft lumen 131), while unwinding of grasper shaft 138 from reel 616 corresponds to distal advancement of implant 102 (e.g., out of inner shaft lumen 131). In the embodiment of FIGS. 9A-9B, channel 617 is a helical channel that extends about the circumference of reel 616 multiple times. In the embodiment depicted in FIG. 6B, channel 617 is omitted.

Figure 6C:
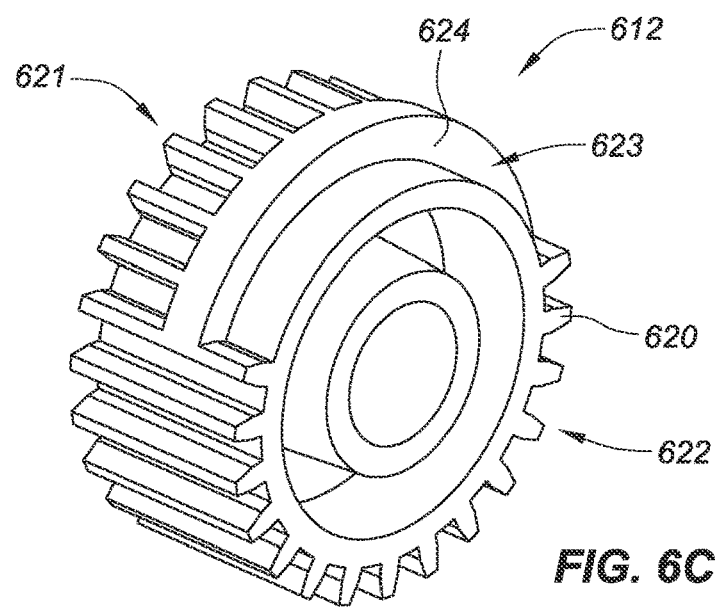
FIG. 6C is a perspective view depicting an example embodiment of a gear for use with the delivery system.

In some embodiments, input gear 612 can be configured as an interrupted gear, where one or more teeth are not present such that rotation of input gear 612 will not cause corresponding rotation of another gear at all times. An example of such an input gear 612 is depicted in the perspective view of FIG. 6C. From the perspective depicted here, input gear 612 has teeth 620 spaced at regular intervals on the left side 621 of the radial edge of the gear. Teeth 620 are also present at regular intervals on the right side 622 of the radial edge of the gear except for a region 623 where no teeth are present. A smooth surface hub 624 is present adjacent to this interrupted region 623. The right side 622 of input gear 612 is configured to engage with reel gear 614. Placement of interrupted region 623 is predetermined such that continuous user depression of trigger 202 (and thus continuous rotation of pinion gear 605, face gear 610, and input gear 612) does not translate into continuous rotation of reel gear 614. Instead, reel gear 614 will only be turned when engaged with the portion of input gear 612 having teeth 620 and will not be turned while interrupted region 623 is traversing reel gear 614. Placement of interrupted region 623 allows for a pause in longitudinal translation (e.g., distal and/or proximal) of grasper shaft 138. Interrupted region 623 is specifically placed such that longitudinal translation only occurs during certain parts of the delivery sequence.

In this embodiment, placement of switch 604 in the down position translates user depression of trigger 202 into pushing of implant 102, while placement of switch 604 in the up position translates user depression of trigger 202 into pulling of implant 102 and/or inner shaft 130. In other embodiments, these switch positions can be reversed to cause the opposite motions.

Figure 7A:
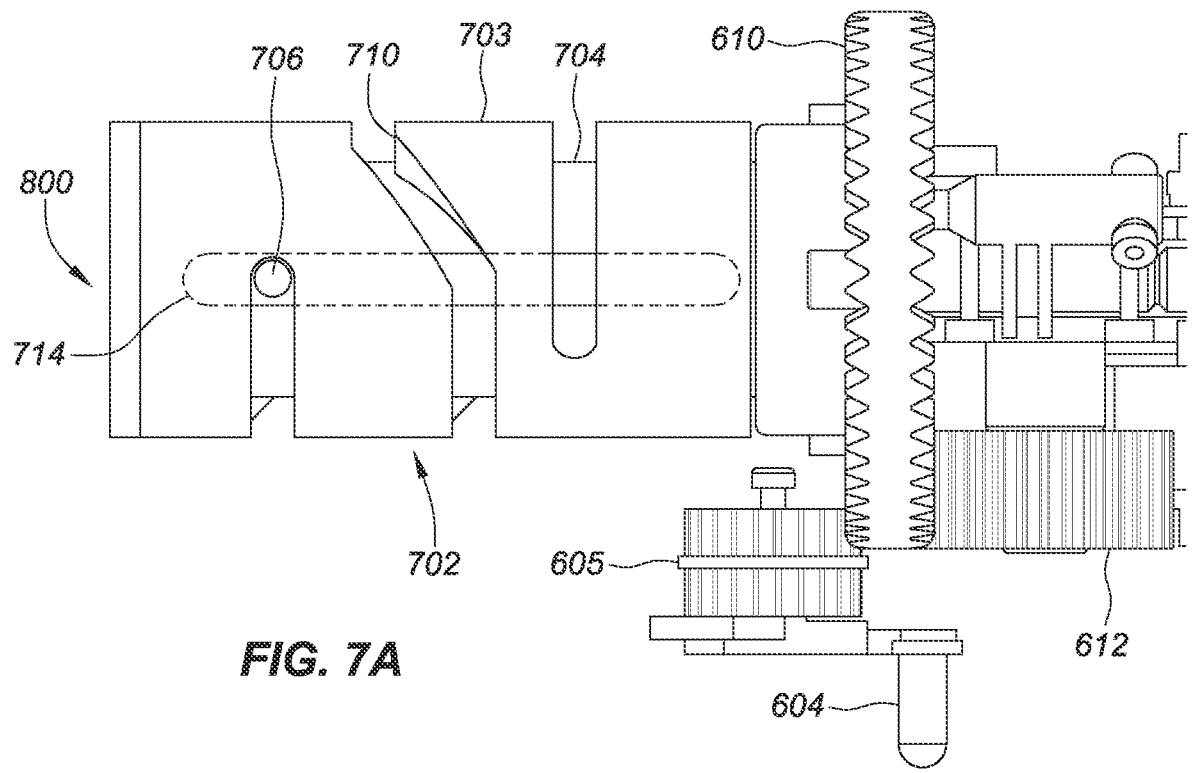
FIG. 7A is an interior top down view depicting an example embodiment of components of a proximal control device.
Figure 7B:
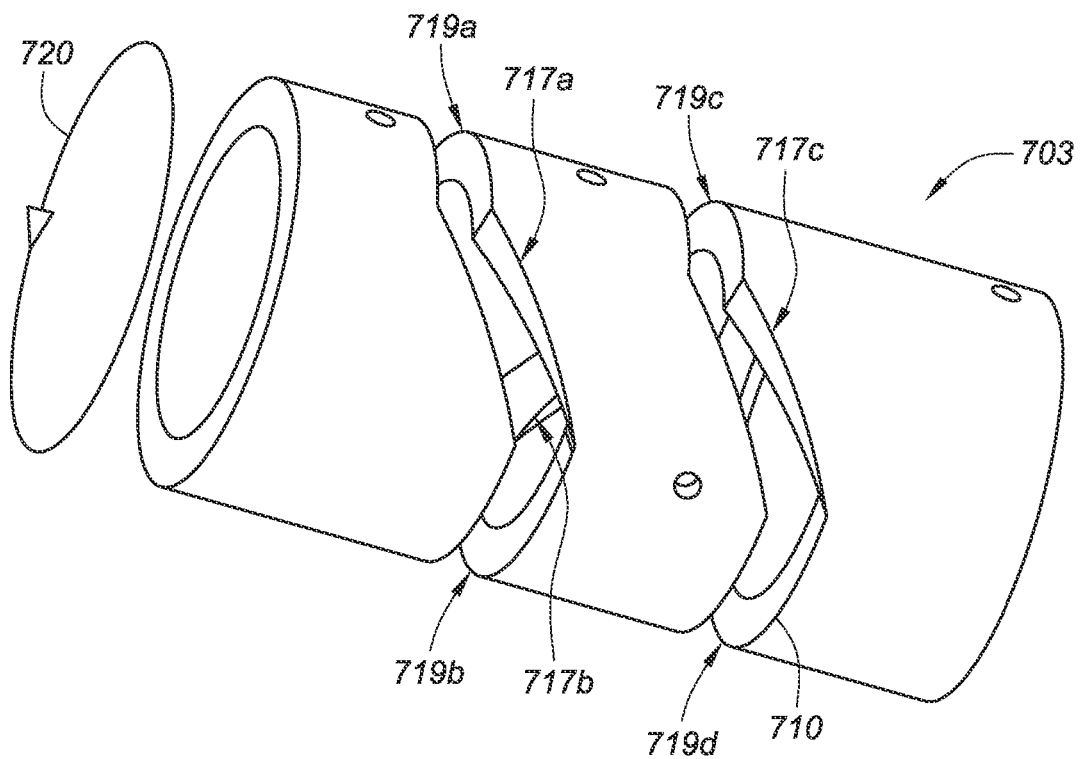
FIG. 7B is a perspective view depicting an example embodiment of a cam.

FIG. 7A is a top down view depicting a cam assembly 702 of proximal control device 200. Cam assembly 702 includes an outer slotted tube or cam 703, an inner slotted tube 704, and a guide member 706. Cam assembly can be positioned within yoke 601. FIG. 7B is a perspective view depicting this embodiment of cam 703. Cam 703 is coupled with face gear 610 such that rotation of face gear 610 also rotates cam 703. Inner slotted tube 704 is mounted within proximal control device 200 such that it does not rotate when cam 703 rotates. Guide member 706 can be configured as an arm or strut member that is located within and follows both a slot 710 in cam 703 and a slot 714 in inner tube 704. Guide member 706 is coupled with a hub 802 (FIG. 8) located within inner slotted tube 704 that is in turn coupled with inner shaft 130. Rotation of face gear 610 causes rotation of cam 703 which in turn causes guide member 706 to follow the path or route of slot 710 in cam 703. Because guide member 706 extends through slot 714 in inner tube 704, which is not rotatable, rotation of cam 703 causes guide member 706 to move only in a longitudinal direction and not a radial direction.

Slot 710 can have one or more sloped slot portions and/or one or more radial slot portions. In the embodiment depicted here, slot 710 has multiple sloped portions (e.g., slot portions 717a, 717b, and 717c) and multiple radial portions (e.g., slot portions 719a, 719b, 719c, and 719d). Other shapes can be used as well and linked together to form the desired path. Sloped slot portions 717 can have a constant or variable slope, and in some embodiments these sloped slot portions can vary such that the slope reverses from positive to negative (like a "V").

A sloped slot portion 717 can be an opening or groove in cam 703 with a non-perpendicular and non-parallel angle (with respect to longitudinal axis 204) that moves guide member 706 along longitudinal axis 204 during rotation. A radial slot portion 719, in most embodiments, is parallel to longitudinal axis 204 such that rotation of cam 703 moves radial slot portion 719 with respect to guide member 706 while guide member 706 does not move in the longitudinal direction (proximally or distally). Radial slot portion 719 can correspond to a pause in the delivery sequence where trigger 202 is continuing to be depressed and other components of delivery device 103 are moving but inner shaft 130 remains in the same relative position.

In FIG. 7A, guide member 706 is located at the distal most terminus within radial slot portion 719a (FIG. 7B). For retraction of inner shaft 130, cam 703 is rotated in counter-clockwise direction 720. While cam 703 rotates radial slot portion 719a past guide member 706 there is no longitudinal movement of inner shaft 130. When guide member 706 reaches sloped slot portion 717a, it begins to proximally retract along with inner shaft 130. This process repeats as guide member 706 moves through the succession of radial slot portions 719 (e.g., pauses in shaft 130 retraction) and sloped slot portions 717 (e.g., retraction of shaft 130). In some embodiments, guide member 706 can be selectively coupled with outer shaft 120 to cause longitudinal movement of that component. For example, proximally retracting inner shaft 130, outer shaft 120 can be proximally retracted as well, for example to allow the physician to continue imaging the deployment process. Similar embodiments utilizing a cam assembly, that can be used with the embodiments described here, are described in the incorporated Int'l Publ. No. WO 2017/184887.

Figure 8:
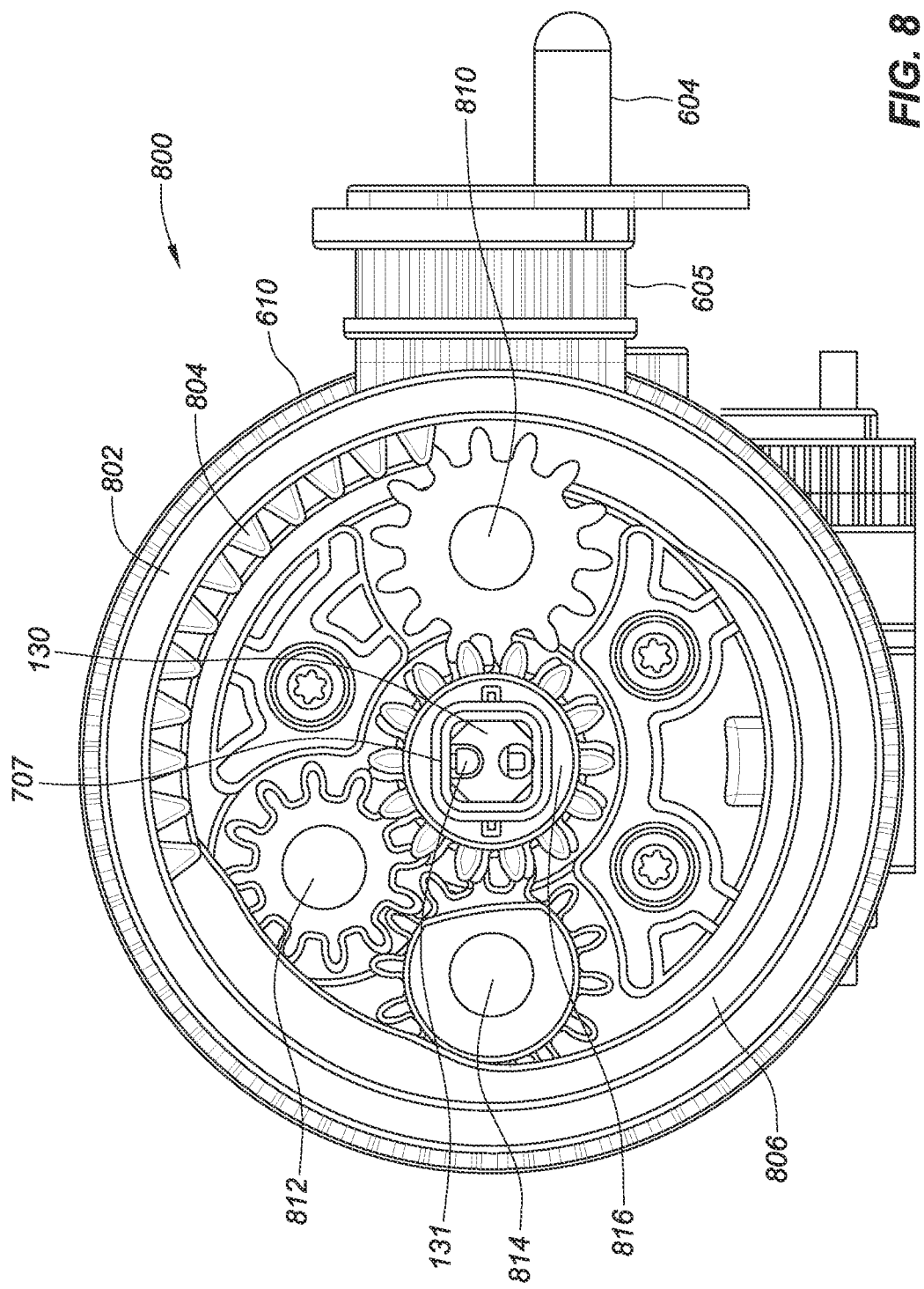
FIG. 8 is an interior side view depicting an example embodiment of a gear assembly.

Proximal control device 200 can also be configured to rotate inner shaft 130 with respect to distal control member 140 during extrusion of implant 102 from within inner lumen 131. FIG. 8 is a side view depicting an example embodiment of a second gear assembly 800 configured to translate rotation of face gear 610 into rotation of hub 707, which is in turn coupled with inner shaft 130. Gear assembly 800 is located distal to cam assembly 702 (see FIGS. 6A and 7A). Gear assembly 800 can include a first gear 802 coupled with cam 703 such that rotation of cam 703 causes rotation of gear 802. In this embodiment, gear 802 has an annular or ring-like shape with a first set of radially inwardly projecting teeth 804 and an interrupted region 806. Gear 802 can have a second set of radially inwardly projecting teeth (not shown) with an interrupted region that are located in a plane different from teeth 804.

Gear assembly 800 can also include translation gears 810, 812, and 814, which can also be referred to as planetary gears, which translate rotation of gear 802 to a centrally located gear 816. In this example, the first set of teeth 804 engages with gear 810, which in turn engages with and rotates central gear 816 in a first direction. Central gear 816 has an aperture in which hub 707 is rotationally secured but free to slide longitudinally. Thus, rotation of gear 802 is translated to rotation of hub 707, which in turn rotates inner shaft 130. The second set of teeth of gear 802 (not shown) engages with gear 812, which in turn is engaged with gear 814, which in turn is engaged with central gear 816 and causes rotation of central gear 816 in the opposite direction. Depending on the positions of the first and second sets of teeth, and the interrupted regions in the various planes, constant rotation of annular gear 802 in one direction can translate into timed rotation of central gear 816 in the same direction, in the opposite direction, or no rotation of central gear 816 at all.

The delivery sequence of the three stages can be described relative to corresponding features of implant 102. Each ring-shaped structure 111 and interconnect 112 is subjected to pushing by grasper 136. In some embodiments, implant 102 can be rotated by grasper 136 as well. In some embodiments, the total longitudinal push distance traveled by grasper 136 (provided by reel 616) in an implant delivery is roughly equivalent to the additive circumferences of all ring-shaped structures 111 of the embodiment of implant 102. The combined movement of pushing and rotating can ensure that, despite lateral forces impinged on the prostatic urethra, ring-shaped structures 111 of implant 102 are laid down in plane to provide sufficient radial force to open the cavity. Each interconnect 112 of implant 102 is subjected to the pulling stage (without rotation) by the hub and cam. Thus, the total axial pull distance traveled by the hub inside the cam is roughly equivalent to the total longitudinal length of implant 102. The pulling stage and pushing/rotation stage do not occur at the same time during the delivery sequence; they are mutually exclusive.

Proximal control device 200 can be configured so that, after all of ring-shaped structures 111 have been deployed from inner lumen 131 but prior to advancement of proximal engagement feature 115 and recess 139 from within lumen 131, further deployment of implant 102 is automatically prevented. This provides the physician with an opportunity to verify that implant 102 has been properly deployed and placed prior to releasing implant 102 from delivery device 103.

FIGS. 9A-9F are interior perspective views depicting an example embodiment of proximal control device 200 with a lock or locking mechanism 900 for preventing premature release of implant 102. Locking mechanism 900 interfaces with a groove or channel 902 in the proximally facing surface of face gear 610 as shown in FIGS. 9A-9B. A longitudinally, laterally, and radially inwardly movable tracking mechanism 904 has a head portion with a projection 905 and is biased distally such that projection 905 presses into and tracks within groove 902. As face gear 610 is rotated by pinion gear 605 (not shown), tracking mechanism 904 follows the spiral groove 902 and moves radially inwardly. This movement continues until implant 102 is almost fully deployed, but proximal engagement member 115 is still retained by grasper 136 within inner lumen 131. At this point, projection 905 enters a relatively deeper portion 906 of groove 902 (e.g., a cavity), which securely captures tracking mechanism 904. Further rotation of face gear 610 causes tracking mechanism 904 to move laterally or swivel in a semicircular arc to the position depicted in FIGS. 9C-9D, where an arm 907 of tracking mechanism 904 is prevented from further lateral motion by a fixed body 915. Further rotation of face gear 610 is prevented, which in turn prevents rotation of all gears and prevents the user from continuing to pull trigger 202.

If the physician is satisfied with placement of implant 102, then an unlock actuator or tab 910, which is accessible to the user outside of housing 203, is pulled proximally. Unlock tab 910 is coupled, directly or indirectly, to the control wire 146 responsible for releasing retainer 142 as described with respect to FIGS. 2C and 2D. Thus, the proximal movement of unlock tab 910 causes retainer 142 to move proximally and allows release of distal engagement member 114 of implant 102 from delivery device 103. Unlock tab 910 can also be coupled with tracking mechanism 904 such that proximal retraction of tab 910 withdraws projection 905 from within groove 902. This action unlocks device 200 and the user is free to continue depression of trigger 202, which in turn feeds reel 616 forward to further unwind grasper shaft 138 and cause proximal engagement member 115 of implant 102 and recess 139 to exit inner lumen 131 of shaft 130. At this stage both distal engagement member 114 and proximal engagement member 115 of implant 102 are exposed and implant 102 is free to disengage or release from device 103.

Proximal control device 200 can be configured to rotate distal control member 140 with respect to the other components of delivery device 103 to facilitate the removal of distal engagement member 114 from distal control device 140. In the embodiment depicted in FIG. 9E, a second cam 940 is rotatable within body 941. Distal control member 140 (not shown) is secured to cam 940 (e.g., with a set screw) such that rotation of cam 940 causes rotation of distal control member 140. Cam 940 has two sloped surfaces 944a and 944b that are in contact with two rigid members (e.g., pins) 946a and 946b, respectively, that are fixed to body 941 and located on opposite sides of cam 940. Cam 940 is rotatable but longitudinally fixed with respect to body 941. Pulling unlock tab 910 moves body 941 and members 946a and 946b proximally. Cam 940 cannot move proximally so the contact of members 946 on sloped surfaces 944 cause cam 940 to rotate, which in turn rotates distal control member 140. Thus, the retraction of tab 910 releases retainer 142 and rotates distal control member 140, which uncovers distal engagement member 114 of implant 102 (implant 102 is now expanded in contact with the urethra). The rotation assists in withdrawing distal engagement member 114 from recess 143 of member 140 and can ensure complete disengagement.

In some embodiments, distal control member 140 has a preset bend (not shown) proximal to retainer 142. Distal control member 140 is deformed from this preset bent shape when attached to distal engagement member 114 (e.g., as depicted in FIGS. 2B, 2G, and 2H), and thus is biased to return to this preset bent shape, which can also assist in the disengagement of member 140 from implant 102 (either instead of, or in addition to, embodiments where device 200 rotates member 140).

Figure 9D:
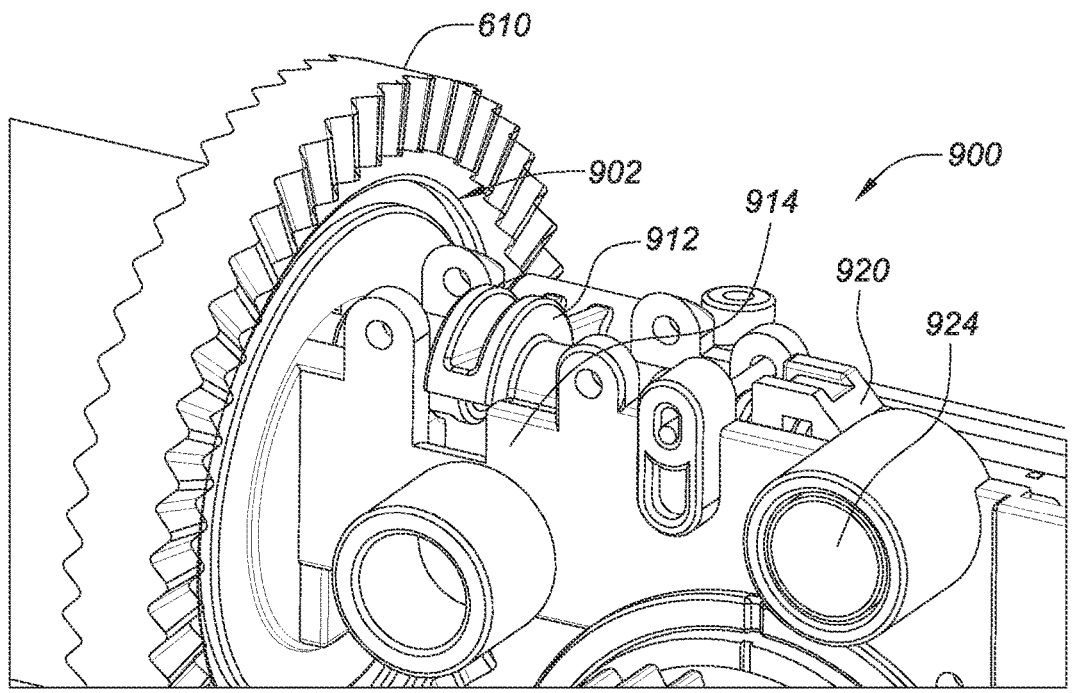

A stop surface 912 is present on tracking mechanism 904 that opposes another stop surface 914 on fixed body 915. In the position of tracking mechanism 904 shown in FIG. 9B, these opposing stop surfaces 912 and 914 prevent unlock tab 910 from being proximally retracted since body 915 is a separate component held in a static position (e.g., by housing 203). Lateral movement of tracking mechanism 904, e.g., in the semicircular arc, continues until stop surface 912 ceases and passes stop surface 914 as shown in FIG. 9D. This feature prevents premature unlocking of implant 102 by proximally retracting unlock tab 910 before implant 102 is sufficiently deployed.

Figure 9E:
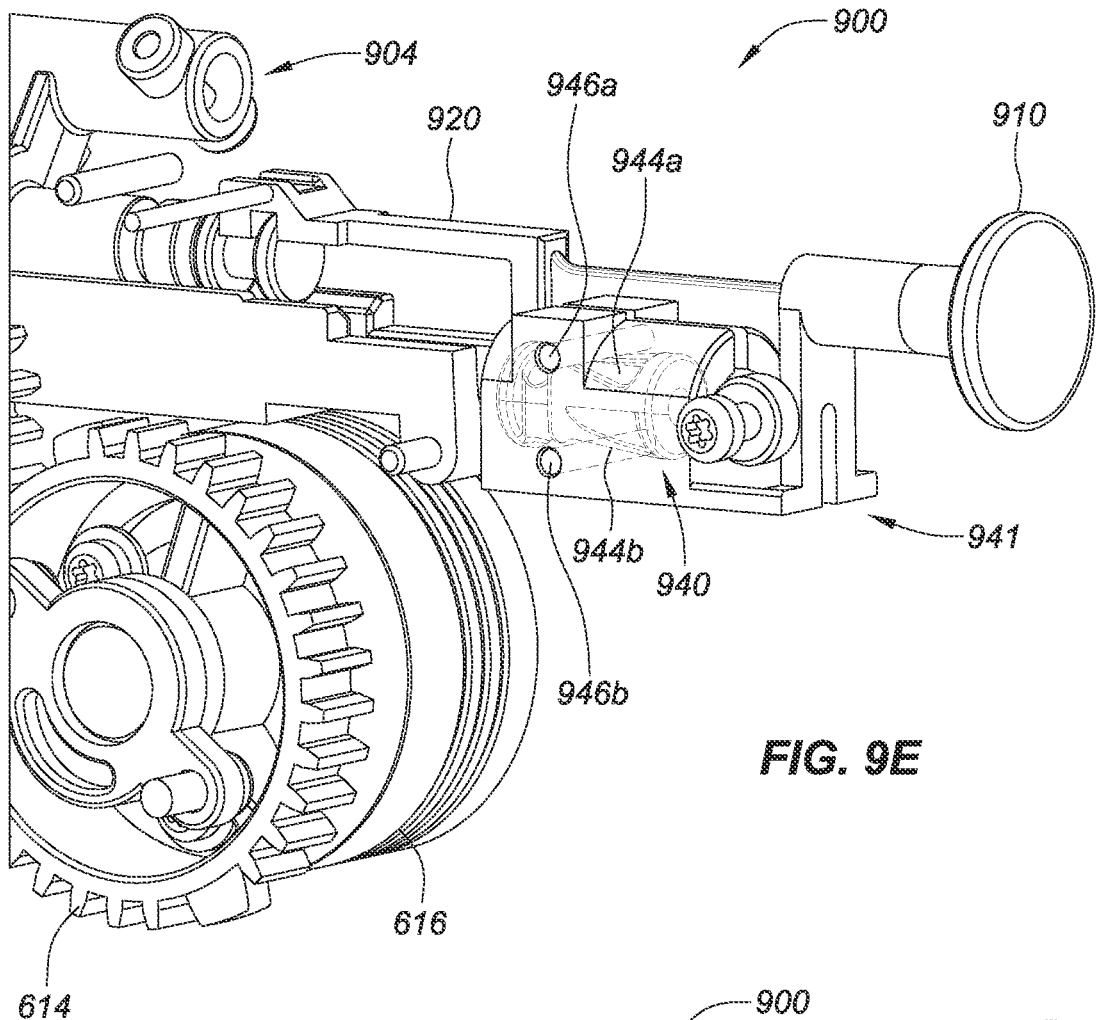
Figure 9F:
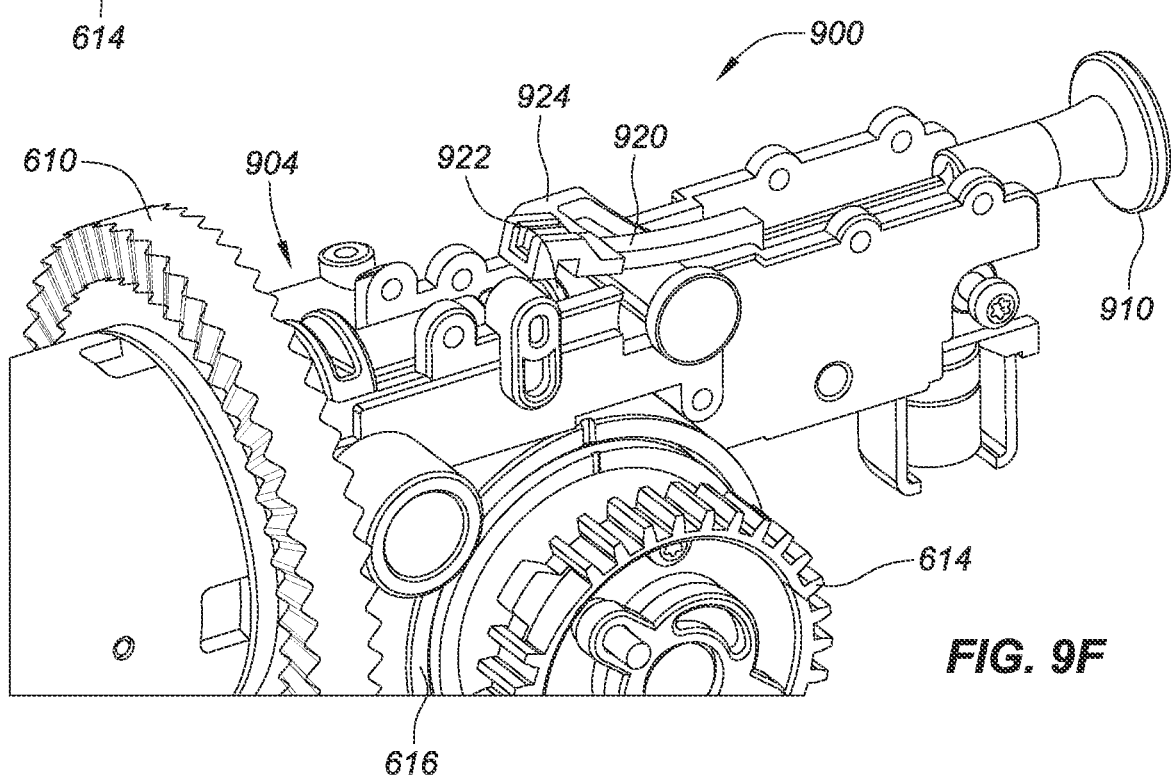

Proximal control device 200 can also include an emergency release mechanism that permits removal of a partially deployed implant 102 from the patient. Unlock tab 910 can be decoupled from tracking mechanism 904 by disengaging a notch of a deflectable arm 920 from a detent 922 on the base of tracking mechanism 904. In other embodiments the notch and detent features can be reversed. An emergency release button 924 having a ramped surface 925 is positioned underneath arm 920 (see FIGS. 9A-9B). Actuation, e.g., by pushing, release button 924, causes the ramped surface 925 to deflect arm 920 upwards and decouple the notch from detent 922 as depicted in FIG. 9E. In this state, unlock tab 910 is decoupled from tracking mechanism 904 and is free to be proximally retracted even while stop surfaces 912 and 914 are in opposing positions. Proximal retraction of unlock tab 910 retracts control wire 146 and releases distal engagement member 114 of implant 102 from distal control member 140. At this point, the partially deployed implant 102 is still attached to grasper 136, which can be proximally retracted into outer shaft 120 and then completely removed from the patient.

Example Embodiments of Delivery Methods

Figure 10A:
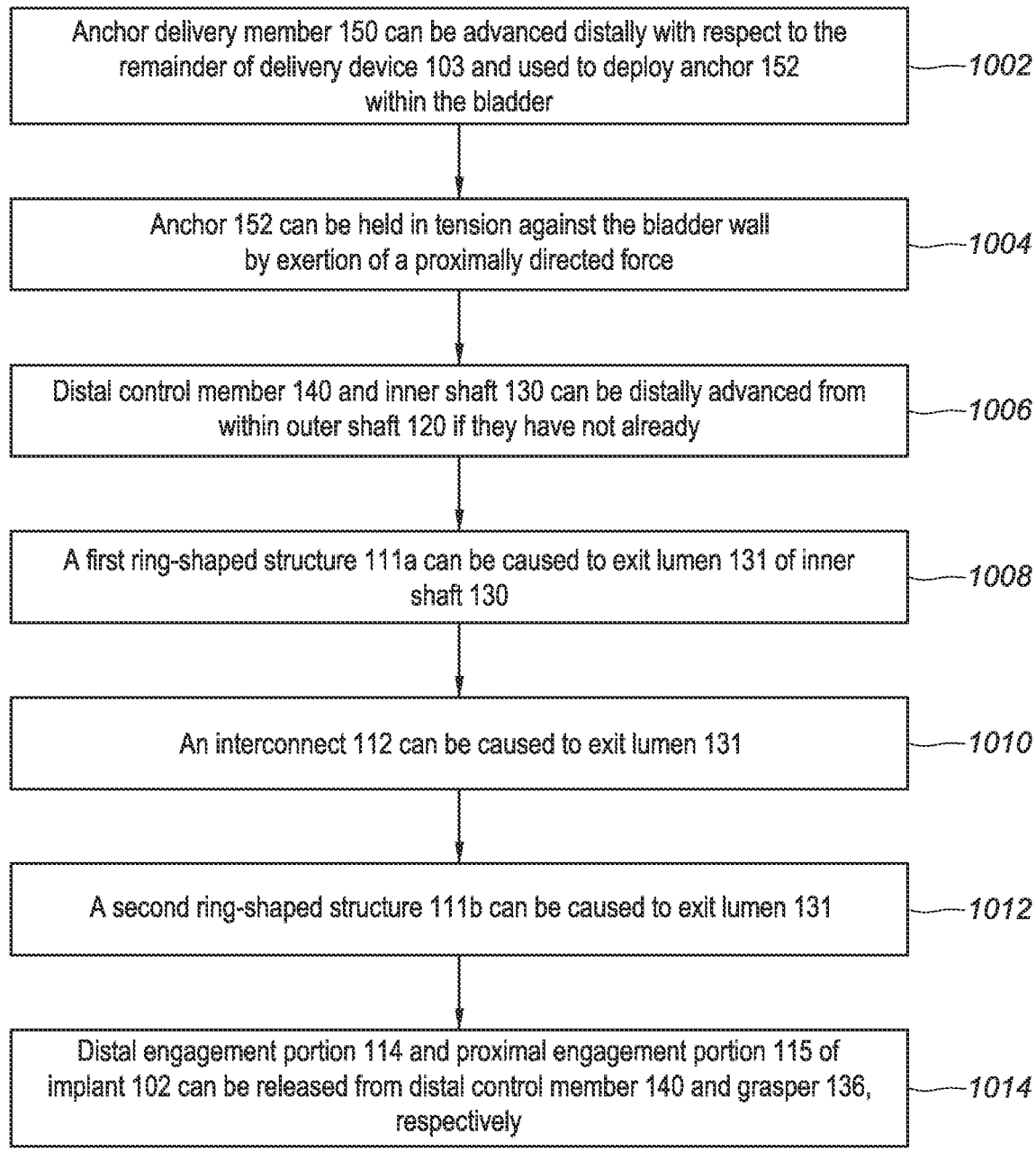
FIG. 10A is a flowchart depicting an example embodiment of a method for delivering an implant.

FIG. 10A is a flow diagram depicting an example embodiment of a method 1000 of delivering implant 102 using system 100. Distal end region of outer shaft 120 is inserted into the urethra, preferably with inner shaft 130, distal control member 140, and anchor delivery member 150 in retracted states fully contained within outer shaft 120 such that no part is extending from the open distal terminus of outer shaft 120. After advancement into the urethra, at step 1002 anchor delivery member 150 is advanced distally with respect to the remainder of delivery device 103 (e.g., members 120, 130, and 140) and used to deploy anchor 152 within the bladder. In some embodiments, deployment of anchor 152 can be the inflation of one or more balloons (e.g., as depicting in FIGS. 2B, and 4H-4J) by the introduction of an inflation medium through an injection (e.g., luer taper) port. FIG. 6A depicts tubing 650 for balloon inflation. In other embodiments deployment of anchor 152 can be the advancement of one or more wire-form members from anchor delivery member 150 such that they deflect into a position that opposes the bladder wall (e.g., FIGS. 4A-4G). The longitudinal positioning (e.g., advancement and retraction) of anchor delivery member 150 and/or any wire-form members can be accomplished manually by the user manipulating a proximal end of anchor delivery member 150 and/or any wire-form members either directly or with proximal control device 200.

At step 1004, anchor 152 can be held in tension against the bladder wall by exertion of a proximally directed force on device 200. Anchor 152 can therefore provide an ordinate for system 100 from which to deploy implant 102 in an accurate location. This feature can ensure the implant is not placed too close to the bladder neck.

At 1006, distal control member 140 and inner shaft 130 can then be distally advanced from within outer shaft 120 if they have not already (for example, step 1006 can occur prior to steps 1002 and/or 1004). The user can manipulate the position of proximal control device 200 with the aid of imaging (as described herein) until implant 102 is in the desired position. Once implant 102 is in the desired position, the implant deployment procedure can begin. The steps for implant deployment can be performed automatically by user actuation of proximal control device 200 (e.g., actuation of trigger 202, selection of a position for switch 604, etc.), or the steps can be performed directly by hand manipulation of each component of delivery device 103, or by a combination of the two as desired for the particular implementation.

In some embodiments, deployment of implant 102 from within lumen 131 is fully accomplished by (1) distally advancing grasper 136 with respect to inner shaft 130, while inner shaft 130 is not moved; while in other embodiments, deployment of implant 102 from within inner lumen 131 is fully accomplished by (2) proximally retracting inner shaft 130 with respect to grasper 136 while grasper 136 is not moved. In some embodiments, deployment of implant 102 is fully accomplished by (3) a combination of both movements. In still other embodiments, deployment of implant 102 is fully accomplished by (1), (2), or (3) in combination with one or more rotations of inner shaft 130, in one or more directions (e.g., clockwise or counterclockwise) with respect to distal control member 140.

An example embodiment of a sequence of steps 1008, 1010, and 1012 for deploying implant 102 is described with reference to FIG. 10A and the timing diagram of FIG. 10B. First with reference to FIG. 10A, at step 1008 a first ring-shaped structure 111a is caused to exit lumen 131 of inner shaft 130, at step 1010 an interconnect 112 is caused to exit lumen 131, and at step 1012 a second ring-shaped structure 111b is caused to exit lumen 131. Steps 1010 and 1012 can be repeated for each additional interconnect 112 and ring-shaped structure 111 present on implant 102.

Figure 10B:
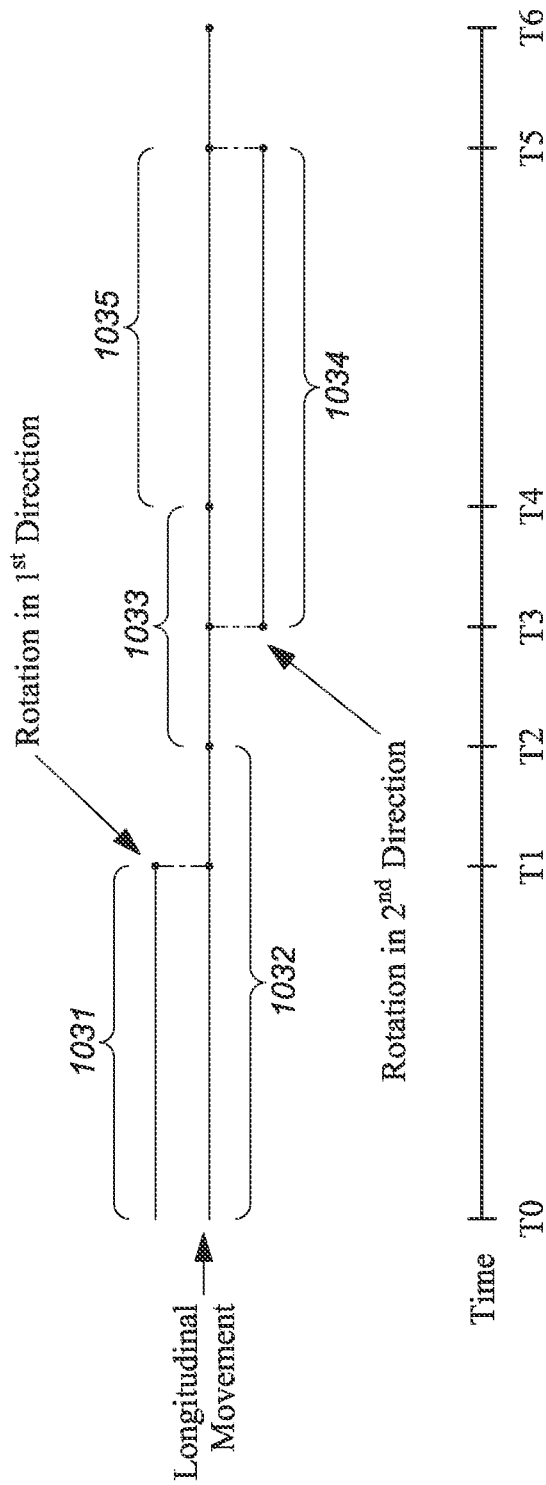
FIG. 10B is a timing diagram depicting an example embodiment of a sequence of steps for deploying an implant.

In FIG. 10B, step 1008 begins at the far left of the timing diagram at T0. Deployment of ring-shaped structure 111a corresponds to the duration of time marked 1008, deployment of interconnect 123 corresponds to time span 1010, and deployment of ring-shaped structure 111b corresponds to time span 1012. Those of ordinary skill in the art will recognize that the differentiations between deployment of a ring-shaped structure 111 and deployment of an interconnect 112 are approximations as the transitions between those portions of implant 102 can be gradual and do not have to have precise demarcations.

The embodiment described with respect to FIG. 10B is for an implant with ring-shaped structures 111 having opposite directions of winding (e.g., clockwise, then counterclockwise, then clockwise, etc.). Three different motions are indicated in FIG. 10B. At top is rotational motion of inner shaft 130 in one direction (e.g., clockwise), in the middle is longitudinal motion (e.g., proximal or distal) of one or more components of delivery device 103, and at bottom is rotational motion inner shaft 130 in the direction opposite (e.g., counterclockwise) to that indicated at top. In embodiments where ring-shaped structures 111 of implant 102 are all wound in the same one direction, rotation of inner shaft 130 will also be in only one direction.

From time T0 to T1, deployment of implant 102 is accomplished by rotating inner shaft 130, as indicated in region 1031. At the same time, in region 1032, grasper 136, and thus implant 102, is distally advanced without moving outer shaft 120 longitudinally (neither distally nor proximally) nor rotationally, and also without longitudinally moving inner shaft 130 (neither distally nor proximally). By way of example, within proximal control device 200 the rotational movement of inner shaft 130 without corresponding longitudinal movement of both inner shaft 130 and outer shaft 120 is accomplished by the user depression of trigger 202 being translated (through the yoke and pawl) into the rotation of pinion gear 605 and face gear 610. Rotation of face gear 610 also rotates cam 703 of cam assembly 702 (FIGS. 7A-7B) while guide member 706 is in a radial slot portion (e.g., 719a), and thus neither of shafts 120 and 130 move longitudinally. Rotation of cam 703 also causes second gear assembly 800 (FIG. 8) to rotate inner shaft 130. The advancement of grasper 136 is caused by face gear 610 rotating input gear 612, which in turn rotates reel gear 614 (FIGS. 6A-6B) and causes reel 616 to rotate and unwind grasper shaft 138 distally.

From time T1 to T2, rotation of inner shaft 130 is stopped but distal advancement of grasper 136 continues while shafts 120 and 130 do not move longitudinally. By way of example, within proximal control device 200, user depression of trigger 202 continues and cam 703 continues to rotate with guide member 706 in a radial slot portion (e.g., 719a).

Rotation of cam 703 continues to rotate annular gear 802 of second gear assembly 800, but at this point an interrupted portion (without teeth) of annular gear 802 is reached none of planetary gears 810, 812, and 814 are rotated, and thus rotation of central gear 816 and inner shaft 130 is stopped. In this embodiment, deployment of first ring-shaped structure 111a is complete at time T2.

From time T2 to T4, deployment of a first interconnect 112 takes place. In region 1033, from time T2 to T4, no distal advancement of grasper 136 (and implant 102) occurs. Deployment of interconnect 112 is accomplished by proximal retraction of both outer shaft 120 and inner shaft 130 while holding grasper 136 in place. This causes interconnect 112 to exit inner lumen 131 of shaft 130. By way of example, in proximal control device 200, user depression of trigger 202 continues and face gear 610 continues to rotate, as do both cam 703 and input gear 612. Interrupted portion 623 in input gear 612 is reached and rotation of input gear 612 no longer causes rotation of reel gear 614, and thus distal advancement of grasper shaft 138 is stopped. Within cam assembly 702, guide member 706 transitions from a radial slot portion (e.g., 719a) to a sloped slot portion (e.g., 717a), and rotation of cam 703 causes guide member 706 to move proximally. With guide member 706 coupled with shafts 120 and 130, these shafts 120 and 130 also move proximally.

With respect to rotation of inner shaft 130, from time T2 to T3 no rotation of inner shaft 130 occurs. Within proximal control device 200 the interrupted portion of annular gear 802 continues and there is no rotation of shaft 130 by central gear 816.

In embodiments where interconnect 112 is straight, it can be desirable to refrain from rotating shaft 130 while interconnect 112 is deployed from time T2 to T4. For embodiments where interconnect 112 is curved, such as the embodiment of FIGS. 1B-1D, it can be desirable to initiate rotation of inner shaft 130 during interconnect deployment. FIG. 10B depicts deployment for a curved interconnect 112, and from T3-T4 inner shaft 130 is rotated in the opposite direction as indicated by region 1034. By way of example, within proximal control device 200, user depression of trigger 202 continues and this motion is translated to annular gear 802, which has a region with teeth that come into engagement with the planetary gears responsible for motion of central gear 816 in the opposite direction. Rotation of central gear 816 in the opposite direction therefore begins and inner shaft 130 is likewise rotated in the opposite direction from that of times T0 to T1, which facilitates deployment of interconnect 112 and begins rotation of inner shaft in the direction appropriate for the oppositely wound second ring-shaped structure 111b.

At T4, deployment of interconnect 112 is complete and deployment of second ring-shaped structure 111b begins. Proximal retraction of shafts 120 and 130 is stopped as indicated by the cessation of region 1033. Distal advancement of grasper shaft 138 is restarted in region 1035 at T4, while outer shaft 120 is not moved rotationally nor longitudinally. Rotation of inner shaft 130 continues as indicated in region 1034, but inner shaft 130 is not moved longitudinally. By way of example, within proximal control device 200, the user continues to depress trigger 202. Rotation of cam 703 continues but guide member 706 reaches a second radial slot portion (e.g., 719b) and proximal movement of guide member 706 stops (as does retraction of shafts 120 and 130). Rotation of central gear 816 continues. Interrupted portion 623 of input gear 612 ceases and teeth 620 reengage with reel gear 614 causing rotation of both reel gear 614 and reel 616 to begin again, and thus distal advancement of grasper shaft 138 begins as well.

These motions continue until time T5, at which point rotation of inner shaft 130 is stopped. Within proximal control device 200, an interrupted portion of annular gear 802 is reached and gear 802 disengages from the planetary gears and rotation of central gear 816 is stopped. User depression of trigger 202 continues from time T5-T6, the components operate with similar motions as described from time T1 to T2. If another interconnect 112 and ring-shaped structure 111 are present, then the sequence beginning at time T6 can be the same as that described beginning at time T2 and continuing to time T6. This process can repeat as needed until all ring-shaped structures 111 of implant 102 are deployed. In some embodiments, further depression of trigger 202 can be stopped by lock mechanism 900 (FIGS. 9A-9B) to prevent premature deployment and release of proximal engagement portion 115.

In many embodiments described here, deployment of all of ring-shaped structures 111 can occur with a single continuous depression of trigger 202. In all of these embodiments, proximal control device 200 can instead be configured such that repeated pulls of trigger 202 are required to deploy all of ring-shaped structures 111 of implant 102.

During deployment, e.g., after time T0 up until completed deployment of the proximal-most ring-shaped structure 112, if the physician wishes to recapture implant 102, then depression of trigger 202 can be stopped. Trigger 202 can be spring-loaded or otherwise biased to return to the outermost position. The physician can adjust switch 604 from the position corresponding to deployment to a different position corresponding to recapture. This adjustment of switch 604 will disengage pawl 603 and engage pawl 602. The physician can again depress trigger 202 and that depression will translate into the reverse motion of face gear 610, which in turn translates into reverse motion of the remainder of first gear assembly 600, cam 703, and second gear assembly 800. For example, if switch 604 is adjusted at any time between times T0 and T6, then the next depression of trigger 202 will cause the sequence of events to be reversed going from right to left in FIG. 10B. Because these motions are merely a reversal of that already described, they will not be repeated here.

If the physician is satisfied with deployment, then at 1014 distal engagement portion 114 and proximal engagement portion 115 of implant 102 can be released from distal control member 140 and grasper 136, respectively. By way of example, in proximal control device 200 the physician can pull tab 910 to permit trigger 202 to be depressed the rest of the way, which in turn can deploy proximal engagement portion 115 of implant 102, either by distal advancement of grasper 136, proximal retraction of shafts 120 and 130, or both. Tab 910 can be coupled with control wire 146 and the pulling of tab 910 can pull wire 146 and remove retainer 142 from distal engagement portion 114.

Anchor 152 can then be recaptured (e.g., deflation of the balloon or retraction of the wire-form members) and withdrawn into anchor delivery member 150 if desired. Anchor delivery member 150, distal control member 140, and inner shaft 130 can be retracted into outer shaft 120 and then withdrawn from the urethra.

The embodiments described herein are restated and expanded upon in the following paragraphs without explicit reference to the figures. In many example embodiments, a system for delivering an implantable device is provided, where the system includes a delivery device including: an outer tubular member; an inner tubular member having a first inner lumen and a second inner lumen, the inner tubular member being slidable within the outer tubular member, where the first inner lumen is adapted to house an elongate grasper member configured to releasably couple with a proximal portion of an implant; and a distal control member slidable within the second inner lumen, where the distal control member includes a retainer configured to releasably couple with a distal portion of the implant.

In some embodiments, the implant is configured to maintain a prostatic urethra in an at least partially open state. In some embodiments, the implant has a body including first and second ring-shaped structures and an interconnect that extends between the first and second ring-shaped structures. The body of the implant can be only a single wire. The implant can include a distal engagement member configured to releasably couple with the retainer and/or a proximal engagement member configured to releasably couple with the elongate grasper member. In some embodiments, the implant includes a wire-like distal engagement member that extends proximally away from a distal-most portion of the implant and/or a wire-like proximal engagement member. In some embodiments, the first ring-shaped structure can be the distal-most ring-shaped structure of the implant and has a relatively smaller width than the second ring-shaped structure.

In some embodiments, the inner tubular member is slidable and rotatable with respect to the distal control member while the retainer is releasably coupled with the distal portion of the implant. The system can further include an elongate member coupled with the retainer and having a proximal end that is manipulatable by a user to permit release of the distal portion of the implant from the retainer. In some embodiments, the retainer is tubular and adapted to slide along the distal control member. The distal control member can include a recess adapted to receive the distal portion of the implant and the retainer can be movable to uncover the recess while the distal portion of the implant is received within the recess. In some embodiments the retainer includes a slot through which the implant can pass.

In some embodiments, the system includes an elongate anchor member. The elongate anchor member can include an anchor configured to contact a bladder wall. The anchor can be an inflatable balloon or multiple inflatable balloons. In some embodiments, the elongate anchor member includes a wire-form member having a portion configured to automatically deflect when deployed.

In some embodiments, the elongate grasper member includes a recess configured to releasably couple with the proximal portion of an implant. In some embodiments, the system is configured such that the proximal portion of the implant is free to release from the recess of the elongate grasper member when the recess is unconstrained by the first inner lumen.

In some embodiments, a proximal control device is included and coupled with a proximal end region of the delivery device. The proximal control device can be manipulatable by a user to control deployment of the implant from the delivery device. In some embodiments, the proximal control device includes a housing and is configured to distally advance the elongate grasper member with respect to the housing and the inner tubular member, and/or is configured to proximally retract and rotate the inner tubular member with respect to the housing and the distal control member, and/or is configured to proximally retract the outer tubular member with respect to the housing.

In some embodiments, the proximal control device includes: a user actuator; a first gear assembly coupled with the user actuator; a cam assembly coupled with the first gear assembly; and a second gear assembly coupled with the cam assembly. In some embodiments, the first gear assembly is configured to control longitudinal movement of the elongate grasper member, the cam assembly is configured to control longitudinal movement of the inner tubular member, and/or the second gear assembly is configured to control rotation of the inner tubular member.

In many embodiments, a system for delivering an implantable device is provided, where the system includes: a delivery device including a first elongate member having an inner lumen, an elongate grasper member slidable within the inner lumen and configured to hold a proximal portion of an implant, and a distal control member configured to hold a distal portion of the implant; and a proximal control device coupled with a proximal end region of the delivery device, the proximal control device including a user actuator and a housing.

In some embodiments, the proximal control device includes a first gear assembly within the housing, the proximal control device being configured to translate movement of the user actuator into movement in the first gear assembly. In some embodiments, the proximal control device includes a switch that selects between movement of the first gear assembly in a first direction and movement of the first gear assembly in a second direction. In some embodiments, the user actuator is coupled with a yoke that is coupled with a first pawl and a second pawl. The switch selectively can engage either the first pawl or the second pawl with a pinion gear. The proximal control device can be configured such that rotation of the pinion gear causes rotation of a face gear. The proximal control device can be configured such that rotation of the face gear causes rotation of a reel coupled with the elongate grasper member.

In some embodiments, the system further includes an input gear engaged with the face gear and a reel gear engaged with the input gear, the reel gear being coupled with or integrated with the reel. In some embodiments, the input gear is an interrupted gear, and rotation of the reel gear by the input gear causes rotation of the reel and longitudinal movement of the elongate grasper member. In some embodiments, movement of the first gear assembly in the first direction causes distal movement of the elongate grasper member, and movement of the first gear assembly in the second direction causes proximal movement of the elongate grasper member.

In some embodiments, the proximal control device includes a cam assembly within the housing, the proximal control device being configured to translate movement of the user actuator into movement in the cam assembly. The cam assembly can be coupled with the first elongate member and can be configured to move the first elongate member proximally with respect to the housing. In some embodiments, the cam assembly includes a rotatable cam having a slot, the first elongate member being coupled with a guide member received within the slot. In some embodiments, the slot includes a sloped slot portion and a radial slot portion. The cam assembly can include an inner tube having a longitudinal slot with the guide member received in the longitudinal slot.

In some embodiments, the first gear assembly includes a face gear having a first set of teeth that engage with teeth of another gear in the first gear assembly, where the face gear is coupled with the cam assembly such that movement of the face gear causes movement in the cam assembly.

In some embodiments, the proximal control device includes a second gear assembly and movement in the cam assembly can cause movement in the second gear assembly. The second gear assembly can be coupled with the first elongate member and can be configured to rotate the first elongate member with respect to the housing. The second gear assembly can include a central gear having an aperture configured to receive the first elongate member such that rotation of the central gear causes rotation of the first elongate member. In some embodiments, the second gear assembly includes an annular gear coupled with the cam assembly and coupled with the central gear by way of a planetary gear assembly. The annular gear can engage the planetary gear assembly such that rotation of the annular gear in a first direction causes first directional rotation of the central gear and rotation of the annular gear in a second direction causes second directional rotation of the central gear, the first directional rotation of the central gear being opposite to the second directional rotation.

In some embodiments, the proximal control device includes a releasable lock mechanism that prevents the proximal portion of the implant held by the elongate grasper member from exiting the inner lumen. In some embodiments, the lock mechanism includes a movable tracking mechanism that interfaces with a groove in a face gear of the first gear assembly, the proximal control device configured such that movement of the face gear moves the tracking mechanism as the implant exits the inner lumen. The proximal control device can be configured such that the tracking mechanism is prevented from further motion prior to the proximal portion of the implant exiting the inner lumen.

In some embodiments, the proximal control device includes a release structure configured to be actuated by a user, where the release structure is configured to disengage the tracking mechanism from the face gear to allow the proximal portion of the implant to exit the inner lumen. The release structure can be a pull tab and can be coupled with the elongate grasper member.

In many embodiments, a method of delivering an implant is provided that includes: advancing a delivery device within a body lumen of a patient, where the delivery device includes as first tubular member housing an implant, a distal control member slidable within the first tubular member and releasably coupled with a distal portion of the implant, and an elongate grasper member slidable within the first tubular member and releasably coupled with a proximal portion of the implant; causing relative motion between the elongate grasper member and the first tubular member to expose at least a portion of the implant from within the first tubular member; and releasing the distal portion of the implant from the distal control member and the proximal portion of the implant from the elongate grasper member.

In some embodiments, the body lumen is a prostatic urethra of a human. In some embodiments, upon release of the distal portion and the proximal portion, the implant is released from the delivery device in a state adapted to maintain the prostatic urethra in an at least partially open state.

In some embodiments, the implant has a body including first and second ring-shaped structures and an interconnect that extends between the first and second ring-shaped structures and causing relative motion can include distally advancing the elongate grasper member. In some embodiments, the method further includes rotating the first tubular member in a first direction with respect to the distal control member during exposure of the first ring-shaped structure from the first tubular member. In some embodiments, the method further includes rotating the first tubular member in a second direction with respect to the distal control member during exposure of the second ring-shaped structure from the first tubular member, the second direction being opposite the first direction. Rotation of the first tubular member in the first and second directions can occur while the distal control member is releasably coupled with the distal portion of the implant.

In some embodiments, the method further includes proximally retracting the first tubular member with respect to the elongate grasper member and the distal control member to expose the interconnect from the first tubular member. In some embodiments, the method further includes rotating the first tubular member while proximally retracting the first tubular member. In these embodiments, the interconnect can be curved.

In some embodiments, a retainer couples the distal portion of the implant to the distal control member, and the method includes releasing the retainer to release the distal portion of the implant from the distal control member.

In some embodiments, the method further includes exposing the proximal portion of the implant from within the first tubular member to release the proximal portion of the implant from the elongate grasper member.

In some embodiments, the method further includes anchoring the delivery device against a wall of a bladder before causing relative motion between the elongate grasper member and the first tubular member. In some embodiments, anchoring the delivery device includes inflating a balloon in the bladder.

In some embodiments, a proximal control device is coupled with a proximal end region of the delivery device, and the method includes moving a user actuator of the proximal control device by the user, where moving the user actuator causes motion in a first gear assembly of the proximal control device. In some embodiments, the first gear assembly causes the elongate grasper member to distally advance with respect to the first tubular member. In some embodiments, the first gear assembly causes movement in a cam assembly and a second gear assembly. In some embodiments, movement in the cam assembly causes intermittent retraction of the first tubular member with respect to the distal control member. In some embodiments, movement in the second gear assembly causes intermittent rotation of the first tubular member with respect to the distal control member.

In some embodiments, the user actuator is a first user actuator, and the method includes actuating a second user actuator of the proximal control device. In some embodiments, actuating the second user actuator unlocks a lock mechanism and permits release of the distal portion of the implant from the distal control member and the proximal portion of the implant from the elongate grasper member. In some embodiments, actuating the second user actuator removes a retainer from the distal portion of the implant and rotates the distal control member to cause the distal portion of the implant to disengage from the distal control member.

In some embodiments, the first tubular member is an inner tubular member slidably received within an outer tubular member of the delivery device.

All features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

As used herein and in the appended claims, the singular forms "a," "an," and "the" include plural referents unless the context clearly dictates otherwise While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. A system for delivering an implantable device, comprising:
   an implant;
   a delivery device comprising a first elongate member having an inner lumen, an elongate grasper member slidable within the inner lumen comprising a recess for holding a proximal portion of an implant, and a distal control member comprising a recess for holding a distal portion of the implant; and
   a proximal control device coupled with a proximal end region of the delivery device, the proximal control device comprising a user actuator, a housing, and a switch, wherein placement of the switch in a first position translates movement of the user actuator into movement of the implant in a first direction and placement of the switch in a second position translates the movement of the user actuator into movement of the implant in a second direction.

2. The system of claim 1, wherein the proximal control device comprises a first gear assembly within the housing, the proximal control device being configured to translate movement of the user actuator into movement in the first gear assembly.

3. The system of claim 2, wherein the switch selects between movement of the first gear assembly in a first direction and movement of the first gear assembly in a second direction.

4. The system of claim 3, wherein the user actuator is coupled with a yoke that is coupled with a first pawl and a second pawl.

5. The system of claim 4, wherein the switch selectively engages either the first pawl or the second pawl with a pinion gear.

6. The system of claim 5, wherein the proximal control device is configured such that rotation of the pinion gear causes rotation of a face gear.

7. The system of claim 6, wherein the proximal control device is configured such that rotation of the face gear causes rotation of a reel coupled with the elongate grasper member.

8. The system of claim 7, further comprising:
an input gear engaged with the face gear; and
a reel gear engaged with the input gear, the reel gear coupled with or integrated with the reel.

9. The system of claim 8, wherein the input gear is an interrupted gear, and wherein rotation of the reel gear by the input gear causes rotation of the reel and longitudinal movement of the elongate grasper member.

10. The system of claim 3, wherein movement of the first gear assembly in the first direction causes distal movement of the elongate grasper member, and wherein movement of the first gear assembly in the second direction causes proximal movement of the elongate grasper member.

11. The system of claim 2, wherein the proximal control device comprises a cam assembly within the housing, the proximal control device being configured to translate movement of the user actuator into movement in the cam assembly.

12. The system of claim 11, wherein the cam assembly is coupled with the first elongate member.

13. The system of claim 12, wherein the cam assembly is configured to move the first elongate member proximally with respect to the housing.

14. The system of claim 13, wherein the cam assembly comprises a rotatable cam having a slot, the first elongate member being coupled with a guide member received within the slot.

15. The system of claim 14, wherein the slot comprises a sloped slot portion and a radial slot portion.

16. The system of claim 14, wherein the cam assembly comprises an inner tube having a longitudinal slot with the guide member received in the longitudinal slot.

17. The system of claim 11, wherein the first gear assembly comprises a face gear having a first set of teeth that engage with teeth of another gear in the first gear assembly, wherein the face gear is coupled with the cam assembly such that movement of the face gear causes movement in the cam assembly.

18. The system of claim 11, wherein the proximal control device comprises a second gear assembly.

19. The system of claim 18, wherein movement in the cam assembly causes movement in the second gear assembly.

20. The system of claim 19, wherein the second gear assembly is coupled with the first elongate member and is configured to rotate the first elongate member with respect to the housing.

21. The system of claim 20, wherein the second gear assembly comprises a central gear having an aperture configured to receive the first elongate member such that rotation of the central gear causes rotation of the first elongate member.

22. The system of claim 21, wherein the second gear assembly comprises an annular gear coupled with the cam assembly and coupled with the central gear by way of a planetary gear assembly.

23. The system of claim 22, wherein the annular gear engages the planetary gear assembly such that rotation of the annular gear in a first direction causes first directional rotation of the central gear and rotation of the annular gear in a second direction causes second directional rotation of the central gear, the first directional rotation of the central gear being opposite to the second directional rotation.

24. The system of claim 2, wherein the proximal control device comprises a releasable lock mechanism that prevents the proximal portion of the implant held by the elongate grasper member from exiting the inner lumen.

25. The system of claim 24, wherein the lock mechanism comprises a movable tracking mechanism that interfaces with a groove in a face gear of the first gear assembly, the proximal control device configured such that movement of the face gear moves the tracking mechanism as the implant exits the inner lumen.

26. The system of claim 25, wherein the proximal control device is configured such that the tracking mechanism is prevented from further motion prior to the proximal portion of the implant exiting the inner lumen.

27. The system of claim 26, wherein the proximal control device comprises a release structure configured to be actuated by a user, wherein the release structure is configured to disengage the tracking mechanism from the face gear to allow the proximal portion of the implant to exit the inner lumen.

28. The system of claim 27, wherein the release structure is a pull tab.

29. The system of claim 27, wherein the release structure is coupled with the elongate grasper member.

* * * * *